(12) United States Patent
    Murakoshi et al.

(10) Patent No.: US 8,781,069 B2
(45) Date of Patent: Jul. 15, 2014

(54) RADIOGRAPHIC PHASE-CONTRAST IMAGING APPARATUS

(71) Applicant: FUJIFILM Corporation, Tokyo (JP)

(72) Inventors: Dai Murakoshi, Ashigarakami-gun (JP); Toshitaka Agano, Ashigarakami-gun (JP); Wataru Ito, Ashigarakami-gun (JP); Shinji Imai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/871,350

(22) Filed: Apr. 26, 2013

(65) Prior Publication Data
    US 2013/0235973 A1    Sep. 12, 2013

Related U.S. Application Data

(63) Continuation of application No. PCT/JP2011/006073, filed on Oct. 28, 2011.

(30) Foreign Application Priority Data

Oct. 29, 2010  (JP) ................................ 2010-244181
Nov. 16, 2010  (JP) ................................ 2010-256241

(51) Int. Cl.
    *G01N 23/04*    (2006.01)
    *A61B 6/00*     (2006.01)

(52) U.S. Cl.
    CPC ..................................... *A61B 6/484* (2013.01)
    USPC ............................................. 378/62; 378/36

(58) Field of Classification Search
    CPC .... A61B 6/484; A61B 6/4291; A61B 6/4233; A61B 6/4035
    USPC ............................................. 378/36, 37, 62
    See application file for complete search history.

(56) References Cited

U.S. PATENT DOCUMENTS

| | | |
|---|---|---|
| 5,085,502 A | 2/1992 | Womack et al. |
| 2007/0183558 A1 | 8/2007 | Hempel |

(Continued)

FOREIGN PATENT DOCUMENTS

| | | |
|---|---|---|
| JP | 5-306916 A | 11/1993 |
| JP | 2002-26300 A | 1/2002 |

(Continued)

OTHER PUBLICATIONS

Harold H. Wen et al., "Singe-shot x-ray differential phase-contrast and diffraction imaging using two-dimensional transmission gratings", Optic Letters, Jun. 2010, pp. 1932-1934, vol. 35, No. 12.

(Continued)

*Primary Examiner* — Courtney Thomas
(74) *Attorney, Agent, or Firm* — Sughrue Mion, PLLC

(57) ABSTRACT

A radiographic phase-contrast imaging apparatus obtains a phase-contrast image using two gratings including the first grating and the second grating. The first and second gratings are adapted to form a moire pattern when a periodic pattern image formed by the first grating is superimposed on the second grating. Based on the moire pattern detected by the radiographic image detector, image signals of the fringe images, which correspond to pixel groups located at different positions with respect to a predetermined direction, are obtained by obtaining image signals of pixels of each pixel group, which includes pixels arranged at predetermined intervals in the predetermined direction, as the image signal of each fringe image, where the predetermined direction is a direction parallel to or intersecting a period direction of the moire pattern other than a direction orthogonal to the period direction. Then, a phase-contrast image is generated based on the obtained fringe images.

34 Claims, 30 Drawing Sheets

(56) References Cited

U.S. PATENT DOCUMENTS

| | | |
|---|---|---|
| 2009/0316857 A1 | 12/2009 | David et al. |
| 2010/0220834 A1 | 9/2010 | Heismann et al. |
| 2010/0246765 A1 | 9/2010 | Murakoshi et al. |
| 2010/0290590 A1 | 11/2010 | Ouchi et al. |
| 2010/0322380 A1 | 12/2010 | Baeumer et al. |

FOREIGN PATENT DOCUMENTS

| | | |
|---|---|---|
| JP | 2007-203063 A | 8/2007 |
| JP | 2009-543080 A | 12/2009 |
| JP | 2010-190777 A | 9/2010 |
| JP | 2010-236986 A | 10/2010 |
| WO | 2008/102654 A1 | 8/2008 |
| WO | 2009/101569 A2 | 8/2009 |
| WO | 2010/050483 A1 | 5/2010 |

OTHER PUBLICATIONS

Zhentian Wang et al., "Fast X-Ray Phase-Contrast Imaging Using High Resolution Detector", IEEE Transactions on Nuclear Science, Jun. 2009, pp. 1383-1388, vol. 56, No. 3.

Zhi-Feng Huang et al., "Differential Phase-Contrast Imaging Experimental System Under the Incoherent Condition With Conventional X-Ray Tubes", IEEE Transactions on Nuclear Science, Jun. 2009, pp. 1438-1443, vol. 56, No. 3.

International Search Report for PCT/JP2011/006073 dated Nov. 29, 2011.

Office Action, dated Apr. 10, 2014, issued by the European Patent Office in corresponding European patent application No. 11835868.8-1657.

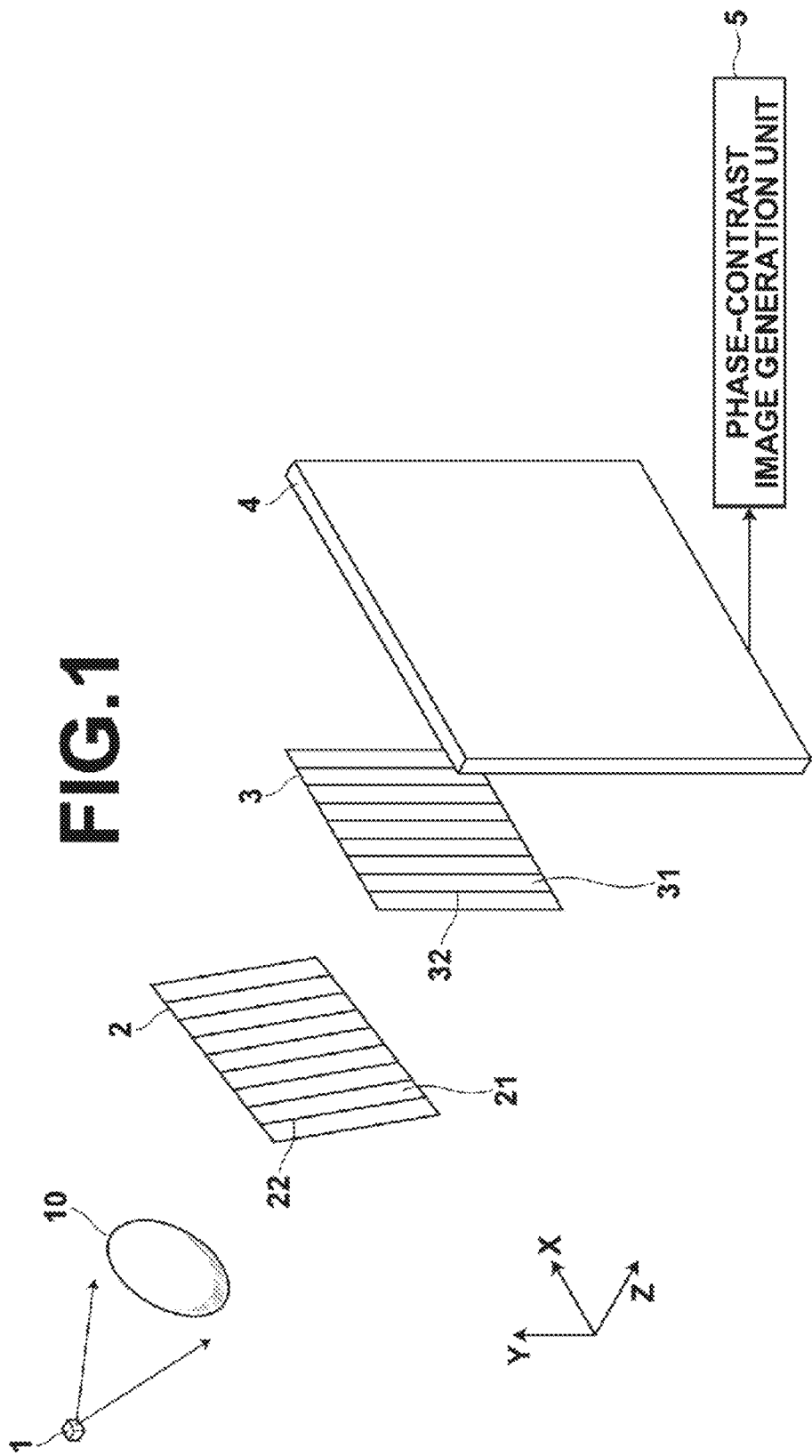

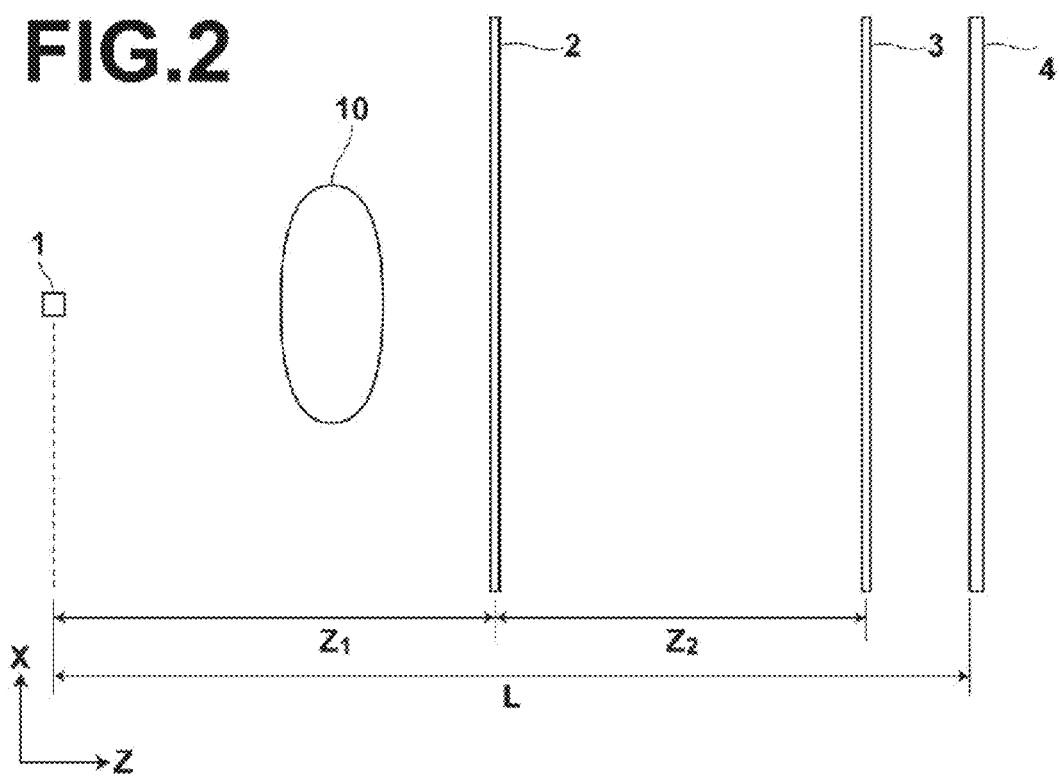
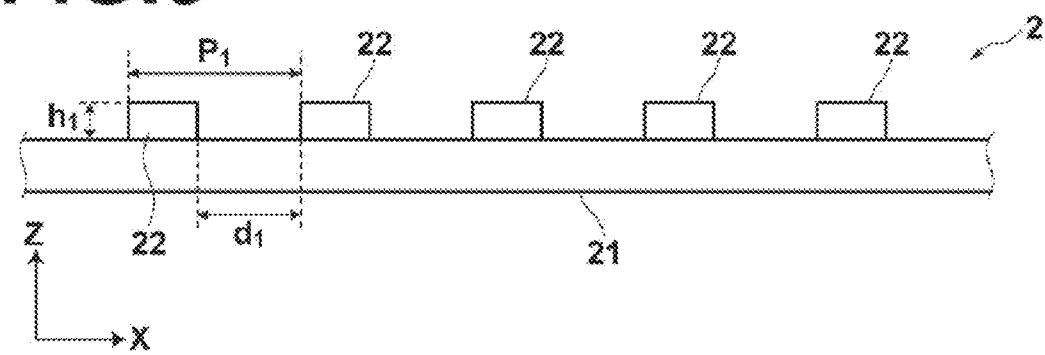
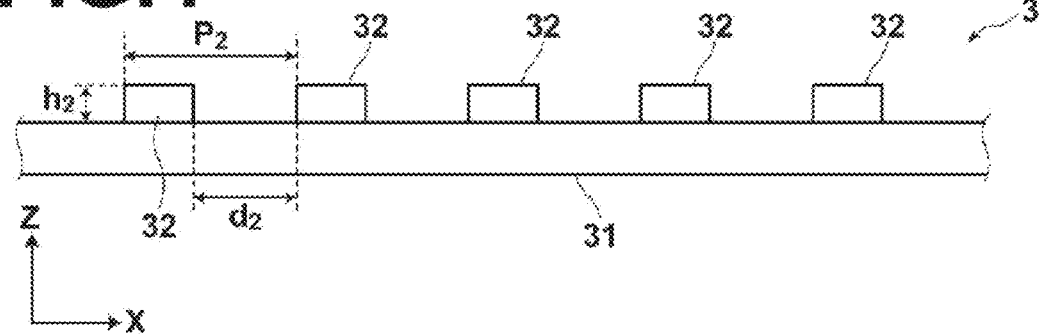

FIG.5
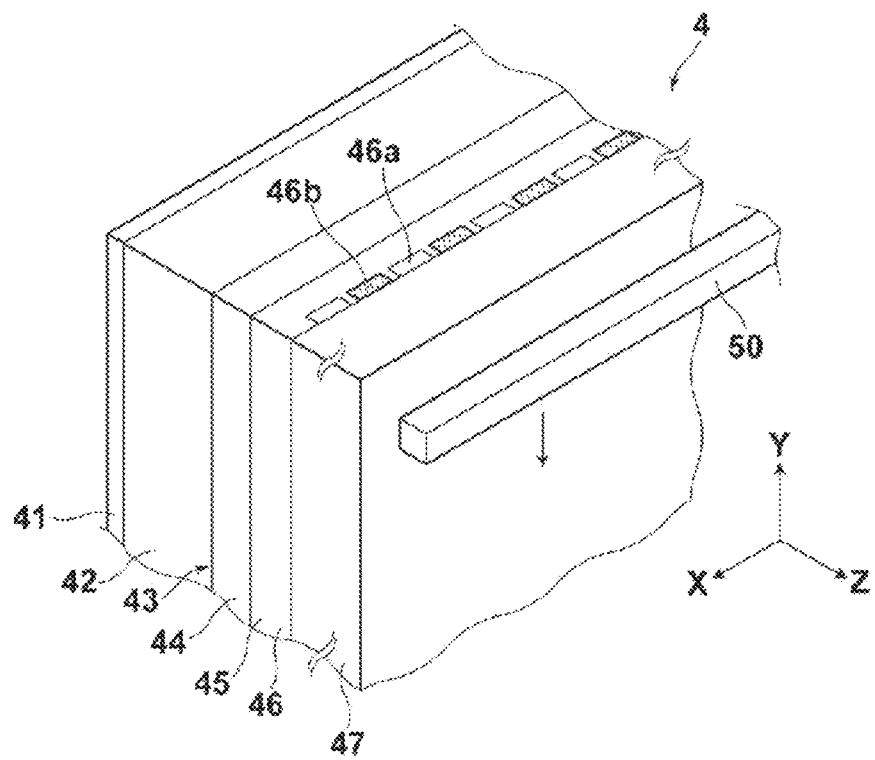
A
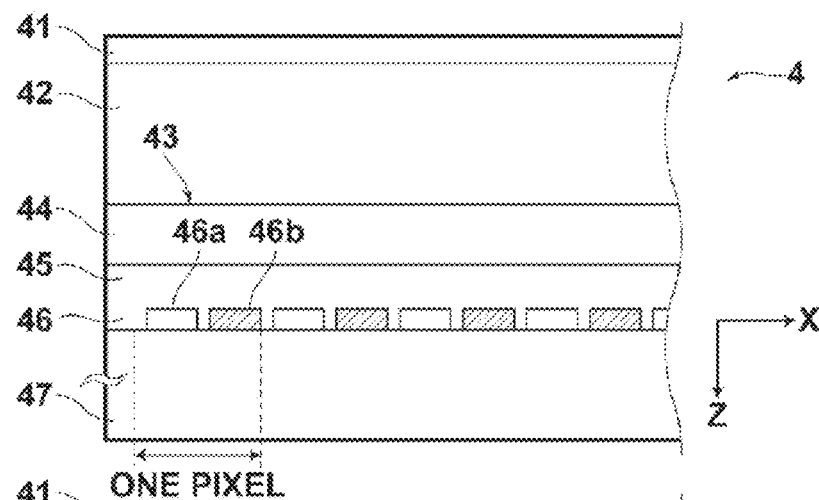
B
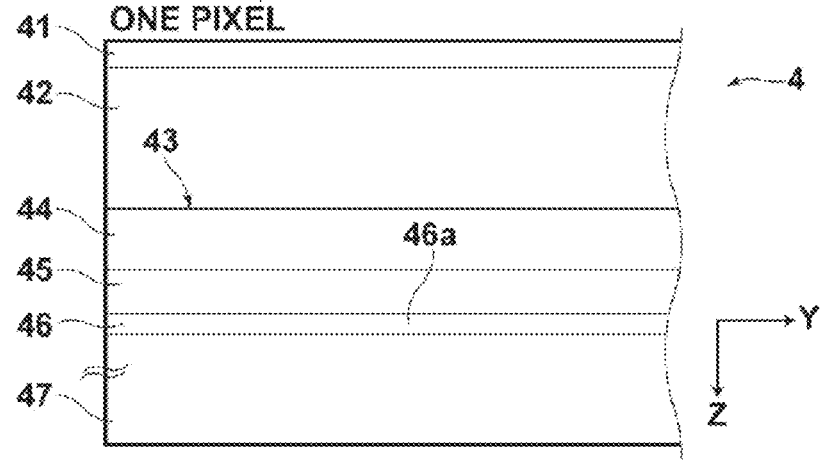
C

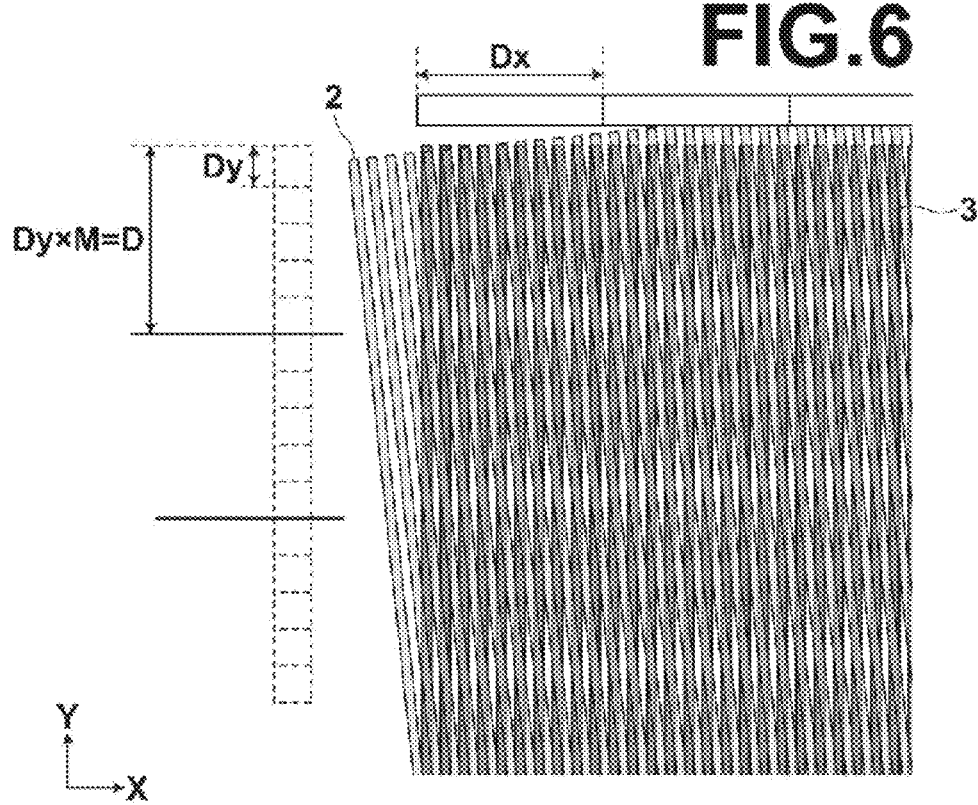
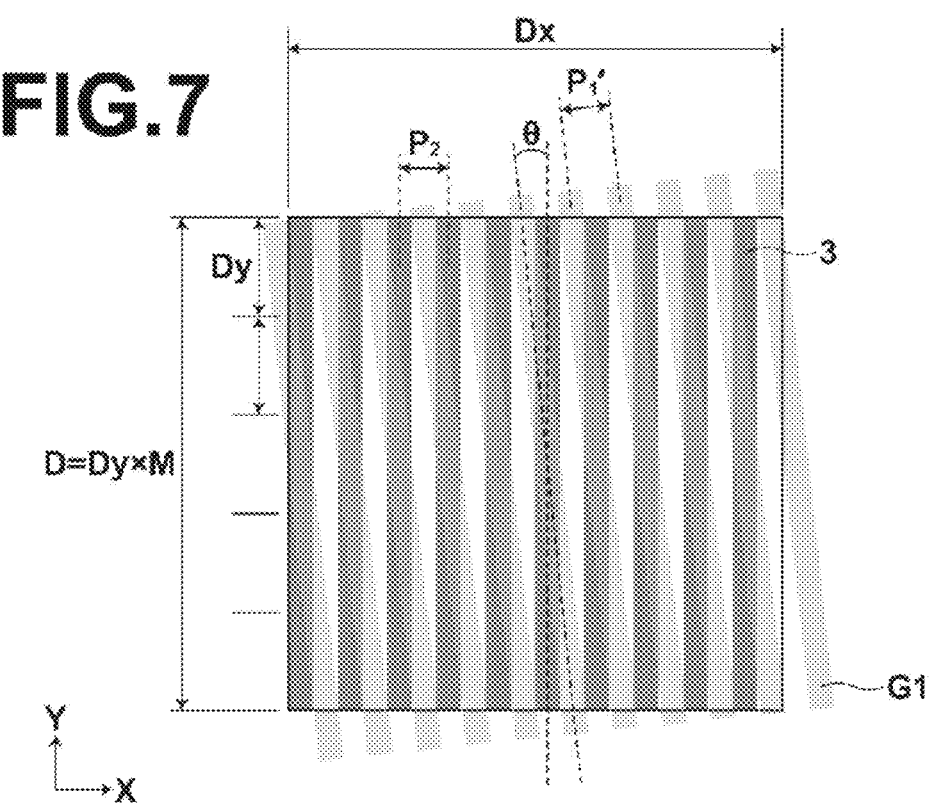

FIG.8
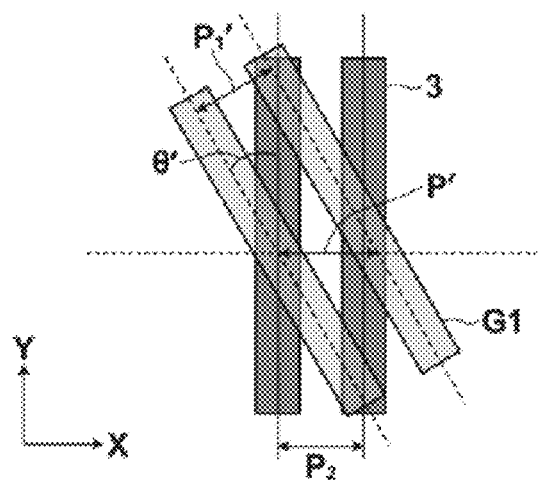
FIG.9
A
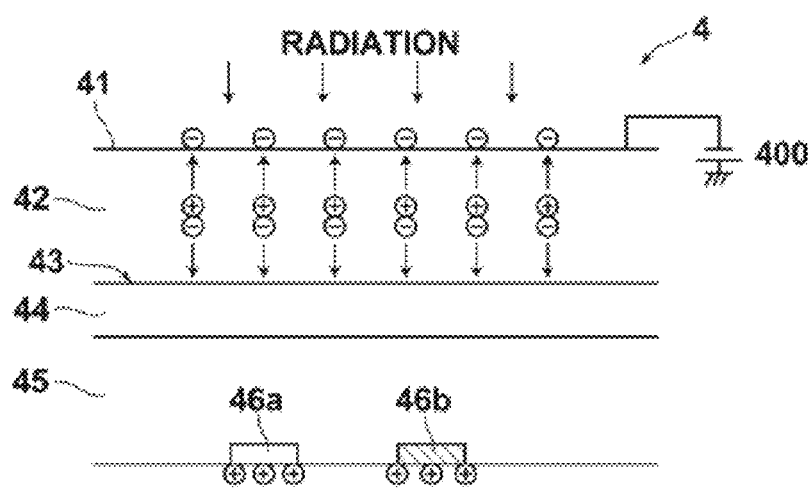
B
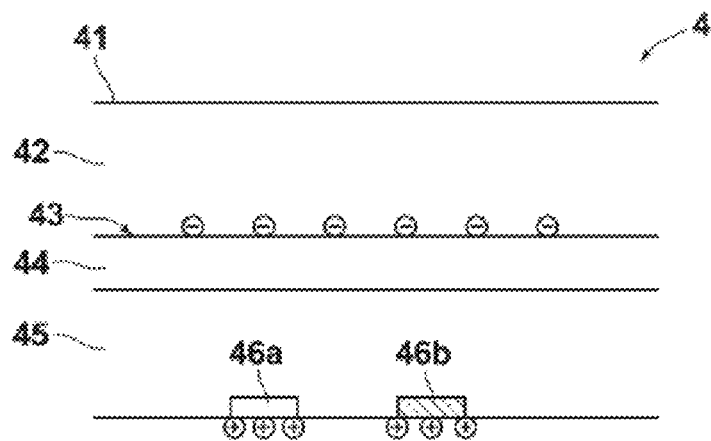

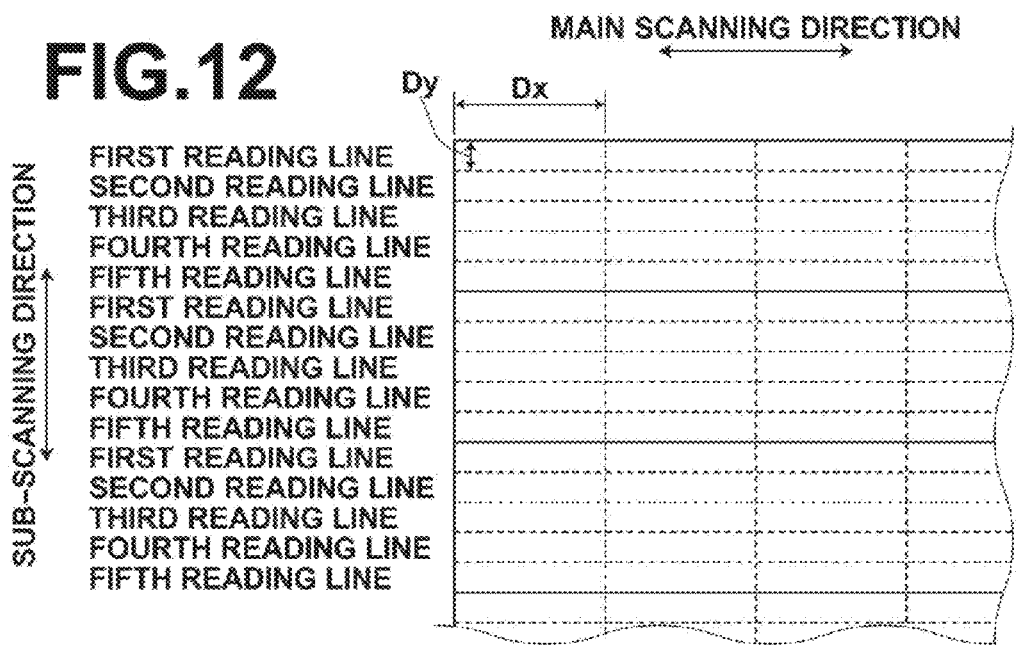
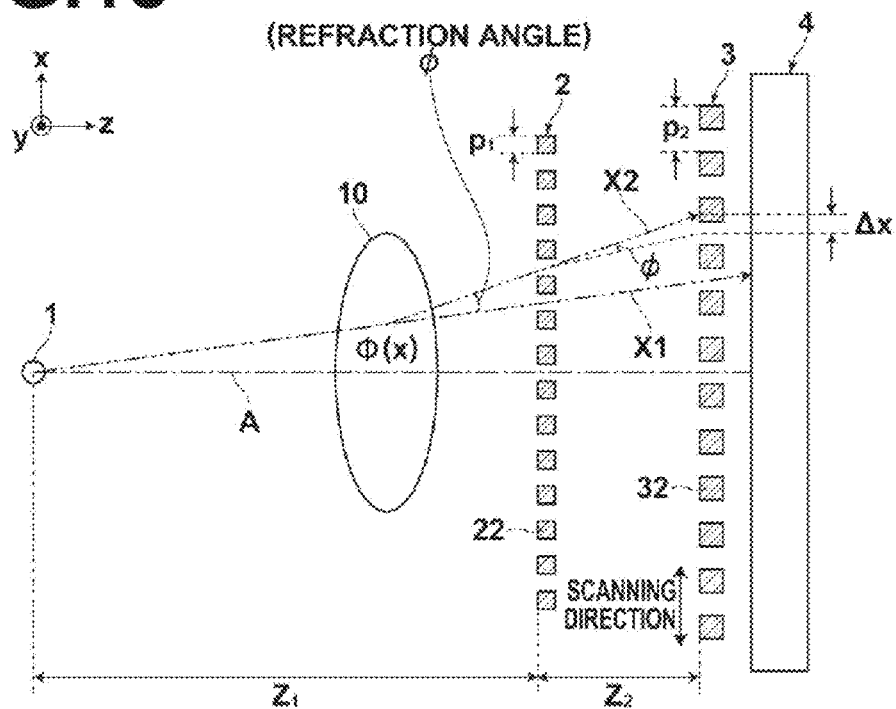

RADIOGRAPHIC PHASE-CONTRAST IMAGING APPARATUS

BACKGROUND OF THE INVENTION

1. Field of the Invention

The present invention relates to a radiographic phase-contrast imaging apparatus using gratings.

2. Description of the Related Art

X-rays have a nature that they attenuate depending on the atomic number of an element forming a substance and the density and thickness of the substance. Because of this nature, X-rays are used as a probe to investigate the interior of a subject. Imaging systems using X-rays have widely been used in the fields of medical diagnosis, nondestructive testing, etc.

With a typical X-ray imaging system, a subject is placed between an X-ray source, which emits an X-ray, and an X-ray image detector, which detects an X-ray image, to take a transmission image of the subject. In this case, each X-ray emitted from the X-ray source toward the X-ray image detector attenuates (is absorbed) by an amount depending on differences of characteristics (such as the atomic number, density and thickness) of substances forming the subject present in the path from the X-ray source to the X-ray image detector before the X-ray enters the X-ray image detector. As a result, an X-ray transmission image of the subject is detected and imaged by the X-ray image detector. As examples of such an X-ray image detector, a combination of an X-ray intensifying screen and a film, a photostimulable phosphor (storage phosphor), and a flat panel detector (FPD) using a semiconductor circuit are widely used.

However, the smaller the atomic number of an element forming a substance, the lower the X-ray absorbing capability of the substance. Therefore, there is only a small difference of the X-ray absorbing capability between soft biological tissues or soft materials, and it is difficult to obtain a sufficient contrast of the image as the X-ray transmission image. For example, articular cartilages forming a joint of a human body and synovial fluids around the cartilages are composed mostly of water, and therefore there is only a small difference of the X-ray absorption therebetween and it is difficult to obtain an image with sufficient contrast.

In recent years, X-ray phase-contrast imaging for obtaining a phase contrast image based on phase variation of X-rays due to differences between refractive indexes of a subject, in place of the intensity variation of X-rays due to differences between absorption coefficients of the subject, have been studied. With this X-ray phase-contrast imaging using the phase difference, a high contrast image can be obtained even in the case where the subject is a substance having low X-ray absorbing capability.

As an example of such an X-ray phase-contrast imaging system, a radiographic phase-contrast imaging apparatus has been proposed in International Patent Publication No. 2008/102654 and Japanese Unexamined Patent Publication No. 2010-190777 (hereinafter, Patent Documents 1 and 2), wherein two gratings including a first grating and a second grating are arranged parallel to each other at a predetermined interval, a self image of the first grating is formed at the position of the second grating due to the Talbot interference effect of the first grating, and the intensity of this self image is modulated with the second grating to provide a radiographic phase-contrast image.

With the radiographic phase-contrast imaging apparatus disclosed in Patent Documents 1 and 2, a fringe scanning method is performed, where the second grating is positioned almost parallel to the plane of the first grating, and the first grating or the second grating is relatively translated in a direction that is almost orthogonal to the direction of the grating by a predetermined amount that is smaller than the grating pitch. By performing an imaging operation each time the grating is translated, a plurality of images are taken. Based on these images, an amount of phase variation (phase shift differential) of an X-ray generated by interaction with the subject is obtained. Then, based on this phase shift differential, a phase-contrast image of the subject can be obtained.

SUMMARY OF THE INVENTION

With the radiographic phase-contrast imaging apparatus disclosed in Patent Documents 1 and 2, however, it is necessary to move the first or second grating at a pitch that is smaller than the grating pitch thereof with precision. The grating pitch is typically several micrometers, and even higher precision is required for the translation of the grating. This requires an extremely high precision moving mechanism, resulting in a complicated mechanism and increased costs. Further, there is a problem that, when an imaging operation is performed each time the grating is translated, a positional relationship between the subject and the imaging system may be changed due to motion of the subject and/or vibration of the apparatus during a series of imaging operations for obtaining a phase-contrast image. This hinders correctly deriving the phase variation of the X-ray generated by interaction with the subject, and hinders obtaining a good phase-contrast image, as a result.

In view of the above-described circumstances, the present invention is directed to providing a radiographic phase-contrast imaging apparatus that allows obtaining a good phase-contrast image by a single imaging operation without requiring a high precision moving mechanism.

A radiographic phase-contrast imaging apparatus of the invention is a radiographic phase-contrast imaging apparatus including: a radiation source; a first grating having a periodically arranged grating structure and allowing radiation emitted from the radiation source to pass therethrough to form a periodic pattern image; a second grating having a periodically arranged grating structure including areas transmitting the periodic pattern image formed by the first grating and areas shielding the periodic pattern image; and a radiographic image detector including two-dimensionally arranged pixels for detecting the radiation transmitted through the second grating, wherein the first grating and the second grating are adapted to form a moire pattern when the periodic pattern image formed by the first grating and the second grating are superimposed one another, and the radiographic phase-contrast imaging apparatus further including: a phase-contrast image generating unit for obtaining image signals of a plurality of fringe images based on an image signal of the moire pattern detected by the radiographic image detector, and generating a phase-contrast image based on the obtained image signals of the fringe images, wherein the fringe images correspond to different pixel groups located at different positions from one another with respect to a predetermined direction, each pixels group includes pixels arranged at intervals of a predetermined number of pixels in the predetermined direction, image signals read out from the pixels of each pixel group are obtained as the image signal of each fringe image, and the predetermined direction is a direction parallel to or a direction intersecting a period direction of the moire pattern other than a direction orthogonal to the period direction of the moire pattern.

In the radiographic phase-contrast imaging apparatus of the invention, the first grating and the second grating may be positioned such that a direction in which the periodic pattern image formed by the first grating extends and a direction in which the second grating extends are inclined relative to each other.

The first grating and the second grating may be configured such that a period T of the moire pattern has a value that satisfies the Expression below:

$$T = \frac{L}{Z_1 + Z_2} \times \frac{P_1'}{\tan\theta} \geq 3Dsub$$

where $Z_1$ is a distance between a focal spot of the radiation source and the first grating, $Z_2$ is a distance between the first grating and the second grating, L is a distance between the focal spot of the radiation source and the radiographic image detector, $P_1'$ is a pitch of the periodic pattern image at a position of the second grating, Dsub is a size of the pixel in the predetermined direction, and θ is an angle formed between the direction in which the periodic pattern image formed by the first grating extends and the direction in which the second grating extends.

A multislit, which is disposed between the radiation source and the first grating and is formed by an absorption type grating including a plurality of radiation shielding members arranged at a predetermined pitch for shielding the radiation applied from the radiation source in an area-selective manner, may further be provided, wherein the first grating and the second grating may be configured such that a period T of the moire pattern has a value that satisfies the Expression below:

$$T = \frac{L}{Z_1 + Z_2} \times \frac{P_1'}{\tan\theta} \geq 3Dsub$$

where $Z_1$ is a distance between a focal spot of the radiation source and the first grating, $Z_2$ is a distance between the first grating and the second grating, L is a distance between the focal spot of the radiation source and the radiographic image detector, $P_1'$ is a pitch of the periodic pattern image at a position of the second grating, Dsub is a size of the pixel in the predetermined direction, and θ is an angle formed between the direction in which the periodic pattern image formed by the first grating extends and the direction in which the second grating extends.

A pitch $P_3$ of the multislit may have a value that satisfies the Expression below:

$$P_3 = \frac{Z_3}{Z_2} P_1'$$

where $Z_3$ is a distance between the multislit and the first grating, $Z_2$ is a distance from the first grating to the second grating, and $P_1'$ is a pitch of the periodic pattern image at a position of the second grating.

A relative inclination angle θ between the periodic pattern image formed by the first grating and the second grating may be set to be a value that satisfies the Expression below:

$$\theta = \arctan\left\{n \times \frac{P_1'}{D}\right\}$$

where $P_1'$ is a pitch of the periodic pattern image at a position of the second grating, D is a value of the size of the pixel in the predetermined direction multiplied by the number of fringe images M, and n is an integer other than 0 or a multiple of M.

The first grating may be a phase modulation grating that applies phase modulation of 90° or an amplitude modulation grating, and a pitch $P_1'$ of the periodic pattern image at a position of the second grating and a pitch $P_2$ of the second grating may be values that satisfy the Expression below:

$$P_2 = P_1' = \frac{Z_1 + Z_2}{Z_1} P_1$$

where $P_1$ is a grating pitch of the first grating, $Z_1$ is a distance from a focal spot of the radiation source to the first grating, and $Z_2$ is a distance from the first grating to the second grating.

The first grating may be a phase modulation grating that applies phase modulation of 180°, and a pitch $P_1'$ of the periodic pattern image at a position of the second grating and a pitch $P_2$ of the second grating may be values that satisfy the Expression below:

$$P_2 = P_1' = \frac{Z_1 + Z_2}{Z_1} \frac{P_1}{2}$$

where $P_1$ is a grating pitch of the first grating, $Z_1$ is a distance from a focal spot of the radiation source to the first grating, and $Z_2$ is a distance from the first grating to the second grating.

The radiographic image detector may include the pixels two-dimensionally arranged in first and second directions that are orthogonal to each other, and the direction in which the periodic pattern image formed by the first grating extends or the direction in which the second grating extends may be parallel to the first direction.

The phase-contrast image generating unit may obtain the image signals of the fringe images based on image signals read out from a predetermined number of pixels in the first direction depending on the relative inclination between the direction in which the periodic pattern image formed by the first grating extends and the direction in which the second grating extends.

The first grating and the second grating may be configured such that a pitch of the periodic pattern image at a position of the second grating is different from a pitch of the second grating. In this case, the direction in which the periodic pattern image formed by the first grating extends may be parallel to the direction in which the second grating extends.

The first grating and the second grating may be configured such that a period T of the moire pattern has a value that satisfies the Expression below:

$$T = \frac{L}{Z_1 + Z_2} \times \left|\frac{P_1' P_2}{P_1' - P_2}\right| \geq 3Dsub$$

where $Z_1$ is a distance between a focal spot of the radiation source and the first grating, $Z_2$ is a distance between the first grating and the second grating, L is a distance between the focal spot of the radiation source and the radiographic image detector, $P_2$ is a pitch of the second grating, $P_1'$ is a pitch of the periodic pattern image at a position of the second grating, and Dsub is a size of the pixel in the predetermined direction.

A multislit, which is disposed between the radiation source and the first grating and is formed by an absorption type grating including a plurality of radiation shielding members arranged at a predetermined pitch for shielding the radiation applied from the radiation source in an area-selective manner, may further be provided, wherein the first grating and the second grating may be configured such that a period T of the moire pattern has a value that satisfies the Expression below:

$$T = \frac{L}{Z_1 + Z_2} \times \left| \frac{P'_1 P_2}{P'_1 - P_2} \right| \geq 3Dsub$$

where $Z_1$ is a distance between a focal spot or the radiation source and the first grating, $Z_2$ is a distance between the first grating and the second grating, L is a distance between the focal spot of the radiation source and the radiographic image detector, $P_2$ is a pitch of the second grating, $P_1'$ is a pitch of the periodic pattern image at a position of the second grating, and Dsub is a size of the pixel in the predetermined direction.

A pitch $P_3$ of the multislit may have a value that satisfies the Expression below:

$$P_3 = \frac{Z_3}{Z_2} P'_1$$

where $Z_3$ is a distance between the multislit and the first grating, $Z_2$ is a distance from the first grating to the second grating, and $P_1'$ is a pitch of the periodic pattern image at a position of the second grating.

The first grating may be a phase modulation grating that applies phase modulation of 90° or an amplitude modulation grating, and the pitch $P_1'$ of the periodic pattern image formed by the first grating at the position of the second grating may have a value that satisfies the Expression below:

$$P'_1 = \frac{Z_1 + Z_2}{Z_1} P_1$$

where $P_1$ is a grating pitch of the first grating, $Z_1$ is a distance from a focal spot of the radiation source to the first grating, and $Z_2$ is a distance from the first grating to the second grating.

The first grating may be a phase modulation grating that applies phase modulation of 180°, and the pitch $P_1'$ of the periodic pattern image formed by the first grating at the position of the second grating may have a value that satisfies the Expression below:

$$P'_1 = \frac{Z_1 + Z_2}{Z_1} \frac{P_1}{2}$$

where $P_1$ is a grating pitch of the first grating, $Z_1$ is a distance from a focal spot of the radiation source to the first grating, and $Z_2$ is a distance from the first grating to the second grating.

The radiographic image detector may include the pixels being two-dimensionally arranged and provided with switching elements for reading out the image signals.

A linear reading light source for emitting linear reading light may further be provided, wherein reading of the image signals from the radiographic image detector may be achieved by scanning of the linear reading light source.

The phase-contrast image generating unit may obtain image signals read out from pixels adjacent to each other in the predetermined direction as the image signals of different fringe images.

The phase-contrast image generating unit may obtain image signals read out from pixels arranged at intervals of at least two pixels in the predetermined direction of each pixel group as the image signal of each fringe image, and may obtain the image signals read out from the different pixel groups as the image signals of different fringe images.

The second grating may be positioned at a Talbot interference distance from the first grating, and may apply intensity modulation to the periodic pattern image formed by a Talbot interference effect of the first grating.

The first grating may be an absorption type grating that allows the radiation to pass therethrough as a projection image to form the periodic pattern image, and the second grating may apply intensity modulation to the periodic pattern image that is the projection image transmitted through the first grating.

The second grating may be positioned at a distance shorter than a minimum Talbot interference distance from the first grating.

The size of the pixel in the predetermined direction may be smaller than a size of the pixel in a direction orthogonal to the predetermined direction.

The radiation source and the radiographic image detector may be positioned to face each other in the horizontal direction, and the radiographic phase-contrast imaging apparatus may be adapted to be capable of imaging a subject in the upright position.

The radiation source and the radiographic image detector may be positioned to face each other in the vertical direction, and the radiographic phase-contrast imaging apparatus may be adapted to be capable of imaging a subject in the supine position.

The radiation source and the radiographic image detector may be held by a pivoting arm, and the radiographic phase-contrast imaging apparatus may be adapted to be capable of imaging a subject in the upright position and imaging a subject in the supine position.

The radiographic phase-contrast imaging apparatus may be a mammographic apparatus adapted to be capable of imaging a breast as a subject.

A moving mechanism for moving the radiation source between a first position, from which the radiation is applied to the radiographic image detector from a first direction, and a second position, from which the radiation is applied to the radiographic image detector from a second direction different from the first direction, wherein the phase-contrast image generating unit generates a phase-contrast image based on the image signals detected by the radiographic image detector at each of the first position and the second position; and a stereo image forming unit for forming a stereo image based on the phase-contrast image corresponding to the first position and the phase-contrast image corresponding to the second position may further be provided.

An orbiting mechanism for making the radiation source and the radiographic image detector orbit about a subject, wherein the phase-contrast image generating unit generates a phase-contrast image at each angle of rotation provided by the orbiting mechanism based on the image signals detected by the radiographic image detector at the angle of rotation; and a three-dimensional image forming unit for forming a three-dimensional image based on the phase-contrast images at the angles of rotation may further be provided.

A rotating mechanism for rotating the first and second gratings by an angle of 90° from directions along which the gratings extend about an axis of rotation extending orthogonally to grating surfaces of the first and second gratings may further be provided.

The first and second gratings may be configured as two-dimensional gratings.

A radiographic phase-contrast imaging apparatus of the invention is a radiographic phase-contrast imaging apparatus including: a radiation source; a first grating having a periodically arranged grating structure and allowing radiation emitted from the radiation source to pass therethrough to form a periodic pattern image; a second grating having a periodically arranged grating structure including areas transmitting the periodic pattern image formed by the first grating and areas shielding the periodic pattern image; and a radiographic image detector including two-dimensionally arranged pixels for detecting the radiation transmitted through the second grating, wherein the first grating and the second grating are adapted to form a moire pattern when the periodic pattern image formed by the first grating and the second grating are superimposed one another, and the radiographic phase-contrast imaging apparatus further including: a phase-contrast image generating unit for obtaining image signals of a plurality of fringe images based on an image signal of the moire pattern detected by the radiographic image detector, and generating at least one of a phase-contrast image, a small-angle scattering image and an absorption image based on the obtained image signals of the fringe images, wherein the fringe images correspond to different pixel groups located at different positions from one another with respect to a predetermined direction, each pixels group includes pixels arranged at intervals of a predetermined number of pixels in the predetermined direction, image signals read out from the pixels of each pixel group are obtained as the image signal of each fringe image, and the predetermined direction is a direction parallel to or a direction intersecting a period direction of the moire pattern other than a direction orthogonal to the period direction of the moire pattern.

According to the radiographic phase-contrast imaging apparatus of the invention, the first grating and the second grating are adapted to form a moire pattern when the periodic pattern image formed by the first grating and the second grating are superimposed one another. Based on an image signal of the moire pattern detected by the radiographic image detector, image signals of the fringe images, which correspond to different pixel groups located at different positions from one another with respect to a predetermined direction, are obtained by obtaining image signals read out from pixels of each pixel group, which includes pixels arranged at intervals of a predetermined number of pixels in the predetermined direction, as the image signal of each fringe image, where the predetermined direction is a direction parallel to or a direction intersecting a period direction of the moire pattern other than a direction orthogonal to the period direction of the moire pattern. Then, a phase-contrast image is generated based on the obtained image signals of the fringe images. Therefore, a plurality of fringe images used to obtain a radiographic phase-contrast image can be obtained by a single imaging operation without requiring a high precision moving mechanism for moving the second grating, which has conventionally been required.

BRIEF DESCRIPTION OF THE DRAWINGS

FIG. 1 is a diagram illustrating the schematic configuration of a radiographic phase-contrast imaging apparatus according to a first embodiment of the present invention, FIG. 2 is a plan view of the radiographic phase-contrast imaging apparatus shown in FIG. 1, FIG. 3 is a diagram illustrating the schematic structure of a first grating, FIG. 4 is a diagram illustrating the schematic structure of a second grating, FIG. 5 is a diagram illustrating the schematic structure of a radiographic image detector using an optical reading system, FIG. 6 is a diagram illustrating a positional relationship among the first grating, the second grating and pixels of the radiographic image detector, FIG. 7 is a diagram for explaining a method for setting an inclination angle of a self image of the first grating relative to the second grating, FIG. 8 is a diagram for explaining a method for adjusting the inclination angle of the self image of the first grating relative to the second grating, FIG. 9 is a diagram for explaining a recording operation of the radiographic image detector using the optical reading system, FIG. 12 is a diagram for explaining the operation to obtain the fringe images based on the image signals read out from the radiographic image detector using the optical reading system, FIG. 13 is a diagram illustrating an example of one radiation path which is refracted depending on a phase shift distribution Φ(x) of a subject with respect to an X-direction.

DESCRIPTION OF THE PREFERRED EMBODIMENTS

Figure 10:
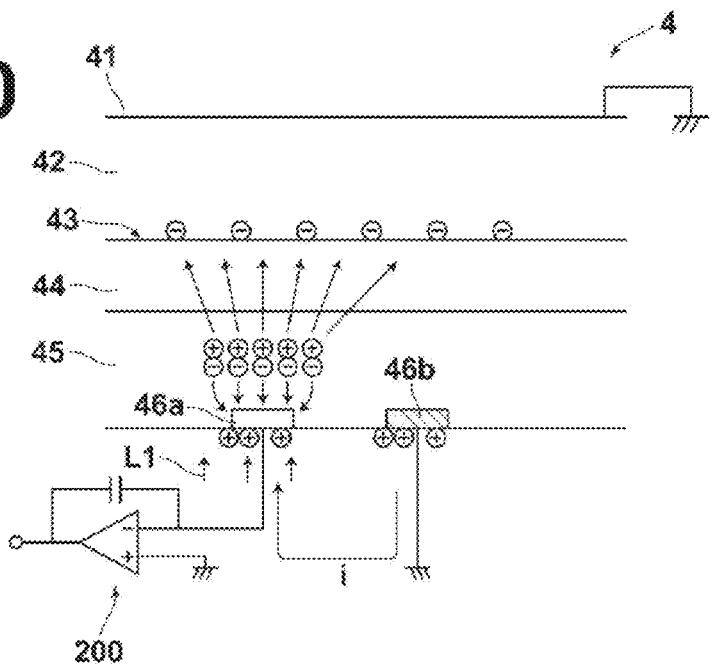
FIG. 10 is a diagram for explaining a reading operation of the radiographic image detector using the optical reading system.

Hereinafter, a radiographic phase-contrast imaging apparatus according to a first embodiment of the present invention will be described with reference to the drawings. FIG. 1 illustrates the schematic configuration of the radiographic phase-contrast imaging apparatus of the first embodiment. FIG. 2 illustrates a plan view (X-Z sectional view) of the radiographic phase-contrast imaging apparatus shown in FIG. 1. The paper thickness direction of FIG. 2 corresponds to the Y-direction in FIG. 1.

As shown in FIG. 1, the radiographic phase-contrast imaging apparatus includes: a radiation source 1, which emits radiation toward a subject 10; a first grating 2, which allows the radiation emitted from the radiation source 1 to pass therethrough to form a periodic pattern image; a second grating 3, which has a periodically arranged grating structure including areas transmitting the periodic pattern image formed by the first grating 2 (which will hereinafter be referred to as "self image G1 of the first grating 2") and areas shielding the self image G1 of the first grating 2; a radiographic image detector 4, which detects the radiation transmitted through the second grating 3; and a phase-contrast image generation unit 5, which obtains fringe images based on image signals detected by the radiographic image detector 4 and generates a phase-contrast image based on the obtained fringe images.

The radiation source 1 emits radiation toward the subject 10. The spatial coherence of the radiation is such that the Talbot interference effect occurs when the radiation is applied to the first grating 2. For example, a microfocus X-ray tube or a plasma X-ray source, which provides a small radiation emission point, may be used.

As shown in FIG. 3, the first grating 2 includes a substrate 21, which mainly transmits the radiation, and a plurality of members 22 disposed on the substrate 21. The members 22 are linear members extending in one direction in a plane orthogonal to the optical axis of the radiation (the Y-direction orthogonal to the X-direction and Z-direction, i.e., the paper thickness direction of FIG. 3). The members 22 are arranged at a predetermined interval $d_1$ with a constant period $P_1$ in the X-direction. The material forming the members 22 may be a metal, such as gold or platinum. It is desirable that the first grating 2 is a so-called phase modulation grating, which applies phase modulation of about 90° or about 180° to the radiation applied thereto. It is preferable that a thickness $h_1$ of the members 22 is set depending on energy of the radiation used for imaging. An X-ray energy region for usual medical imaging diagnosis is 30 to 120 keV. Therefore, if the members 22 are made of gold, for example, the necessary thickness $h_1$ of gold is around 1 μm to 10 μm. Alternatively, the first grating 2 may be an amplitude modulation grating. If the first grating 2 is an amplitude modulation grating, the members 22 need to have a thickness for sufficiently absorbing the radiation. If the members 22 are made of gold, for example, the necessary thickness $h_1$ of gold for the above X-ray energy region is around 10 μm to 300 μm.

As shown in FIG. 4, the second grating 3 includes, similarly to the first grating 2, a substrate 31, which mainly transmits the radiation, and a plurality of members 32 disposed on the substrate 31. The members 32 shield the radiation. The members 32 are linear members extending in one direction in a plane orthogonal to the optical axis of the radiation (the Y-direction orthogonal to the X-direction and Z-direction, i.e., the paper thickness direction of FIG. 4). The members 32 are arranged at a predetermined interval $d_2$ with a constant period $P_2$ in the X-direction. The material forming the members 32 may be a metal, such as gold or platinum. It is desirable that the second grating 3 is an amplitude modulation grating. It is preferable that a thickness $h_2$ of the members 32 is set depending on energy of the radiation used for imaging. The members 32 need to have a thickness for sufficiently absorbing the radiation. If the members 32 are made of gold, for example, the necessary thickness $h_2$ of gold for the above-mentioned X-ray energy region is around 10 μm to 300 μm.

In general, the radiation emitted from the radiation source 1 is not a parallel beam but a cone beam, which propagates from the focal spot of the radiation with spreading at a predetermined angle. Therefore, the self image G1 formed by the radiation emitted from the radiation source 1 and passed through the first grating 2 is magnified in proportion to the distance from the focal spot of the radiation source 1. For this reason, in this embodiment, the grating pitch $P_2$ and the interval $d_2$ of the second grating 3 are determined such that the slits of the second grating 3 are almost aligned with the periodic pattern of light areas of self image G1 of the first grating 2 at the position of the second grating 3 with taking magnification of the self image G1 depending on the distance from the focal spot of the radiation source 1 into account. That is, assuming that the distance from the focal spot of the radiation source 1 to the first grating 2 is $Z_1$ and the distance from the first grating 2 to the second grating 3 is $Z_2$ (see FIG. 2), in the case where the first grating 2 is a phase modulation grating that applies phase modulation of 90° or an amplitude modulation grating, the pitch $P_2$ and the interval $d_2$ of the second grating is determined to satisfy the relationships defined as the Expressions (1) and (2) below, respectively:

$$P_2 = \frac{Z_1 + Z_2}{Z_1} P_1 \quad (1)$$

$$d_2 = \frac{Z_1 + Z_2}{Z_1} d_1 \quad (2)$$

Further, in the case where the first grating 2 is a phase modulation grating that applies phase modulation of 180°, taking the fact that the pitch of the self image G1 of the first grating 2 formed by the radiation passed through the first grating 2 is ½ of the grating pitch $P_1$ of the first grating 2 into account, it is desirable that the pitch $P_2$ and the interval $d_2$ of the second grating satisfy the relationships defined as the Expressions (3) and (4) below, respectively, in place of the Expressions (1) and (2) above:

$$P_2 = \frac{Z_1 + Z_2}{2Z_1} P_1 \quad (3)$$

$$d_2 = \frac{Z_1 + Z_2}{2Z_1} d_1 \quad (4)$$

It should be noted that, in the case where the radiation applied from the radiation source 1 is a parallel beam, the self image G1 of the first grating 2 formed by the radiation passed through the first grating 2 is not magnified depending on the distance from the radiation source 1. Therefore, if the first grating 2 is a phase modulation grating that applies phase modulation of 90° or an amplitude modulation grating, $P_2=P_1$ and $d_2=d_1$. Alternatively, if the first grating 2 is a phase modulation grating that applies phase modulation of 180°, $P_2=P_1/2$ and $d_2=d_1/2$.

The radiographic image detector 4 detects, as an image signal, an intensity-modulated image, which is modulated by the second grating 3, of the self image G1 of the first grating 2 formed by the radiation entering the first grating 2. As this type of radiographic image detector 4, a radiographic image detector using a so-called optical reading system, which is a direct conversion-type radiographic image detector, from which image signals are read out by scanning with linear reading light, is used in this embodiment.

FIG. 5 shows at "A" a perspective view of the radiographic image detector 4 of this embodiment, shows at "B" a sectional view taken along the X-Z plane of the radiographic image detector shown at A in FIG. 5, and shows at "C" a sectional view taken along the Y-Z plane of the radiographic image detector shown at A in FIG. 5.

As shown at A to C in FIG. 5, the radiographic image detector 4 of this embodiment includes: a first electrode layer 41, which transmits radiation; a recording photoconductive layer 42, which generates electric charges when exposed to the radiation transmitted through the first electrode layer 41; an electric charge transporting layer 44, which acts as an insulator against the electric charges of one of the polarities generated at the recording photoconductive layer 42 and acts as an conductor for the electric charges of the other of the polarities generated at the recording photoconductive layer 42; a reading photoconductive layer 45, which generates electric charges when exposed to reading light; and a second electrode layer 46, which are formed in layers in this order. An electric charge storage area 43, which stores the electric charges generated in the recording photoconductive layer 42, is formed in the vicinity of interface between the recording photoconductive layer 42 and the electric charge transporting layer 44. It should be noted that the above-described layers are formed on a glass substrate 47 in the order from the second electrode layer 46.

The first electrode layer 41 is made of a material that transmits radiation. Examples of the usable material may include NESA film ($SnO_2$), ITO (Indium Tin Oxide), IZO (Indium Zinc Oxide), and IDIXO (Idemitsu Indium X-metal Oxide, available from Idemitsu Kosan Co., Ltd.) which is an amorphous light-transmitting oxide film, etc., and the thickness thereof is in the range from 50 to 200 nm. As other examples, Al or Au with a thickness of 100 nm may be used. The recording photoconductive layer 42 is made of a material that generates electric charges when exposed to radiation. In view of relatively high quantum efficiency with respect to radiation and high dark resistance, a material mainly composed of a-Se is used. An appropriate thickness thereof is in the range from 10 µm to 1500 µm. For mammography, in particular, the thickness of the recording photoconductive layer 42 is preferably in the range from 150 µm to 250 µm. For general imaging, the thickness of the recording photoconductive layer 42 is preferably in the range from 500 µm to 1200 µm.

As the electric charge transporting layer 44, for example, one that provides a larger difference (for example, $10^2$ or more, or desirably $10^3$ or more) between the mobility of the electric charges charged in the first electrode layer 41 and the mobility of the electric charges having the opposite polarity when the radiographic image is recorded is preferred. Suitable examples thereof may include organic compounds, such as poly N-vinylcarbazole (PVK), N,N'-diphenyl-N,N'-bis(3-methylphenyl)-[1,1'-biphenyl]-4,4'-diamine (TPD), discotic liquid crystal, etc., or semiconductor materials, such as a polymer (polycarbonate, polystyrene, PVK) dispersion of TPD, a-Se doped with 10 to 200 ppm of Cl, $As_2Se_3$, etc. A suitable thickness of the electric charge transporting layer 44 is around 0.2 to 2 µm.

The reading photoconductive layer 45 is made of a material that becomes conductive when exposed to the reading light. Examples thereof may include photoconductive materials mainly composed of at least one of a-Se, Se—Te, Se—As—Te, metal-free phthalocyanine, metal phthalocyanine, MgPc (Magnesium phthalocyanine), VoPc (phase II of Vanadyl phthalocyanine), CuPc (Copper phthalocyanine), etc. An appropriate thickness of the reading photoconductive layer 44 may be around 5 to 20 µm.

The second electrode layer 46 includes a plurality of transparent linear electrodes 46a, which transmit the reading light, and a plurality of light-shielding linear electrodes 46b, which shield the reading light. The transparent linear electrodes 46a and the light-shielding linear electrodes 46b continuously extend in straight lines from one end to the other end of an imaging area of the radiographic image detector 4. As shown at A and B in FIG. 5, the transparent linear electrodes 46a and the light-shielding linear electrodes 46b are alternately arranged at a predetermined interval. The transparent linear electrodes 46a are made of a material that transmits the reading light and is electrically conductive. For example, similarly to the first electrode layer 41, the transparent linear electrodes 46a may be made of ITO, IZO or IDIXO. The thickness thereof is around 100 to 200 nm.

The light-shielding linear electrodes 46b are made of a material that shields the reading light and is electrically conductive. For example, the light-shielding linear electrodes 46b may be formed by a combination of the above-described transparent electrically conducting material and a color filter. The thickness of the transparent electrically conducting material is around 100 to 200 nm.

In the radiographic image detector 4 of this embodiment, one set of the transparent linear electrode 46a and the light-shielding linear electrode 46b adjacent to each other is used to read out an image signal, as described in detail later. Namely, as shown at B in FIG. 5, one set of the transparent linear electrode 46a and the light-shielding linear electrode 46b reads out an image signal of one pixel. In this embodiment, the transparent linear electrodes 46a and the light-shielding linear electrodes 46b are arranged such that one pixel is substantially 50 µm.

As shown at A in FIG. 5, the radiographic phase-contrast imaging apparatus of this embodiment also includes a linear reading light source 50, which extends in a direction (the X-direction) orthogonal to the direction in which the transparent linear electrodes 46a and the light-shielding linear electrodes 46b extend. The linear reading light source 50 in this embodiment is formed by a light source, such as LED (Light Emitting Diode) or LD (Laser Diode), and a predetermined optical system, and is adapted to apply linear reading light having a width of substantially 10 µm to the radiographic image detector 4 in the direction (the Y-direction) in which the transparent linear electrodes 46a and the light-shielding linear electrodes 46b extend. The linear reading light source 50 is moved by a predetermined moving mechanism (not shown) relative to the direction (the Y-direction) in which the transparent linear electrodes 46a and the light-shielding linear electrodes 46b extend. As the linear reading light source 50 is moved in this manner, the linear reading light emitted from the linear reading light source 50 scans the radiographic image detector 4 to read out the image signals. The operation of reading the image signals will be described in detail later.

The radiation source 1, the first grating 2, the second grating 3 and the radiographic image detector 4 form the radiographic phase-contrast imaging apparatus that is capable of obtaining a radiographic phase-contrast image. In order to make this configuration function as a Talbot interferometer, some more conditions must almost be satisfied. Now, the conditions are described. It should be noted that the expression "almost be satisfied" or "almost satisfy" with respect to the various conditions described below refers to that, since the energy, or wavelength, of the radiation emitted from the radiation source is not uniform and varies to some extent, there is a tolerance for the energy range of the radiation, and that there is a tolerable range which can provide at least a phase-contrast image of this embodiment, although it is not an optimal range and thus results in lower performances, such as lower image quality.

First, it is necessary that grid planes of the first grating 2 and the second grating 3 are parallel to the X-Y plane shown in FIG. 1.

Further, if the first grating 2 is a phase modulation grating that applies phase modulation of 90°, then, the distance $Z_2$ between the first grating 2 and the second grating 3 must almost satisfy the condition below:

$$Z_2 = \left(m + \frac{1}{2}\right)\frac{P_1 P_2}{\lambda} \quad (5)$$

where λ is the wavelength of the radiation (which is typically the effective wavelength of the radiation entering the first grating 2), m is 0 or a positive integer, $P_1$ is the above-described grating pitch of the first grating 2, and $P_2$ is the above-described grating pitch of the second grating 3.

Alternatively, if the first grating 2 is a phase modulation grating that applies phase modulation of 180°, then, the condition below must almost be satisfied:

$$Z_2 = \left(m + \frac{1}{2}\right)\frac{P_1 P_2}{2\lambda} \quad (6)$$

where λ is the wavelength of the radiation (which is typically the effective wavelength of the radiation entering the first grating 2), m is 0 or a positive integer, $P_1$ is the above-described grating pitch of the first grating 2, and $P_2$ is the above-described grating pitch of the second grating 3.

Still alternatively, if the first grating 2 is an amplitude modulation grating, then, the condition below must almost be satisfies:

$$Z_2 = m \frac{P_1 P_2}{\lambda} \tag{7}$$

It should be noted that the Expressions (5), (6) and (7) above are used in the case where the radiation applied from the radiation source 1 is a cone beam. If the radiation is a parallel beam, Expression (8) below is used in place of Expression (5) above, Expression (9) below is used in place of Expression (6) above, and Expression (10) below is used in place of Expression (7) above.

$$Z_2 = \left(m + \frac{1}{2}\right) \frac{P_1^2}{\lambda} \tag{8}$$

$$Z_2 = \left(m + \frac{1}{2}\right) \frac{P_1^2}{4\lambda} \tag{9}$$

$$Z_2 = m \frac{P_1^2}{\lambda} \tag{10}$$

Further, as shown in FIG. 3, the members 22 of the first grating 2 are formed to have the thickness $h_1$ and the members 32 of the second grating 3 are formed to have the thickness $h_2$. If the thickness $h_1$ and the thickness $h_2$ are excessively thick, it is difficult for parts of the radiation that obliquely enter the first grating 2 and the second grating 3 to pass through the slits of the gratings, and this results in so-called vignetting, which narrows an effective field of view in the direction (the X-direction) orthogonal to the direction in which the members 22 and 32 extend. In view of ensuring the field of view, it is necessary to define the upper limits of the thicknesses $h_1$ and $h_2$. In order to ensure a length V of the effective field of view in the X-direction in the detection surface of the radiographic image detector 4, it is preferred to set the thicknesses $h_1$ and $h_2$ to satisfy Expressions (11) and (12) below:

$$h_1 \leq \frac{L}{V/2} d_1 \tag{11}$$

$$h_2 \leq \frac{L}{V/2} d_2 \tag{12}$$

where L is a distance from the focal spot of the radiation source 1 to the detection surface of the radiographic image detector 4 (see FIG. 2).

Further, in the radiographic phase-contrast imaging apparatus of this embodiment, the first grating 2 and the second grating 3 are inclined relative to each other, as shown in FIG. 6, so that the direction in which the self image G1 of the first grating 2 extends and the direction in which the second grating 3 extends are inclined relative to each other. In this embodiment, the first grating 2 and second grating 3 positioned in this manner provide the relationship as shown in FIG. 6 between a main pixel size Dx in the main scanning direction (X-direction in FIG. 5) and a sub-pixel size Dy in the sub-scanning direction of each pixel of the image signals detected by the radiographic image detector 4.

As described above, the main pixel size Dx is determined by the arrangement pitch of the transparent linear electrodes 46a and the light-shielding linear electrodes 46b of the radiographic image detector 4, and is set to be 50 μm in this embodiment. The sub-pixel size Dy is determined by the width of the linear reading light applied to the radiographic image detector 4 by the linear reading light source 50, and is set to be 10 μm in this embodiment.

In this embodiment, a plurality of fringe images are obtained, and a phase-contrast image is generated based on the fringe images. Assuming that the number of the obtained fringe images is M, the first grating 2 is inclined relative to the second grating 3 such that M sub-pixel sizes Dy correspond to an image resolution D in the sub-scanning direction of the phase-contrast image.

Specifically, as shown in FIG. 7, assuming that the pitch of the second grating 3 and the pitch of the self image G1 formed at the position of the second grating 3 by the first grating 2 are $P_1'$, a relative angle of rotation of the self image G1 of the first grating 2 relative to the second grating 3 in the X-Y plane is θ, and the image resolution in the sub-scanning direction of the phase-contrast image is D (=Dy×M), the phase of the self image G1 of the first grating 2 and the phase of the second grating 3 are offset from each other by n period(s) over the length of the image resolution D in the sub-scanning direction when the angle of rotation θ is set to satisfy Expression (13) below:

$$\theta = \arctan\left\{n \times \frac{P_1'}{D}\right\} \tag{13}$$

where n is an integer other than 0 and a multiple of M. It should be noted that FIG. 7 shows a case where M=5 and n=1.

Therefore, an image signal corresponding to a fraction of an intensity modulation for n period(s) of the self image G1 of the first grating 2 divided by M can be detected by each pixel having the size of Dx×Dy, which corresponds to a fraction of the image resolution D in the sub-scanning direction of the phase contrast image divided by M. Since n=1 in the example shown in FIG. 7, the phase of the self image G1 of the first grating 2 is offset from the phase of the second grating 3 by one period over the length of the image resolution D in the sub-scanning direction. Simply put, the range of the self image G1 of the first grating 2 for one period passing through the second grating 3 changes over the length of the image resolution D in the sub-scanning direction, thereby modulating the intensity of the self image G1 of the first grating 2 in the sub-scanning direction.

Then, since M=5, an image signal corresponding to a fraction of an intensity modulation for one period of the self image G1 of the first grating 2 divided by 5 can be detected by each pixel having the size of Dx×Dy. That is, image signals of five different fringe images can be detected by the pixels having the size of Dx×Dy. A method for obtaining the image signals of the five fringe images will be described in detail later.

It should be noted that, since Dx=50 μm, Dy=10 μm and M=5 in this embodiment, as described above, the image resolution Dx in the main-scanning direction of the phase contrast image is the same as the image resolution D=Dy×M in the sub-scanning direction. However, it is not necessary that the image resolution Dx in the main-scanning direction is the same as the image resolution D in the sub-scanning direction, and they may have any main/sub ratio.

Although M=5 in this embodiment, M may be 3 or more, other than 5. Although n=1 in the above description, n may be any integer other than 0. That is, if n is a negative integer, the direction of rotation is opposite from that in the above-described example. Further, n may be an integer other than ±1 to provide an intensity modulation for n periods. However, if n is a multiple of M, the pixels of one set of M pixels Dy in the sub-scanning direction have the same pattern formed by the phase of the self image G1 of the first grating 2 and the phase of the second grating 3, and they fail to provide the M different fringe images. Therefore, n is other than a multiple of M.

The rotational angle θ of the self image G1 of the first grating 2 relative to the second grating 3 may be provided, for example, by fixing a relative rotational angle between the radiographic image detector 4 and the second grating 3, and then rotating the first grating 2.

For example, assuming that $P_1'$=5 μm, D=50 μm and n=1 in Expression (13) above, a rotational angle θ is about 5.7°. Then, an actual rotational angle θ' of the self image G1 of the first grating 2 relative to the second grating 3 can be detected, for example, based on the pitch of a moire pattern formed between the self image G1 of the first grating and the second grating 3.

Specifically, as shown in FIG. 8, assuming that the actual rotational angle is θ' and an apparent pitch of the self image G1 in the X-direction after the rotation is, an observed moire pitch Pm is expressed as follows:

$$1/Pm = |1/P' - 1/P_1'|.$$

Therefore, the actual rotational angle θ' can be found by assigning:

$$P' = P_1'/\cos\theta'$$

to the above Expression. It should be noted that the moire pitch Pm may be found based on the image signals detected by the radiographic image detector 4.

Then, the actual rotational angle θ' is compared with the rotational angle θ determined according to Expression (13) above, and the rotational angle of the first grating 2 may be adjusted automatically or manually by an amount corresponding to the difference between the actual rotational angle θ' and the rotational angle θ.

The phase contrast image generation unit 5 generates a radiographic phase-contrast image based on the image signals of the M different fringe images, which are detected by the radiographic image detector 4. A method for generating the radiographic phase-contrast image will be described in detail later.

Next, operation of the radiographic phase-contrast imaging apparatus of this embodiment is described.

First, as shown in FIG. 1, after the subject 10 is placed between the radiation source 1 and the first grating 2, radiation is emitted from the radiation source 1. Then, the radiation is transmitted through the subject 10 and is applied onto the first grating 2. The radiation applied onto the first grating 2 is diffracted by the first grating 2 to form a Talbot interference image at a predetermined distance from the first grating 2 in the direction of the optical axis of the radiation.

This phenomenon is called the Talbot effect where, when the light wave passes through the first grating 2, the self image G1 of the first grating 2 is formed at a predetermined distance from the first grating 2. For example, in the case where the first grating 2 is a phase modulation grating that applies phase modulation of 90°, the self image G1 of the first grating 2 is formed at the distance $Z_2$ found by Expression (5) or (8) above (Expression (6) or (9) above in the case where the first grating 2 is a phase modulation grating that applies phase modulation of 180°, and Expression (7) or (10) above in the case where the first grating 2 is an intensity modulation grating). On the other hand, the wave front of the radiation entering the first grating 2 is distorted by the subject 10, and the self image G1 of the first grating 2 is deformed accordingly.

Subsequently, the radiation passes through the second grating 3. As a result, the deformed self image G1 of the first grating 2 is superimposed on the second grating 3 to be subjected to intensity modulation, and then is detected by the radiographic image detector 4 as an image signal which reflects the distortion of the wave front.

Now, an operation of detecting and reading an image carried out in the radiographic image detector 4 is described.

First, as shown at "A" in FIG. 9, in the state where a negative voltage is applied to the first electrode layer 41 of the radiographic image detector 4 by a high-voltage power supply 400, the radiation subjected to the intensity modulation by superimposing the self image G1 of the first grating 2 on the second grating 3 is applied to the radiographic image detector 4 from the first electrode layer 41 side thereof.

Then, the radiation applied to the radiographic image detector 4 is transmitted through the first electrode layer 41 to be applied to the recording photoconductive layer 42. The application of the radiation causes generation of electric charge pairs at the recording photoconductive layer 42. Among the generated electric charge pairs, positive electric charges are combined with negative electric charges charged in the first electrode layer 41 and disappear, and negative electric charges are stored as latent image electric charges in the electric charge storage area 43 formed at the interface between the recording photoconductive layer 42 and the electric charge transporting layer 44 (see "B" in FIG. 9).

Then, as shown in FIG. 10, in the state where the first electrode layer 41 is grounded, linear reading light L1 emitted from the linear reading light source 50 is applied to the radiographic image detector 4 from the second electrode layer 46 side thereof. The reading light L1 is transmitted through the transparent linear electrodes 46a to be applied to the reading photoconductive layer 45. Positive electric charges generated at the reading photoconductive layer 45 by the application of the reading light L1 pass through the electric charge transporting layer 44 and are combined with the latent image electric charges stored in the electric charge storing area 43. Negative electric charges generated at the reading photoconductive layer 45 by the application of the reading light L1 are combined with positive electric charges charged in the light-shielding linear electrodes 46b via a charge amplifier 200 connected to the transparent linear electrodes 46a.

When the negative electric charges generated at the reading photoconductive layer 45 are combined with the positive electric charges charged in the light-shielding linear electrodes 46b, electric currents flow to the charge amplifier 200, and the electric currents are integrated and detected as an image signal.

As the linear reading light source 50 is moved along the sub-scanning direction, the linear reading light L1 scans the radiographic image detector 4. Then, for each reading line exposed to the linear reading light L1, the image signal is sequentially detected by the above-described operation, and the detected image signal of each reading line is sequentially inputted to and stored in the phase contrast image generation unit 5.

In this manner, the entire surface of the radiographic image detector 4 is scanned by the reading light L1, and the image signals of a whole single frame are stored in the phase contrast image generation unit 5. Thereafter, the phase-contrast image generation unit 5 obtains the image signals of five different fringe images based on the stored image signals.

Figure 11:
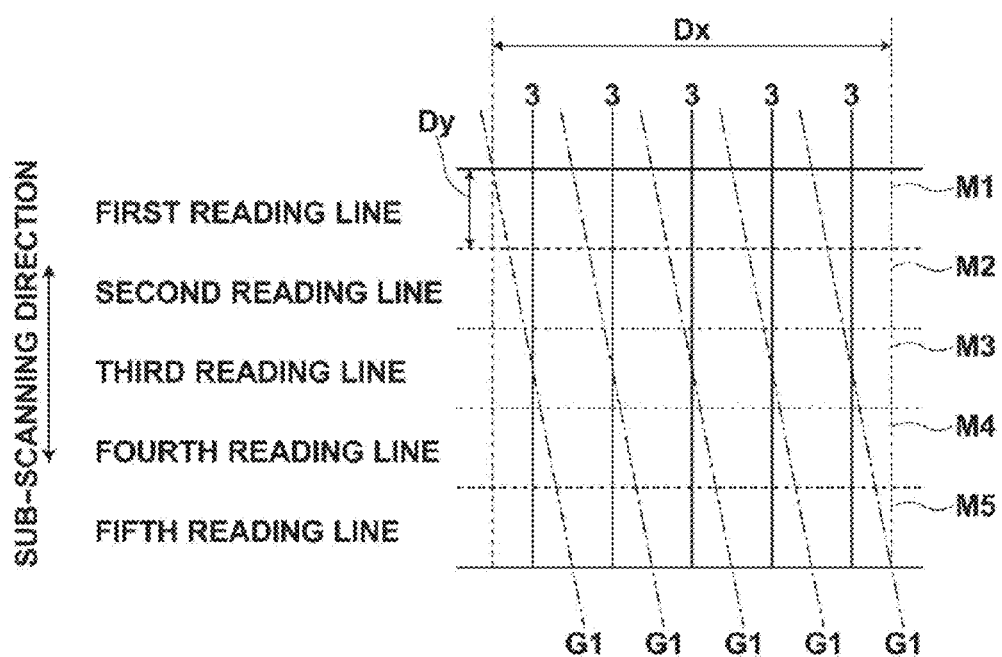
FIG. 11 is a diagram for explaining an operation to obtain a plurality of fringe images based on image signals read out from the radiographic image detector using the optical reading system.

Specifically, in this embodiment, where the self image G1 of the first grating 2 is inclined relative to the second grating 3, as shown in FIG. 7, such that the image resolution D in the sub-scanning direction of the phase contrast image is divided by 5 to detect image signals corresponding to fractions of the intensity modulation for one period of the self image G1 of the first grating 2 divided by 5, the image signal read out from the first reading line is obtained as a first fringe image signal M1, the image signal read out from the second reading line is obtained as a second fringe image signal M2, the image signal read out from the third reading line is obtained as a third fringe image signal M3, the image signal read out from the fourth reading line is obtained as a fourth fringe image signal M4 and the image signal read out from the fifth reading line is obtained as a fifth fringe image signal M5, as shown in FIG. 11. It should be noted that the width in the sub-scanning direction of each of the first to fifth reading lines shown in FIG. 11 corresponds to the sub-pixel size Dy shown in FIG. 7.

Although FIG. 11 only shows a reading range of Dx×(Dy× 5), the first to fifth fringe image signals are obtained in the same manner from the remaining reading ranges. Namely, as shown in FIG. 12, image signals of each pixel line group including pixel lines (reading lines) of every five pixels in the sub-scanning direction are obtained to obtain a single fringe image signal of a single frame. More specifically, the image signals of the pixel line group of the first reading lines are obtained to obtain the first fringe image signal of a single frame, the image signals of the pixel line group of the second reading lines are obtained to obtain the second fringe image signal of the single frame, the image signals of the pixel line group of the third reading lines are obtained to obtain the third fringe image signal of the single frame, the image signals of the pixel line group of the fourth reading lines are obtained to obtain the fourth fringe image signal of the single frame, and the image signals of the pixel line group of the fifth reading lines are obtained to obtain the fifth fringe image signal of the single frame.

In this manner, the first to fifth fringe image signals that are different from one another are obtained, and the phase contrast image generation unit 5 generates the phase contrast image based on the first to fifth fringe image signals.

Next, how the phase contrast image is generated at the phase contrast image generation unit 5 is described. First, the principle of the method for generating the phase contrast image in this embodiment is described.

FIG. 13 shows an example of one radiation path which is refracted depending on a phase shift distribution Φ(x) of the subject 10 with respect to the X-direction. The symbol X1 denotes a straight radiation path in a case where the subject 10 is not present. The radiation traveling along the path X1 passes through the first grating 2 and the second grating 3 and enters the radiographic image detector 4. The symbol X2 denotes a radiation path which is deflected due to refraction by the subject 10 in a case where the subject 10 is present. The radiation traveling along the path X2 passes through the first grating 2, and then is shielded by the second grating 3.

Assuming that a refractive index distribution of the subject 10 is n(x,z), and a direction in which the radiation travels is z, the phase shift distribution Φ(x) of the subject 10 is expressed by Expression (14) below (where the y-coordinate is omitted for simplifying the explanation):

$$\Phi(x) = \frac{2\pi}{\lambda} \int [1 - n(x, z)] dz \qquad (14)$$

The self image G1 formed by the first grating 2 at the position of the second grating 3 is displaced in the x-direction by an amount depending on the refraction angle φ of the refraction of radiation by the subject 10. The amount of displacement Δx is approximately expressed by Expression (15) below based on the fact that the refraction angle φ of the radiation is very small:

$$\Delta x \approx Z_2 \phi \qquad (15)$$

The refraction angle φ is expressed by Expression (16) below with using the wavelength λ of the radiation and the phase shift distribution Φ(x) of the subject 10:

$$\varphi = \frac{\lambda}{2\pi} \frac{\partial \Phi(x)}{\partial x} \qquad (16)$$

In this manner, the amount of displacement Δx of the self image G1 due to the refraction of radiation by the subject 10 is linked to the phase shift distribution Φ(x) of the subject 10. Then, the amount of displacement Δx is linked to an amount of phase shifting Ψ of the intensity-modulated signal of each pixel detected by the radiographic image detector 4 (i.e., an amount of phase shifting of the intensity-modulated signal of each pixel between the cases where the subject 10 is present and where the subject 10 is not present), as expressed by Expression (17) below:

$$\psi = \frac{2\pi}{P_2} \Delta x = \frac{2\pi}{P_2} Z_2 \varphi \qquad (17)$$

Therefore, by finding the amount of phase shifting Ψ of the intensity-modulated signal of each pixel, the refraction angle φ is found from Expression (17) above, and a differential of the phase shift distribution Φ(x) is found using Expression (16) above. By integrating the differentials with respect to x, the phase shift distribution Φ(x) of the subject 10, i.e., the phase contrast image of the subject 10 can be generated. In this embodiment, the amount of phase shifting Ψ is calculated using the fringe scanning method based on the above-described first to fifth fringe image signals.

Since the image resolution D in the sub-scanning direction of the phase-contrast image is divided by 5 in this embodiment, five different fringe image signals including the first to fifth fringe image signals are obtained for each pixel of the phase-contrast image. Now, how the amount of phase shifting Ψ of the intensity-modulated signal of each pixel is calculated from the five fringe image signals including the first to fifth fringe image signals is described. In the following description, the number of the fringe image signals is not limited to five, and a method for calculating the amount of phase shifting Ψ based on M fringe image signals is described.

First, a pixel signal Ik (x) of each pixel arranged in the main scanning direction of the radiographic image detector 4 at a k-th reading line, as shown in FIG. 11, is expressed by Expression (18) below:

$$I_k(x) = A_0 + \sum_{n>0} A_n \exp\left[2\pi i \frac{n}{P_2}\left\{Z_2\varphi(x) + \frac{kP_2}{M}\right\}\right] \quad (18)$$

where x is a coordinate of the pixel with respect to the x-direction, $A_0$ is an intensity of the incident radiation, and $A_n$ is a value corresponding to the contrast of the intensity-modulated signal (where n is a positive integer). Further, φ(x) represents the refraction angle φ as a function of the coordinate x of each pixel of the radiographic image detector 4.

Then, using the relational expression of Expression (19) below, the refraction angle φ(x) is expressed as Expression (20) below:

$$\sum_{k=1}^{M} \exp\left(-2\pi i \frac{k}{M}\right) = 0 \quad (19)$$

$$\varphi(x) = \frac{p_2}{2\pi Z_2} \arg\left[\sum_{k=1}^{M} I_k(x)\exp\left(-2\pi i \frac{k}{M}\right)\right] \quad (20)$$

where "arg[ ]" means extraction of an argument, and corresponds to the amount of phase shifting Ψ of the intensity-modulated signal at each pixel of the phase-contrast image. Therefore, the refraction angle φ(x) is found by calculating, based on Expression (20), the amount of phase shifting Ψ of the intensity-modulated signal of each pixel of the phase contrast image from the pixel signals of the M fringe image signals obtained for each pixel of the phase-contrast image.

Figure 14:
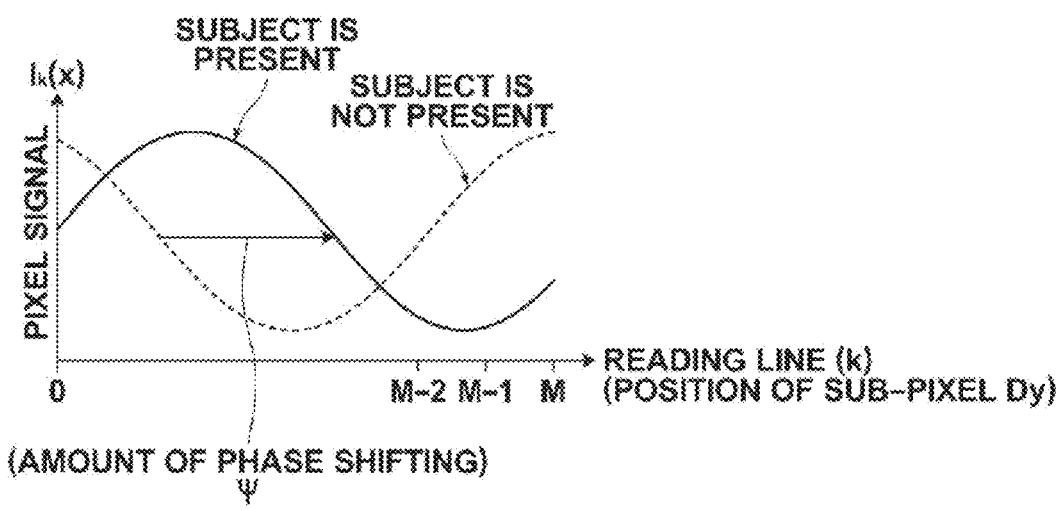
FIG. 14 is a diagram for explaining a method for generating a phase-contrast image.

Specifically, as shown in FIG. 14, M pixel signals obtained for M sub-pixels Dy, which form each pixel of the phase-contrast image, periodically vary with the period of M×sub-pixel Dy relative to the position of the reading line (the position of the sub-pixel Dy). Therefore, the phase shift distribution Φ(x) of the subject 10, i.e., the phase-contrast image of the subject 10 is generated by fitting the signal line of the M sub-pixels Dy with a sinusoidal wave, for example, obtaining amounts of phase shifting Ψ between the fitting curves when there is a subject and when there is no subject, calculating differentials of the phase shift distribution Φ(x) according to Expressions (16) and (17) above, and integrating the differentials with respect to x.

It should be noted that, as the fitting curve, typically a sinusoidal wave may be used, as described above; however, a square wave form or a triangular wave form may be used.

Although the y-coordinate of each pixel of the phase-contrast image with respect to the y-direction is not taken into account in the above description, a two-dimensional phase shift distribution Φ(x,y) can be obtained by performing calculations similar to those described above for each y-coordinate to obtain a two-dimensional distribution of refraction angles φ(x,y), and integrating the two-dimensional distribution of refraction angles φ(x,y) along the x-axis.

Alternatively, the phase contrast image may be generated by integrating a two-dimensional distribution of amounts of phase shifting Ψ(x,y) along the x-axis, in place of the two-dimensional distribution of refraction angles φ(x,y).

The two-dimensional distribution of refraction angles φ(x,y) and the two-dimensional distribution of amounts of phase shifting Ψ(x,y) correspond to the differential values of the phase shift distribution Φ(x,y), and thus are called "differential phase image". The differential phase image may be generated as the phase contrast image.

Further, although the direction in which the second grating 3 extends is parallel to the Y-direction and the direction in which the self image G1 of the first grating 2 extends is inclined relative to the Y-direction by θ, as shown in FIG. 6, in the above-described first embodiment, the direction in which the self image G1 of the first grating 2 extends may be parallel to the Y-direction, and the direction in which the second grating 3 extends may be inclined relative to the Y-direction by θ.

Still further, the relative angle of rotation θ in the X-Y plane between the self image G1 of the first grating 2 and the second grating 3 may be expressed by Expression (21) below, in place of Expression (13), based on a relationship between a sub-pixel size Dsub and a period T of the moire pattern formed by the self image G1 of the first grating 2 and the second grating 3. In Expression (21) below, $Z_1$ is a distance from the focal spot of the radiation source 1 to the first grating 2, $Z_2$ is a distance from the first grating 2 to the second grating 3, L is a distance from the focal spot of the radiation source 1 to the radiographic image detector 4, and $P_1'$ is an arrangement pitch of the self image G1 of the first grating 2 formed at the position of the second grating 3.

It should be noted that, in the description of Expression (13) above, the sub-pixel size is called "Dy" because the arrangement direction of the five pixels for obtaining the image signals forming the different fringe images is the Y-direction. However, as described in detail later, the arrangement direction of the five pixels is not limited to the Y-direction, and may be in any other direction. Therefore, in the description of Expression (21), the sub-pixel size is called "Dsub". "Dy" and "Dsub" are the same in that they mean the sub-pixel size. Therefore, the image resolution D in Expression (13) may be expressed by "the number of fringe images M × sub-pixel size Dsub", and the direction of this sub-pixel size is not limited to the Y-direction.

$$T = \frac{L}{Z_1 + Z_2} \times \frac{P_1'}{\tan\theta} \geq 3Dsub \quad (21)$$

Further, at this time, a relationship to be satisfied by the arrangement pitch $P_1$ of the self image G1 of the first grating 2, the grating pitch $P_1$ of the first grating 2 and the grating pitch $P_2$ of the second grating 3 is expressed by Expression (22) below if the first grating 2 is a phase modulation grating that applies phase modulation of 90° or an amplitude modulation grating, or is expressed by Expression (23) below if the first grating 2 is a phase modulation grating that applies phase modulation of 180°.

$$P_2 = P_1' = \frac{Z_1 + Z_2}{Z_1} P_1 \quad (22)$$

$$P_2 = P_1' = \frac{Z_1 + Z_2}{Z_1} \frac{P_1}{2} \quad (23)$$

Figure 15:
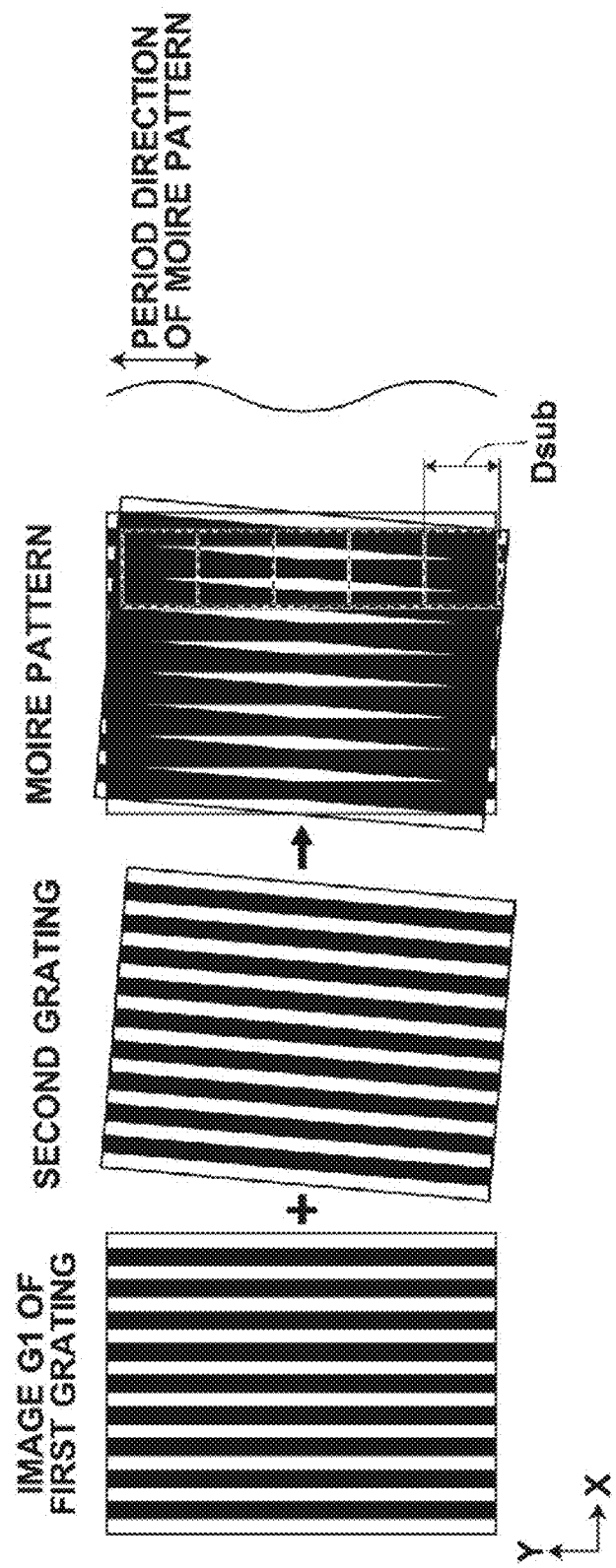
FIG. 15 is a diagram illustrating one example of a relationship between a moire pattern formed by the self image of the first grating and the second grating superimposed one another and sub-pixels read out as image signals forming different fringe images.

Then, when the self image G1 of the first grating 2 and the second grating 3 are positioned as shown in FIG. 15, a moire pattern having the period direction thereof in the Y-direction, as shown at the rightmost part in FIG. 15, is formed. Then, by obtaining image signals of pixels arranged parallel to the period direction of the moire pattern, as shown by the rectangles in dashed lines in FIG. 15, for example, the image signals forming five different fringe images can be obtained, similarly to the above-described first embodiment.

The first embodiment of the radiographic phase-contrast imaging apparatus of the invention has been described.

Next, a radiographic phase-contrast imaging apparatus according to a second embodiment of the invention is described. With respect to the radiographic phase-contrast imaging apparatus of the above-described first embodiment, any one of Expressions (5) to (10) above is satisfied depending on the type of the first grating 2 and the spread angle of the radiation emitted from the radiation source 1, so that the distance $Z_2$ from the first grating 2 to the second grating 3 becomes a Talbot interference distance. In the radiographic phase-contrast imaging apparatus of the second embodiment, the most part of the radiation entering the first grating 2 is not diffracted, and the radiation is projected. In this case, similar projection images passed through the first grating 2 are obtained at positions behind the first grating 2, and this allows setting the distance $Z_2$ from the first grating 2 to the second grating 3 irrespectively of the Talbot interference distance.

Specifically, in the radiographic phase-contrast imaging apparatus of the second embodiment, both the first grating 2 and the second grating 3 are formed as absorption type (amplitude modulation type) gratings, and are adapted to geometrically project the radiation passed through the slits irrespectively of the Talbot interference effect. In more detail, values of the interval $d_1$ of the first grating 2 and the interval $d_2$ of the second grating 3 are set to be sufficiently greater than the effective wavelength of the radiation applied from the radiation source 1, so that the most part of the applied radiation forms the self image G1 of the first grating 2 behind the first grating 2 without being diffracted by the slits. For example, in the case where tungsten is used as the target of the radiation source and the tube voltage is 50 kV, the effective wavelength of the radiation is about 0.4 Å. In this case, by setting the interval $d_1$ of the first grating 2 and the interval $d_2$ of the second grating 3 to be around 1 μm to 10 μm, the effect of diffraction on the radiographic image formed by the radiation transmitted through the slits is negligible, and the self image G1 of the first grating 2 is geometrically projected behind the first grating 2.

It should be noted that the relationship between the grating pitch $P_1$ of the first grating 2 and the grating pitch $P_2$ of the second grating 3 and the relationship between the interval $d_1$ of the first grating 2 and the interval $d_2$ of the second grating 3 are the same as those expressed by Expressions (1) and (2) in the first embodiment. The relationship of relative inclination between the self image G1 of the first grating 2 and the second grating 3 is also the same as that expressed by Expression (13) in the above-described first embodiment.

In the second embodiment, the distance $Z_2$ between the first grating 2 and the second grating 3 can be set to be a value that is shorter than the minimum Talbot interference distance found by Expression (7) above where m=1. That is, the value of the distance $Z_2$ is set to be a value within a range where Expression (24) below is satisfied:

$$Z_2 < \frac{P_1 P_2}{\lambda} \quad (24)$$

In order to generate a high-contrast periodic pattern image, it is preferred that the members 22 of the first grating 2 and the members 32 of the second grating 3 completely shield (absorb) the radiation. However, even when the above-described material (such as gold or platinum) having high radiation absorption is used, no small part of the radiation is transmitted without being absorbed. Therefore, in order to increase the radiation shielding ability, the thicknesses $h_1$ and $h_2$ of the members 22 and 32 may be made as thick as possible. It is preferred that the members 22 and 32 shield 90% or more of the radiation applied thereto. The materials forming the members 22 and 32 and the thicknesses $h_1$ and $h_2$ of the members 22 and 32 are set depending on the energy of radiation to be applied thereto. For example, in the case where tungsten is used as the target of the radiation source and the tube voltage is 50 kV, the thicknesses $h_1$ and $h_2$ is preferably 100 μm more when the members 22 and 32 are made of gold (Au).

However, similarly to the above-described first embodiment, there is the problem of so-called vignetting of the radiation in the second embodiment. Therefore, it is preferable to limit the thicknesses $h_1$ and $h_2$ of the members 22 of the first grating 2 and the members 32 of the second grating 3.

Also in the radiographic phase-contrast imaging apparatus of the second embodiment, radiation is emitted from the radiation source 1 after the subject 10 is placed between the radiation source 1 and the first grating 2, as shown in FIG. 1. Then, the radiation is transmitted through the subject 10 and is applied onto the first grating 2.

Then, a projection image formed by the radiation passed through the first grating 2 passes through the second grating 3. As a result, the projection image is subjected to intensity modulation by being superimposed on the second grating 3, and is detected by the radiographic image detector 4 as an image signal.

Then, similarly to the above-described first embodiment, the image signal detected by the radiographic image detector 4 is read out, and the image signals of a whole single frame are stored in the phase contrast image generation unit 5. Thereafter, the phase-contrast image generation unit 5 obtains the image signals of five different fringe images based on the stored image signals, similarly to the above-described first embodiment.

The operation for generating the phase-contrast image at the phase-contrast image generation unit 5 is the same as that in the above-described first embodiment.

According to the radiographic phase-contrast imaging apparatus of the second embodiment, the distance $Z_2$ between the first grating 2 and the second grating 3 can be made shorter than the Talbot interference distance. In this case, the imaging apparatus can be made thinner than the radiographic phase-contrast imaging apparatus of the first embodiment, which has to ensure a certain Talbot interference distance.

The second embodiment of the radiographic phase-contrast imaging apparatus of the invention has been described.

In the case where the distance from the radiation source 1 to the radiographic image detector 4 is a typical distance (1 m to 2 m) set in the imaging chamber of hospitals, and the focal spot size of the radiation source 1 is, for example, a typical size around 0.1 mm to 1 mm in the above-described radiographic phase-contrast imaging apparatuses of the first and second embodiments, the self image G1 formed by the Talbot interference of the first grating 2 or the projection of the first grating 2 may be blurred, and this may result in lower image quality of the phase-contrast image.

To address this problem, when the radiation source 1 with the focal spot size as described above is used, it is contemplated to provide a pin hole immediately downstream the focal spot of the radiation source 1 to reduce the effective focal spot size. However, if the opening area of the pin hole is reduced to reduce the effective focal spot size, intensity of the radiation is decreased.

Therefore, in place of providing a pin hole as described above, a multislit may be provided immediately downstream the focal spot of the radiation source 1 in the radiographic phase-contrast imaging apparatuses of the first and second embodiments.

The multislit is an absorption type grating having the same structure as the first and second gratings 2 and 3 of the second embodiment, and includes a plurality of periodically-arranged radiation shielding areas extending in a predetermined direction. The arrangement direction of the radiation shielding areas of the multislit is preferably the same as the arrangement direction of either one of the members 22 of the first grating 2 or the members 32 of the second grating 3; however, this is not essential in view of obtaining a phase-contrast image. In this embodiment, as an example of the most preferred mode, the arrangement direction of the radiation shielding areas of the multislit is the same as the arrangement direction (X-direction) of the members 22 of the first grating 2.

That is, in this case, the multislit partially shields the radiation emitted from the focal spot of the radiation source 1, thereby reducing the effective focal spot size with respect to the X-direction and forming a number of micro focus light sources divided in the X-direction in a pseudo manner.

It is necessary to set a grating pitch $P_3$ of this multislit such that Expression (25) below is satisfied:

$$P_3 = \frac{Z_3}{Z_2} P_1' \qquad (25)$$

where $Z_3$ is a distance from the multislit to the first grating 2, and $P_1'$ is an arrangement pitch of the self image G1 of the first grating 2 at the position of the second grating 3.

Further, even when the multislit is provided, the reference point of the magnification factor of the self image G1 of the first grating 2 is the position of the focal spot of the radiation source. Therefore, the relationships to be satisfied by the grating pitch $P_2$ and the interval $d_2$ of the second grating are the same as those in the above-described first and second embodiments. That is, in the case where the first grating 2 is a phase modulation grating that applies phase modulation of 90° or an amplitude modulation grating, the grating pitch $P_2$ and the interval $d_2$ of the second grating 3 are determined such that the relationships expressed by Expressions (26) and (27) below are satisfied, respectively:

$$P_2 = \frac{Z_1 + Z_2}{Z_1} P_1 \qquad (26)$$

$$d_2 = \frac{Z_1 + Z_2}{Z_1} d_1 \qquad (27)$$

Alternatively, in the case where the first grating 2 is a phase modulation grating that applies phase modulation of 180°, the grating pitch $P_2$ and the interval $d_2$ of the second grating 3 are determined such that the relationships expressed by Expressions (28) and (29) below are satisfied, respectively:

$$P_2 = \frac{Z_1 + Z_2}{2Z_1} P_1 \qquad (28)$$

$$d_2 = \frac{Z_1 + Z_2}{2Z_1} d_1 \qquad (29)$$

Further, in order to ensure a length V of effective field of view in the X-direction in the detection surface of the radiographic image detector 4, it is preferable to determine the thickness $h_1$ of the members 22 of the first grating 2 and the thickness $h_2$ of the members of the second grating 3 such that the Expressions (30) and (31) below are satisfied:

$$h_1 \leq \frac{L}{V/2} d_1 \qquad (11)$$

$$h_2 \leq \frac{L}{V/2} d_2 \qquad (12)$$

where L is a distance from the focal spot of the radiation source 1 to the radiographic image detector 4.

It should be noted that Expression (25) above is a geometrical condition for a plurality of self images G1, which are formed by radiation rays emitted from the microfocus light sources dispersed in a pseudo manner by the multislit due to the Talbot interference or projection of the first grating 2, to be superimposed one another at the position of the second grating 3 with being offset from one another by one period of the pitch of the self image G1 of the first grating 2. In this manner, the self images G1 of the first grating 2, which are formed by the microfocus light sources formed by the multislit due to the Talbot interference or the projection image, are regularly superimposed one another, thereby avoiding decrease of the intensity of the radiation and providing a phase-contrast image with improved image quality.

Further, in the case where the multislit is used in the radiographic phase-contrast imaging apparatuses of the first and second embodiments, as described above, a relationship among the relative angle of rotation θ between the self images G1 of the first grating 2 and the second grating 3, the period T of the moire pattern formed by the self images G1 of the first grating 2 and the second grating 3, and the sub-pixel size Dsub is expressed by Expression (32) below, which is similar to Expression (21) above:

$$T = \frac{L}{Z_1 + Z_2} \times \frac{P_1'}{\tan\theta} \geq 3Dsub \qquad (32)$$

In Expression (32), $Z_1$ is a distance from the focal spot of the radiation source 1 to the first grating 2, $Z_2$ is a distance between the first grating 2 and the second grating 3, and L is a distance from the focal spot of the radiation source 1 to the radiographic image detector 4.

In the above-described first and second embodiments, the first grating 2 and the second grating 3 are inclined relative to each other, so that the direction in which the self image G1 of the first grating 2 extends and the direction in which the second grating 3 extends are inclined relative to each other. Further, in the case where the multislit is used, the arrangement direction of the radiation shielding areas of the multislit is the same as the arrangement direction of the members 22 of the first grating 2. However, the invention is not limited to the above-described embodiments. For example, the first grating 2 and the second grating 3 may be positioned such that the direction in which the first grating 2 extend is parallel to the direction in which the second grating 3 extend, and the direction in which the radiation shielding areas of the multislit extend may be inclined relative to the direction in which the first and second gratings 2 and 3 extend. This is because that, even in this arrangement, the direction in which the self image G1 of the first grating 2 extends and the direction in which the second grating extends are inclined relative to each other and a moire pattern is formed.

Further, while the self image G1 of the first grating 2 and the second grating 3 are inclined relative to each other in the above-described radiographic phase-contrast imaging apparatus of the first and second embodiments, the self image G1 of the first grating 2 and the second grating 3 are not necessarily inclined relative to each other. For example, the self image G1 of the first grating 2 may be parallel to the second grating 3, and the second grating 3 having an arrangement pitch that is different from the arrangement pitch of the self image G1 of the first grating 2 may be used.

Figure 16:
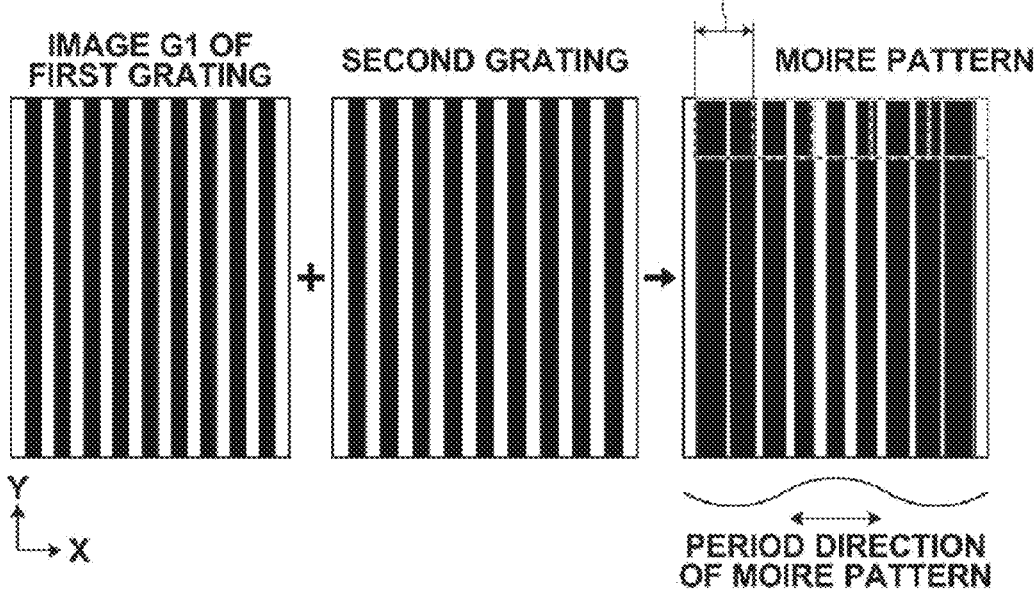
FIG. 16 is a diagram illustrating one example of a relationship between a moire pattern formed by the self image of the first grating and the second grating superimposed one another and sub-pixels read out as image signals forming different fringe images in a case where a direction in which the self image of the first grating extends is parallel to a direction in which the second grating extends and the second grating has a pitch different from a pitch of the self image of the first grating.

In the case where the first grating 2 and the second grating 3 positioned as described above are used, a moire pattern in the Y-direction, i.e., a moire pattern having the period direction thereof in the X-direction, is formed, as shown in FIG. 16. Therefore, by obtaining image signals of five pixels arranged parallel to the period direction of the moire pattern, as shown by the rectangles in dashed lines in FIG. 16, for example, the image signals forming five different fringe images can be obtained similarly to the above-described first embodiment.

As described above, in the case where the second grating 3 having an arrangement pitch that is different from the arrangement pitch of the self image G1 of the first grating 2 is used, the arrangement pitch $P_1'$ of the self image G1 of the first grating 2, the arrangement pitch $P_2$ of the second grating 3, the period T of the moire pattern, and the sub-pixel size Dsub are determined to satisfy Expression (33) below:

$$T = \frac{L}{Z_1 + Z_2} \times \left| \frac{P_1' P_2}{P_1' - P_2} \right| \geq 3Dsub \quad (33)$$

In this case, if the first grating 2 is a phase modulation grating that applies phase modulation of 90° or an amplitude modulation grating, the arrangement pitch $P_1'$ of the self image G1 of the first grating 2 is determined to satisfy Expression (34) below, or if the first grating 2 is a phase modulation grating that applies phase modulation of 180°, the arrangement pitch $P_1'$ of the self image G1 of the first grating 2 is determined to satisfy Expression (35) below:

$$P_1' = \frac{Z_1 + Z_2}{Z_1} P_1 \quad (34)$$

$$P_1' = \frac{Z_1 + Z_2}{Z_1} \frac{P_1}{2} \quad (35)$$

Also, in the embodiments where the radiographic phase-contrast imaging apparatuses of the above-described first and second embodiments are provided with the multislit, the second grating 3 having an arrangement pitch different from the arrangement pitch of the self image G1 of the first grating 2 may be used, as described above. In the case where the multislit is used, the arrangement pitch $P_1'$ of the self image G1 of the first grating 2, the arrangement pitch $P_2$ of the second grating 3, the period T of the moire pattern and the sub-pixel size Dsub are determined to satisfy Expression (36) below:

$$T = \frac{L}{Z_1 + Z_2} \times \left| \frac{P_1' P_2}{P_1' - P_2} \right| \geq 3Dsub \quad (36)$$

where $Z_1$ is a distance from the focal spot of the radiation source 1 to the first grating 2, $Z_2$ is a distance between the first grating 2 and the second grating 3, and L is a distance from the focal spot of the radiation source 1 to the radiographic image detector 4.

In this case, the relational expression to be satisfied by the arrangement pitch $P_1'$ of the self image G1 of the first grating 2 is the same as Expression (34) or (35) above, and it is necessary that Expression (25) above is further satisfied.

Figure 17:
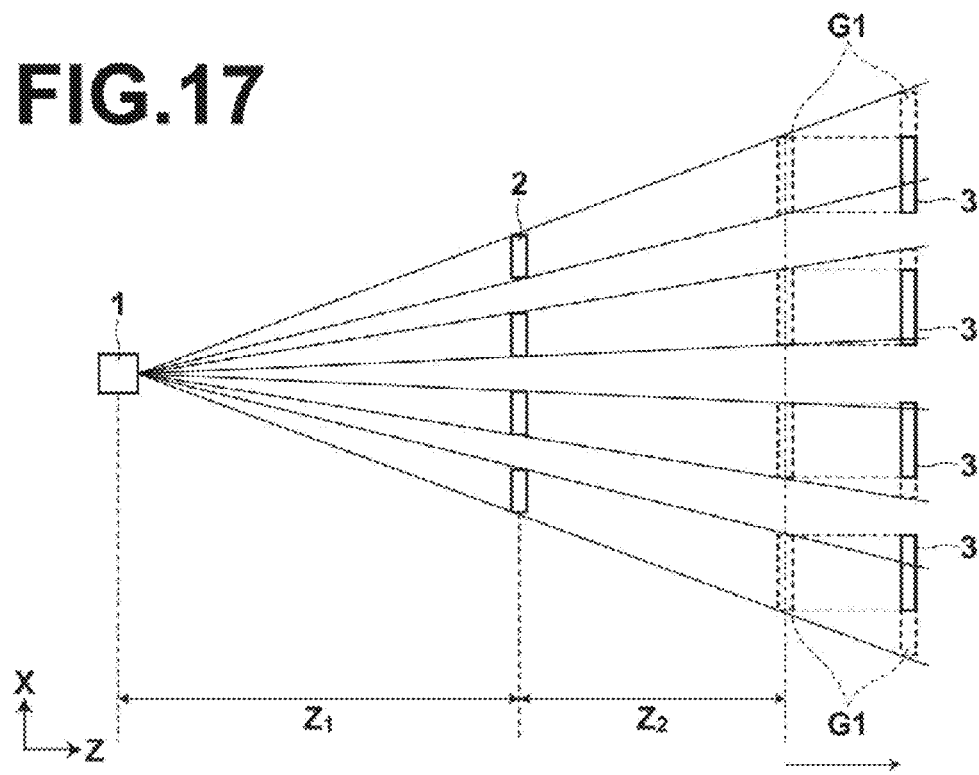
FIG. 17 is a diagram illustrating one example of a case where the second grating is provided with a pitch different from the pitch of the self image of the first grating at the position of the second grating by moving the second grating away from the position where the second grating has the same pitch as the pitch of the self image of the first grating.

Further, while the arrangement pitch of the self image G1 of the first grating 2 is different from the arrangement pitch of the second grating 3 in the above description, this is not intended to limit the invention. For example, if the radiation emitted from the radiation source 1 is a cone beam, the second grating 3 which has an arrangement pitch that becomes the same as the arrangement pitch of the self image G1 of the first grating 2 at the position of $Z_2$ may be used, as shown in FIG. 17, and this second grating 3 may be moved and placed at a position where $Z_2$ is increased (or at a position where $Z_2$ is decreased (not shown)), so that the arrangement pitch of the magnified self image G1 of the first grating 3 becomes different from the arrangement pitch of the second grating 3. Also in this arrangement, it is necessary that Expressions (33) and (34) or (35) above is satisfied, and if the multislit is used, it is necessary that Expression (36), in place of Expression (33) above, and Expression (25) above are further satisfied. It should be noted that, in these expressions, $P_1'$ in this arrangement is the arrangement pitch $P_1'$ of the self image G1 of the first grating 2 at the position of the moved second grating 3, and $Z_2$ in this arrangement is the distance between the first grating 2 and the moved second grating 3.

Further, the second grating 3 having an arrangement pitch different from the arrangement pitch of the self image G1 of the first grating 2 may be used, as described above. Still further, the self image G1 of the first grating 2 and the second grating 3 may be inclined relative to each other, as described above.

Figure 18:
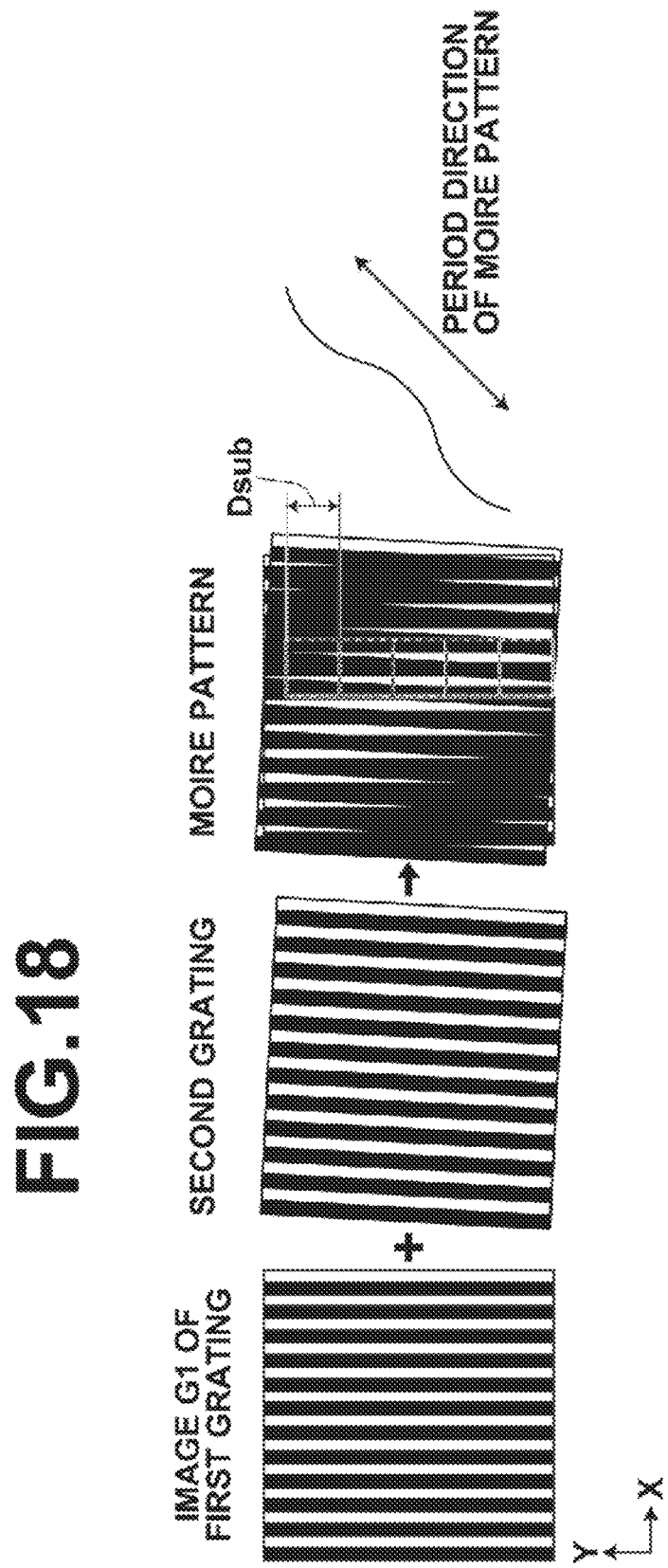
FIG. 18 is a diagram illustrating one example of a relationship between a moire pattern formed by the self image of the first grating and the second grating superimposed one another and sub-pixels read out as image signals forming different fringe images in a case where the direction in which the self image of the first grating extends is inclined relative to the direction in which the second grating extends and the second grating has a pitch different from the pitch of the self image of the first grating.

With this arrangement, a moire pattern having the period in an oblique direction (i.e., a direction which is not parallel to either of X-direction and Y-direction), as shown in FIG. 18, can be formed. Therefore, by obtaining image signals of five pixels arranged parallel to the Y-direction, as shown by the rectangles in dashed lines in FIG. 18, for example, the image signals forming five different fringe images can be obtained similarly to the above-described first embodiment.

Figure 19:
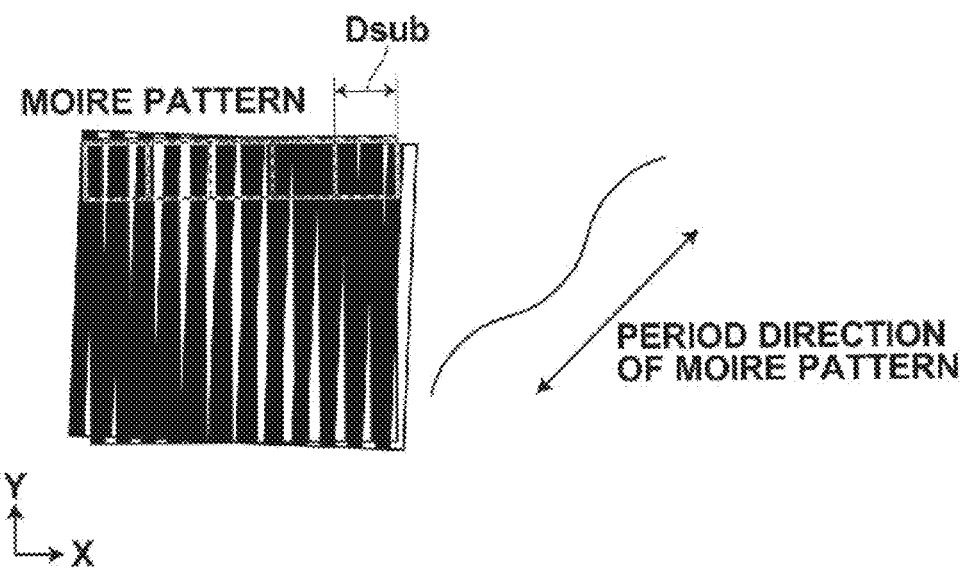
FIG. 19 is a diagram illustrating another example of a relationship between a moire pattern formed by the self image of the first grating and the second grating superimposed one another and sub-pixels read out as image signals forming different fringe images in a case where the direction in which the self image of the first grating extends is inclined relative to the direction in which the second grating extends and the second grating has a pitch different from the pitch of the self image of the first grating.

It should be noted that, while the image signals of the five pixels arranged parallel to the Y-direction are obtained in the example shown in FIG. 18, this is not intended to limit the invention. As shown in FIG. 19, image signals of five pixels arranged parallel to the X-direction may be obtained. In short, as long as image signals of pixels arranged along a direction parallel to or a direction intersecting a period direction of the moire pattern other than a direction orthogonal to the period direction of the moire pattern are obtained, the pixels may be arranged in any direction.

Figure 20:
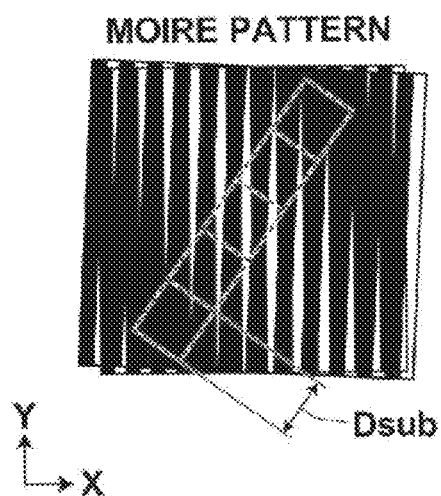
FIG. 20 is a diagram illustrating yet another example of a relationship between a moire pattern formed by the self image of the first grating and the second grating superimposed one another and sub-pixels read out as image signals forming different fringe images in a case where the direction in which the self image of the first grating extends is inclined relative to the direction in which the second grating extends and the second grating has a pitch different from the pitch of the self image of the first grating.

While the case where the period direction of the self image G1 of the first grating 2 or the period direction of the second grating 3 is the same as either one of the directions orthogonal to the direction in which the pixels of the radiographic image detector 4 are arranged has been described above, this is not intended to limit the invention. As shown in FIG. 20, a relative angle between the period direction of the first grating 2 and the arrangement direction of the pixels of the radiographic image detector 4 and a relative angle between the period direction of the second grating 3 and the arrangement direction of the pixels of the radiographic image detector 4 may be different from each other so that the image signals of five pixels arranged along an oblique direction (i.e., a direction which is not parallel to either of the X-direction and the Y-direction) can be obtained.

In short, as long as image signals of pixels arranged along a predetermined direction, which is a direction parallel to or a direction intersecting a period direction of the moire pattern other than a direction orthogonal to the period direction of the moire pattern are obtained as the image signals forming the different fringe images, the period directions of the first and second gratings 2 and 3 and the arrangement direction of the pixels of the radiographic image detector 4 may have any relationships therebetween. Therefore, the sub-pixel size in Expressions (13), (21), (32), (33) and (36) above is a pixel size in a predetermined direction, as described above, which is not limited to the pixel size in the Y-direction.

Figure 21:
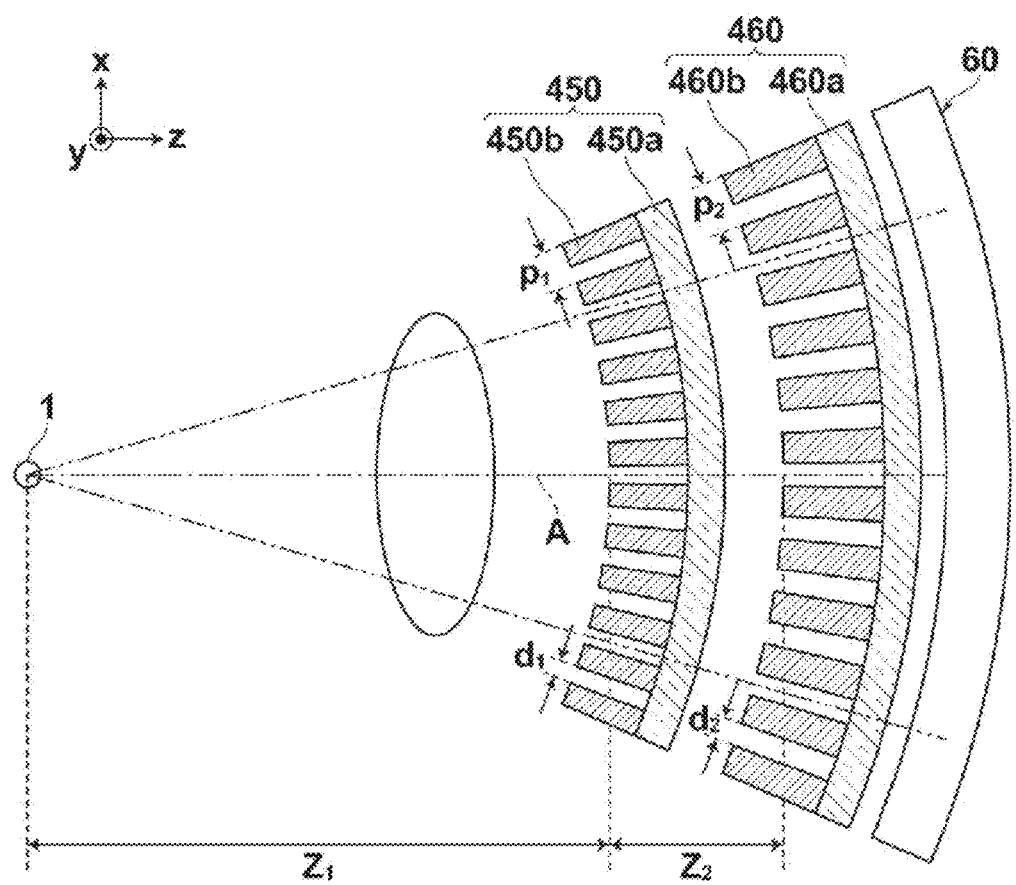
FIG. 21 is a diagram illustrating one example of a first grating and a second grating each having a concave curved grating surface.

Further, while the directions in which the members 22 and 32 of the first and second gratings 2 and 3 are periodically arranged are described to be linear (i.e., the grating surface is planar) in the above description, it is more preferable to use a first grating 450 and a second grating 460, each of which has a concave curved grating surface, as shown in FIG. 21, in place of the first and second gratings 2 and 3 in all the above-described embodiments.

The first grating 450 has a plurality of members 450b periodically arranged at a predetermined pitch $P_1$ on the surface of a curved substrate 450a, which transmits radiation. Similarly to the first and second embodiments, the members 450b extend linearly in the Y-direction. The grating surface of the first grating 450 has a shape corresponding to a part of a cylindrical shape with the center axis thereof being a straight line which crosses the focal spot of the radiation source 1 and extends in the direction in which the members 450b extend. Similarly, the second grating 460 has a plurality of members 460b periodically arranged at a predetermined pitch $P_2$ on the surface of a curved substrate 460a, which transmits radiation. The members 460b extend linearly in the Y-direction. The grating surface of the second grating 460 has a shape corresponding to a part of a cylindrical shape with the center axis thereof being a straight line which crosses the focal spot of the radiation source 1 and extends in the direction in which the members 460b extend.

Assuming that the distance from the focal spot of the radiation source 1 to the first grating 450 is $Z_1$, and the distance from the first grating 450 to the second grating 460 is $Z_2$, the grating pitches $P_1$ and $P_2$ are determined to satisfy the relationship expressed by Expression (1) or (3) above. An opening width $d_1$ of slits of the first grating 450 and an opening width $d_2$ of slits of the second grating 460 are determined to satisfy the relationship expressed by Expression (2) or (4) above.

By providing the first and second gratings 450 and 460 having the cylindrical grating surfaces in this manner, the radiation emitted from the focal spot of the radiation source 1 enters the grating surfaces orthogonally to any point on the grating surfaces when there is no subject 10. Therefore, there is no upper limit of the thicknesses of the members 450b and the members 460b, and it is not necessary to take Expressions (11) and (12) above into account.

Further, in the above-described embodiment where the multislit is provided, it is preferable that the multislit has the same structure as that of the second grating 460.

It should be noted that each of the first and second gratings 450 and 460 may be formed by joining a plurality of small planar gratings. Alternatively, the substrates 450a and 460a of the first and second gratings 450 and 460 may be flexible.

Further, a flexible radiographic image detector 60, a SID (Source to Image Distance) changing mechanism for changing the distance (SID) from the focal spot of the radiation source 1 to the detection surface of the radiographic image detector 60, and a curvature adjusting mechanism for changing the curvature depending on the SID may be provided. For example, the SID changing mechanism and the curvature adjusting mechanism may be controlled based on a SID value inputted from a predetermined input device to adjust the position of the radiation source 1 or the radiographic image detector 60 and to change the curvature of the radiographic image detector 60 so that the incident angle of the radiation to the detection surface becomes almost normal to the detection surface.

Further, in the case where the distances $Z_1$ and $Z_2$ change when the SID is changed by the SID changing mechanism, a mechanism for changing the curvatures of the first and second gratings 450 and 460 depending on the distances $Z_1$ and $Z_2$ may be provided. However, if the changes of the distances $Z_1$ and $Z_2$ are large, the grating pitches $P_1$ and $P_2$ cannot accommodate to the changes even when the curvatures of the first and second gratings 450 and 460 are changed. Therefore, the first and second gratings 450 and 460 may be replaceable with those having appropriate curvatures and grating pitches $P_1$ and $P_2$.

While the first and second gratings 450 and 460 are formed by arranging the members 450b and 460b in the direction orthogonal to the direction of curve of the substrates 450a and 460a, thereby eliminating the limitation on the thicknesses of the members 450b and 460b in the above description, the members 450b and 460b may be arranged along the direction of curve of the substrates 450a and 460a.

Further, while the radiographic image detector using the so-called optical reading system, where image signals are read out by scanning with the linear reading light emitted from the linear reading light source 50, is used as the radiographic image detector 4 in the above description, this is not intended to limit the invention. For example, a radiographic image detector using TFT switches, where a number of TFT switches are two-dimensionally arranged and image signals are read out by turning on and off the TFT switches, as taught in Japanese Unexamined Patent Publication No. 2002-026300, a radiographic image detector using a CMOS sensor, etc., may be used in all the above-described embodiments.

Figure 22:
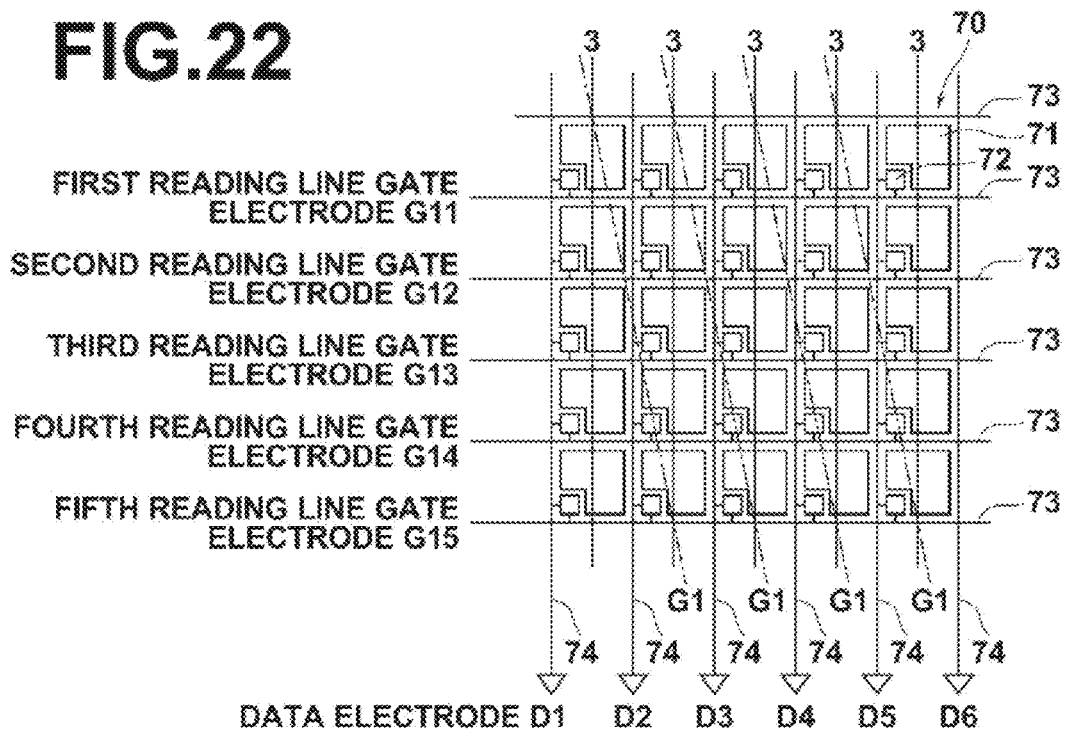
FIG. 22 is a diagram illustrating a positional relationship among a radiographic image detector employing TFT switches, the self image of the first grating and the second grating.

Specifically, as shown in FIG. 22, for example, the radiographic image detector using TFT switches includes a number of two-dimensionally arranged pixel circuits 70, each of which includes: a pixel electrode 71 for collecting electric charges generated by photoelectric conversion at a semiconductor film when the semiconductor film is exposed to radiation; and a TFT switch 72 for reading out the electric charge collected by the pixel electrode 71 as an image signal. The radiographic image detector using TFT switches also includes: a number of gate electrodes 73, each of which is provided for each pixel circuit row, and to which a gate scan signal for turning on or off the TFT switches 72 is fed; and a number of data electrodes 74, each of which is provided for each pixel circuit column, and to which an electric charge signal read out from each pixel circuit 70 is fed. Details of the layer structure of each pixel circuit 70 are the same as the layer structure taught in Japanese Unexamined Patent Publication No. 2002-026300.

For example, in the case where the second grating 3 is positioned to be parallel to the pixel circuit columns (the data electrodes), one pixel circuit column corresponds to the main pixel size Dx in the above-described embodiments, and one pixel circuit row corresponds to the sub-pixel size Dy in the above-described embodiments. The main pixel size Dx and the sub-pixel size Dy may, for example, be 50 µm.

Then, in the case where M fringe images are used to generate a phase-contrast image, similarly to the above-described embodiments, the self image G1 of the first grating 2 is inclined relative to the second grating 3 such that M pixel circuit rows correspond to one image resolution D in the sub-scanning direction of the phase-contrast image. The specific angle of rotation of the self image G1 of the first grating 2 is calculated according to Expression (13), (21) or (32) above, similarly to the above-described embodiments.

In the case where the angle of rotation θ of the self image G1 of the first grating 2 is set according to Expression (13) above where M=5 and n=1, for example, an image signal corresponding to a fraction of an intensity modulation for one period of the self image G1 of the first grating 2 divided by 5 can be detected by one pixel circuit 70 shown in FIG. 22. That is, image signals of five different fringe images can be detected by five pixel circuit rows connected to five gate electrodes 73 shown in FIG. 22. While FIG. 22 shows one second grating 3 and one self image G1 corresponding to each pixel circuit column, actually, a number of second gratings 3 and a number of self images G1 may be present correspondingly to each pixel circuit column, although this case is not shown in FIG. 22.

Therefore, the image signal read out from the pixel circuit row connected to the first reading line gate electrode G11 is obtained as a first fringe image signal M1, the image signal read out from the pixel circuit row connected to the second reading line gate electrode G12 is obtained as a second fringe image signal M2, the image signal read out from the pixel circuit row connected to the third reading line gate electrode G13 is obtained as a third fringe image signal M3, the image signal read out from the pixel circuit row connected to the fourth reading line gate electrode G14 is obtained as a fourth fringe image signal M4 and the image signal read out from the pixel circuit row connected to the fifth reading line gate electrode G15 is obtained as a fifth fringe image signal M5.

The method for generating a phase-contrast image based on the first to fifth fringe image signals is the same as that in the above-described embodiments. It should be noted that, in the case where the size of one pixel circuit 70 in the main scanning direction and the sub-scanning direction is 50 µm, as described above, the image resolution in the main scanning direction of the phase-contrast image is 50 µm, and the image resolution in the sub-scanning direction of the phase-contrast image is 50 µm×5=250 µm.

The directions in which the gate electrodes and the data electrodes of the radiographic image detector extend are not limited to those in the example shown in FIG. 22. For example, the radiographic image detector may be positioned such that the gate electrodes extend in the vertical direction in the drawing and the data lines extend in the horizontal direction in the drawing.

Alternatively, the self image G1 of the first grating 2 and the second grating 3 may be rotated by 90° relative to the position of the radiographic image detector shown in FIG. 22. In this case, by obtaining image signals read out from the pixel circuits 70 arranged in the direction parallel to the gate electrodes, the image signals forming different fringe images can be obtained, similarly to the above-described embodiments.

The shape of each pixel and the shape of the pixel grating of the radiographic image detector are not limited to square, and may be a rectangle or a parallelogram, for example. The pixel arrangement may be such an arrangement that is provided when the pixel grating is rotated by 45°.

Also, in the above-described case where the radiographic image detector using TFT switches is employed, the self image G1 of the first grating 2 may be positioned parallel to the second grating 3 and the second grating 3 having an arrangement pitch different from the arrangement pitch of the self image G1 of the first grating 2 may be used to form a moire pattern, or the second grating 3 having an arrangement pitch different from the arrangement pitch of the self image G1 of the first grating 2 may be used and the self image G1 of the first grating 2 may be inclined relative to the second grating 3 to form a moire pattern.

Also, in the above-described case where the radiographic image detector using TFT switches is employed, the period direction of the self image G1 of the first grating 2 or the period direction of the second grating 3 may not necessarily be the same as either one of the directions orthogonal to the direction in which the pixel circuits 70 of the radiographic image detector are arranged. As described above, as long as image signals of pixels arranged in a direction parallel to or a direction intersecting the period direction of the moire pattern formed by the self image G1 of the first grating 2 and the second grating 3 other than a direction orthogonal to the period direction of the moire pattern can be obtained, the relationship between the period directions of the first and second gratings 2 and 3 and the arrangement direction of the pixel circuits 70 of the radiographic image detector may be any relationship.

Figure 23:
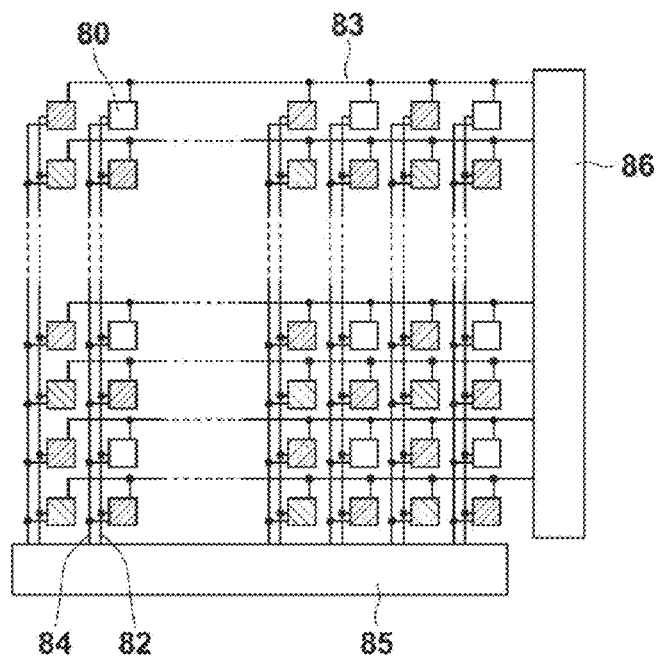
FIG. 23 is a diagram illustrating the schematic structure of a radiographic image detector employing a CMOS sensor.

As the radiographic image detector using a CMOS sensor, one having a number of two-dimensionally arranged pixel circuits 80, which generate visible light when exposed to radiation and convert the visible light into electricity by photoelectric conversion to detect electric charge signals, as shown in FIG. 23, may be used, for example. The radiographic image detector using a CMOS sensor includes: a number of gate electrodes 82 and a number of reset electrodes 84, each of which is provided for each pixel circuit row, and to which a driving signal for driving a signal reading circuit included in each pixel circuit 80 is fed; and a number of data electrodes 83, each of which is provided for each pixel circuit column, and to which an electric charge signal read out from the signal reading circuit of each pixel circuit 80 is fed. A row selecting and scanning unit 85 for outputting the driving signals to the signal reading circuits is connected to the gate electrodes 82 and the reset electrodes 84. A signal processing unit 86 for applying predetermined processing to the electric charge signal outputted from each pixel circuit is connected to the data electrodes 83.

Figure 24:
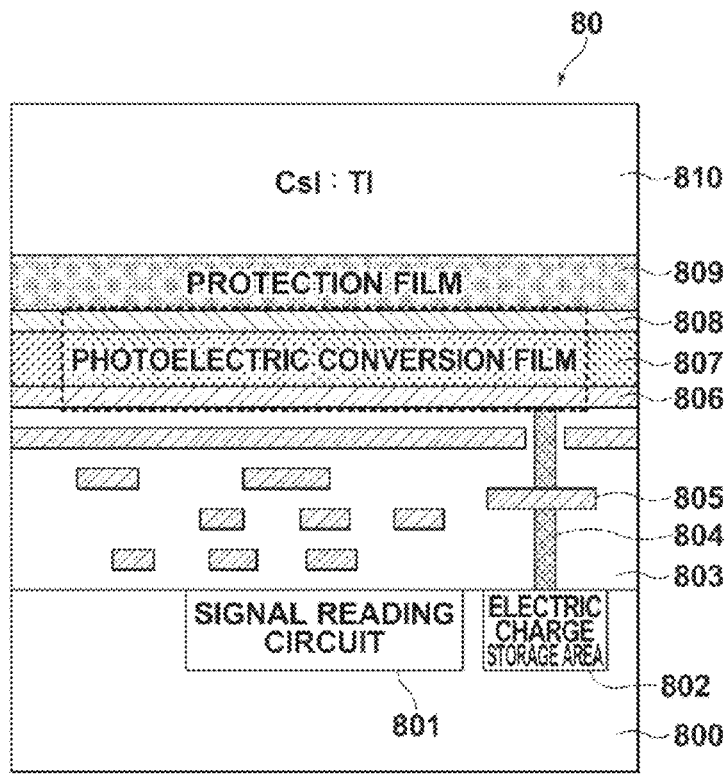
FIG. 24 is a diagram illustrating the structure of one pixel circuit of the radiographic image detector employing a CMOS sensor.

As shown in FIG. 24, each pixel circuit 80 includes: a lower electrode 806, which is formed above a substrate 800 via an insulating film 803; a photoelectric conversion film 807 formed above the lower electrode 806; an upper electrode 808 formed above the photoelectric conversion film 807; a protection film 809 formed above the upper electrode 808; and a radiation conversion film 810 formed above the protection film 809.

The radiation conversion film 810 is formed, for example, by CsI:TI, which emits light of a wavelength of 550 nm when exposed to radiation. It is desirable that the thickness of the radiation conversion film 810 is around 500 µm.

Since it is necessary that the light of the wavelength of 550 nm enters the photoelectric conversion film 807, the upper electrode 808 is formed by a conductive material that is transparent to the entering light. The lower electrode 806 is a thin film that is divided correspondingly to each pixel circuit 80, and is formed by a transparent or opaque conductive material.

The photoelectric conversion film 807 is formed, for example, by a photoelectric conversion material that absorbs the light of the wavelength of 550 nm and generates an electric charge depending on the light. Examples of such a photoelectric conversion material may include organic semiconductors, organic materials containing an organic colorant, and materials formed by one of or a combination of inorganic semiconductor crystals having direct transition band gap and large absorption coefficient.

When a predetermined bias voltage is applied between the upper electrode 808 and the lower electrode 806, one part of the electric charges generated at the photoelectric conversion film 807 moves to the upper electrode 808, and the other part of the electric charges moves to the lower electrode 806.

Within the substrate 800 below the lower electrode 806, an electric charge storage area 802 for storing the electric charges moved to the lower electrode 806, and a signal reading circuit 801 for converting the electric charge stored in the electric charge storage area 802 into a voltage signal and outputting the voltage signal are formed correspondingly to the lower electrode 806.

The electric charge storage area 802 is electrically connected to the lower electrode 806 via a plug 804 made of a conductive material extending through the insulating film 803. The signal reading circuit 801 is formed by a known CMOS circuit.

Figure 25:
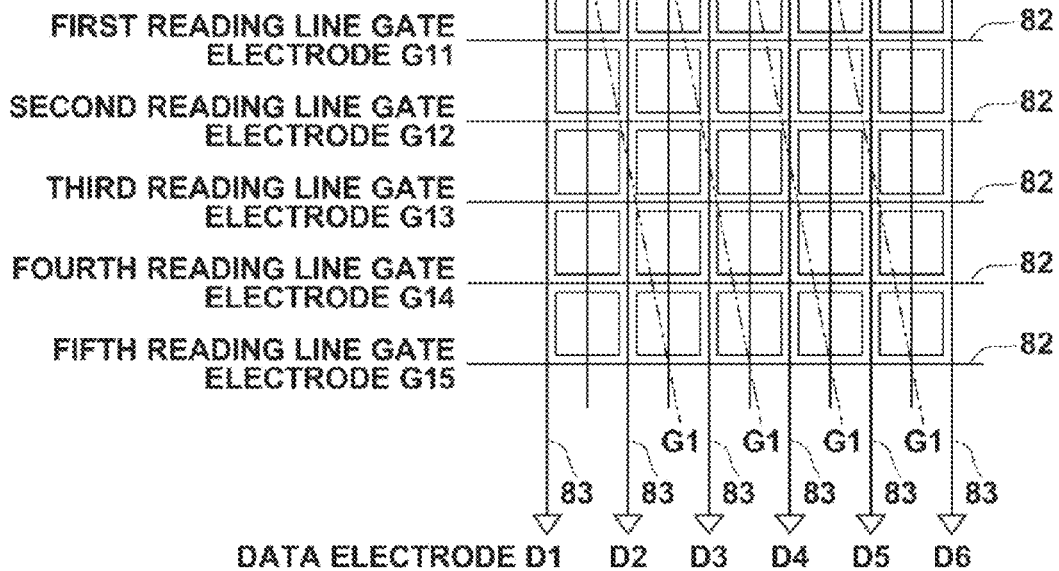
FIG. 25 is a diagram illustrating a positional relationship among the radiographic image detector employing a CMOS sensor, the self image of the first grating and the second grating.

In the case where the radiographic image detector using a CMOS sensor, as described above, is positioned such that the pixel circuit columns (data electrodes) are parallel to the second grating 3, as shown in FIG. 25, one pixel circuit column corresponds to the main pixel size Dx in the above-described embodiments, and one pixel circuit row corresponds to the sub-pixel size Dy in the above-described embodiments. In the case of the radiographic image detector using a CMOS sensor, the main pixel size Dx and the sub-pixel size Dy may, for example, be 10 μm.

Then, in the case where M fringe images are used to generate a phase-contrast image, similarly to the above-described embodiments, the self image G1 of the first grating 2 is inclined relative to the second grating 3 such that M pixel circuit rows correspond to one image resolution D in the sub-scanning direction of the phase-contrast image. The specific angle of rotation of the self image G1 of the first grating 2 is calculated according to Expression (13), (21) or (32) above, similarly to the above-described embodiments.

In the case where the angle of rotation θ of the self image G1 of the first grating 2 is set according to Expression (13) above where M=5 and n=1, for example, an image signal corresponding to a fraction of an intensity modulation for one period of the self image G1 of the first grating 2 divided by 5 can be detected by one pixel circuit 80 shown in FIG. 25. That is, image signals of five different fringe images can be detected by five pixel circuit rows connected to five gate electrodes 82 shown in FIG. 25. While FIG. 25 shows one second grating 3 and one self image G1 corresponding to each pixel circuit column, actually, a number of second gratings 3 and a number of self images G1 may be present correspondingly to each pixel circuit column, although this case is not shown in FIG. 25.

Therefore, similarly to the case of the radiographic image detector using TFT switches, the image signal read out from the pixel circuit row connected to the first reading line gate electrode G11 is obtained as the first fringe image signal M1, the image signal read out from the pixel circuit row connected to the second reading line gate electrode G12 is obtained as the second fringe image signal M2, the image signal read out from the pixel circuit row connected to the third reading line gate electrode G13 is obtained as the third fringe image signal M3, the image signal read out from the pixel circuit row connected to the fourth reading line gate electrode G14 is obtained as the fourth fringe image signal M4 and the image signal read out from the pixel circuit row connected to the fifth reading line gate electrode G15 is obtained as the fifth fringe image signal M5.

Further, similarly to the case of the radiographic image detector using TFT switches, directions along which the gate electrodes and the data electrodes of the radiographic image detector extend are not limited to those in the example shown in FIG. 25. For example, the radiographic image detector may be positioned such that the gate electrodes extend in the vertical direction in the drawing and the data lines extend in the horizontal direction in the drawing.

Alternatively, the self image G1 of the first grating 2 and the second grating 3 may be rotated by 90° relative to the position of the radiographic image detector shown in FIG. 25. In this case, by obtaining image signals read out from the pixel circuits 80 arranged in the direction parallel to the gate electrodes, the image signals forming different fringe images can be obtained, similarly to the above-described embodiments.

The shape of each pixel and the shape of the pixel grating of the radiographic image detector are not limited to square, and may be a rectangle or a parallelogram, for example. The pixel arrangement may be such an arrangement that is provided when the pixel grating is rotated by 45°.

Also, similarly to the case where the radiographic image detector using TFT switches is used, the self image G1 of the first grating 2 may be positioned parallel to the second grating 3 and the second grating 3 having an arrangement pitch different from the arrangement pitch of the self image G1 of the first grating 2 may be used to form a moire pattern, or the second grating 3 having an arrangement pitch different from the arrangement pitch of the self image G1 of the first grating 2 may be used and the self image G1 of the first grating 2 may be inclined relative to the second grating 3 to form a moire pattern.

Also, similarly to the case where the radiographic image detector using TFT switches is used, the period direction of the self image G1 of the first grating 2 or the period direction of the second grating 3 may not necessarily be the same as either one of the directions orthogonal to the direction in which the pixel circuits 80 of the radiographic image detector are arranged. As described above, as long as image signals of pixels arranged in a direction parallel to or a direction intersecting the period direction of the moire pattern formed by the self image G1 of the first grating 2 and the second grating 3 other than a direction orthogonal to the period direction of the moire pattern can be obtained, the relationship between the period directions of the first and second gratings 2 and 3 and the arrangement direction of the pixel circuits 80 of the radiographic image detector may be any relationship.

The method for generating a phase-contrast image based on the first to fifth fringe image signals is the same as that in the above-described embodiments. It should be noted that, in the case where the size of one pixel circuit 80 in the main scanning direction and the sub-scanning direction is 10 μm, as described above, the image resolution in the main scanning direction of the phase-contrast image is 10 μm, and the image resolution in the sub-scanning direction of the phase-contrast image is 10 μm×5=50 μm.

It should be noted that, while the radiographic image detector using TFT switches or the radiographic image detector using a CMOS sensor may be used, as described above, these radiographic image detectors typically have square pixels, and the resolution in the sub-scanning direction resolution is degraded relative to the resolution in the main scanning direction when the present invention is applied thereto. In contrast, with the radiographic image detector using the optical reading system described in the first and second embodiments, although the resolution Dx in the main scanning direction is limited by the width of the linear electrodes (in the direction orthogonal to the direction in which the linear electrodes extend), the resolution Dy in the sub-scanning direction is determined by the width in the sub-scanning direction of the reading light from the linear reading light source 50 and a product of a storage time per line of the charge amplifier 200 and the traveling speed of the linear reading light source 50. The resolutions in the main scanning direction and in the sub-scanning direction are typically several tens micrometers. However, it is possible to design such that the resolution in the sub-scanning direction is increased while the resolution in the main scanning direction is maintained. For example, such a design can be achieved by reducing the width of the linear reading light source 50 or reducing the traveling speed, and the radiographic image detector using the optical reading system described in the first and second embodiments is more advantageous.

Further, since a plurality of fringe image signals can be obtained by a single imaging operation, a storage phosphor sheet or a silver salt film may also be used, besides the semiconductor detector as described above that can be repeatedly used immediately. It should be noted that, in this case, pixels obtained by reading the storage phosphor sheet or developed silver salt film correspond to pixels recited in the claims.

The basic configuration of the radiographic phase-contrast imaging apparatus of the invention has been described. Next, configurations of specific systems using this basic configuration are described. It should be noted that all the above-described embodiments are applicable to the systems described below.

Figure 26:
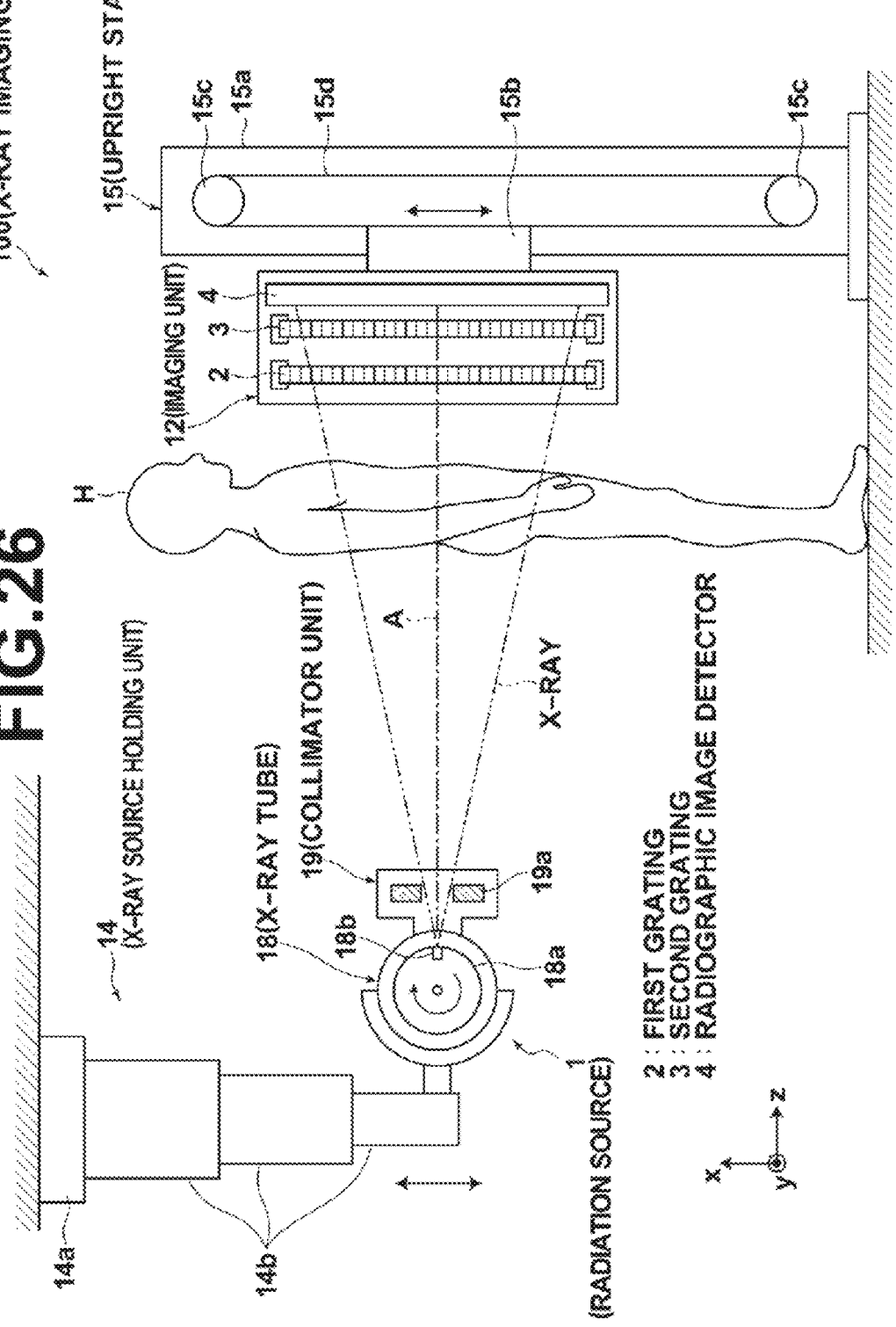
FIG. 26 is a diagram illustrating the schematic structure of an X-ray imaging system capable of imaging in the upright position employing one embodiment of the invention.
Figure 27:
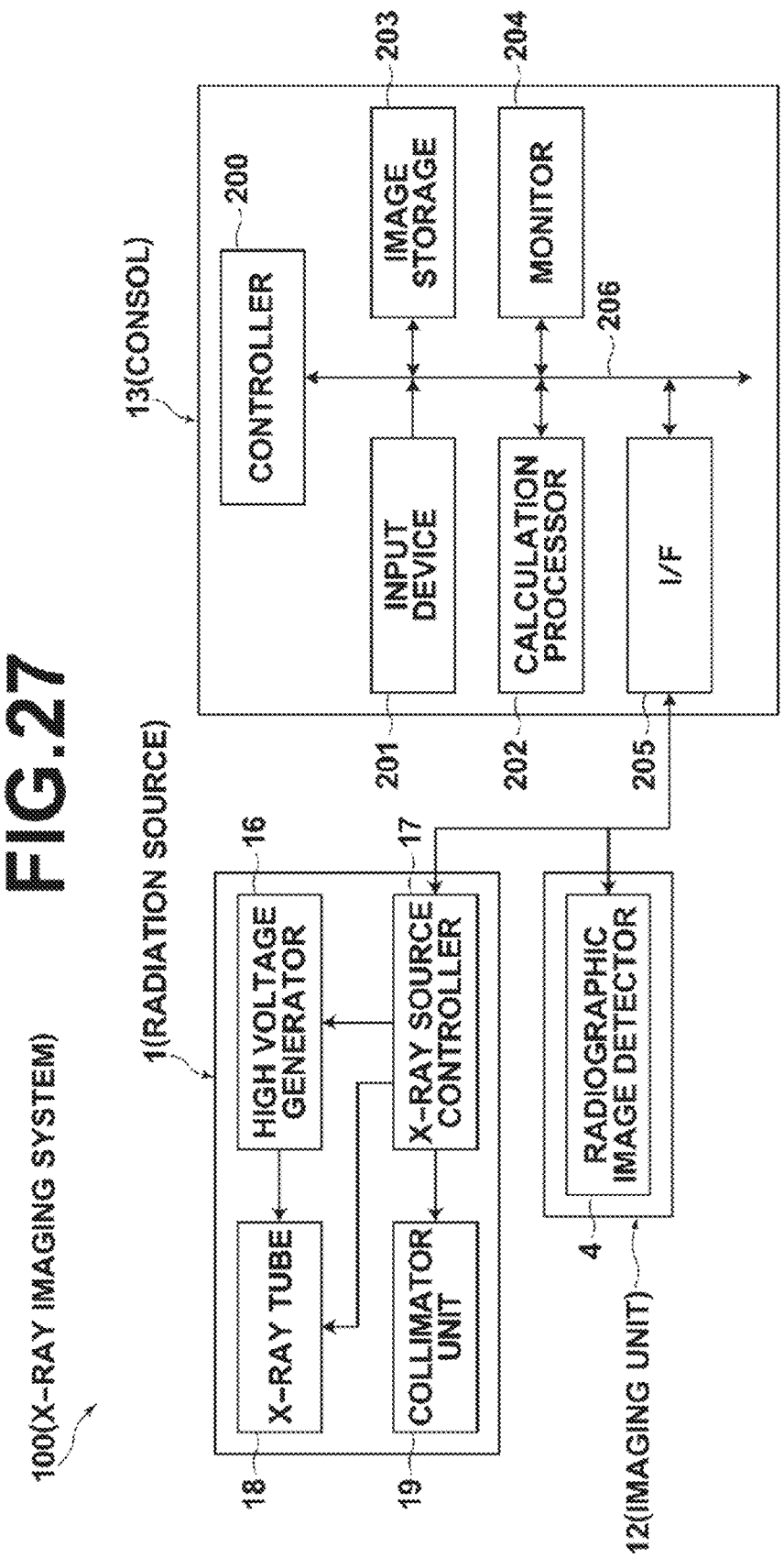
FIG. 27 is a block diagram illustrating the schematic configuration of the X-ray imaging system capable of imaging in the upright position employing one embodiment of the invention.

An X-ray imaging system 100 shown in FIGS. 26 and 27 is formed by applying the radiographic phase-contrast imaging apparatus of the above-described embodiments to an X-ray diagnostic apparatus that performs imaging of a subject H in the upright position.

Specifically, the X-ray imaging system 100 includes: the radiation source 1 for applying an X-ray to the subject H; an imaging unit 12, disposed to face the radiation source 1, for detecting the X-ray, which is emitted from the radiation source 1 and transmitted through the subject H, and generating image data; and a console 13 for controlling the exposure operation of the radiation source 1 and the imaging operation of the imaging unit 12 based on operation by the operator, and processing the image signals obtained by the imaging unit 12 to generate a phase-contrast image.

The radiation source 1 is held by an X-ray source holding unit 14, which is suspended from the ceiling, so as to be movable in the vertical direction (X-direction). The imaging unit 12 is held by an upright stand 15, which is placed on the floor, so as to be movable in the vertical direction.

The radiation source 1 is formed by an X-ray tube 18, which generates an X-ray in response to a high voltage applied from a high voltage generator 16 based on control by an X-ray source controller 17, and a collimator unit 19 including a movable collimator 19a, which limits the radiation field to shield parts of the X-ray emitted from the X-ray tube 18 which do not contribute to the examination area of the subject H. The X-ray tube 18 is of the anode rotation type, where an electron beam emitted from a filament (not shown), which serves as an electron emission source (cathode), hits a rotating anode 18a, which rotates at a predetermined speed, to generate an X-ray. The part of the rotating anode 18a hit by the electron beam becomes an X-ray focal spot 18b.

The X-ray source holding unit 14 is formed by a carriage 14a, which is movable in the horizontal direction (Z-direction) via a ceiling rail (not shown) disposed on the ceiling, and a supporting post 14b, which is formed by members coupled in the vertical direction. The carriage 14a includes a motor (not shown) for extending and retracting the supporting post 14b to change the position of the radiation source 1 in the vertical direction.

The upright stand 15 includes a main body 15a placed on the floor, to which a holder 15b for holding the imaging unit 12 is attached so as to be movable in the vertical direction. The holder 15b is connected to an endless belt 15d, which is wrapped around two pulleys 15c that are disposed at positions apart from each other in the vertical direction. The holder 15b is driven by a motor (not shown) which drives the pulleys 15c to rotate. The driving by the motor is controlled by a controller 20 (which will be described later) of the consol 13 based on setting operation by the operator.

The upright stand 15 also includes a position sensor (not shown), such as a potentiometer, for measuring an amount of movement of the pulleys 15c or the endless belt 15d to detect the position of the imaging unit 12 in the vertical direction. A value detected by the position sensor is fed to the X-ray source holding unit 14 via a cable, or the like. The X-ray holding unit 14 extends or retracts the supporting post 14b based on the detected value fed thereto to move the radiation source 1 to follow the movement of the imaging unit 12 in the vertical direction.

The consol 13 includes the controller 200, which is formed by a CPU, a ROM, a RAM, etc. An input device 201 used to input an instruction to perform an imaging operation from the operator and the content thereof, a calculation processor 202 for processing the image signals obtained by the imaging unit 12 to generate a phase-contrast image, an image storage 203 for storing phase-contrast images, a monitor 204 for displaying a phase-contrast image, etc., and an interface (I/F) 205, which is connected to the individual units of the X-ray imaging system 100, are connected to the controller 200 via a bus 206. It should be noted that the calculation processor 202 corresponds to the phase-contrast image generation unit 5 in the above-described embodiments.

As the input device 201, for example, a switch, a touch panel, a mouse, a keyboard, etc., may be used. X-ray imaging conditions, such as an X-ray tube voltage and an X-ray exposure time, imaging timing, etc., are inputted via operation of the input device 201. The monitor 204 is formed by a liquid crystal display, or the like, and displays a text, such as the X-ray imaging conditions, and a phase-contrast image according to control by the controller 200.

The imaging unit 12 includes the first grating 2, the second grating 3 and the radiographic image detector 4 explained in the above-described embodiments. The radiographic image detector 4 is positioned such that the detection surface thereof is orthogonal to an optical axis A of the X-ray emitted from the radiation source 1. As explained in the above-described embodiments, the first grating 2 and the second grating 3 are positioned such that the directions in which the members 22 and the members 23 extend are inclined relative to each other.

Figure 28:
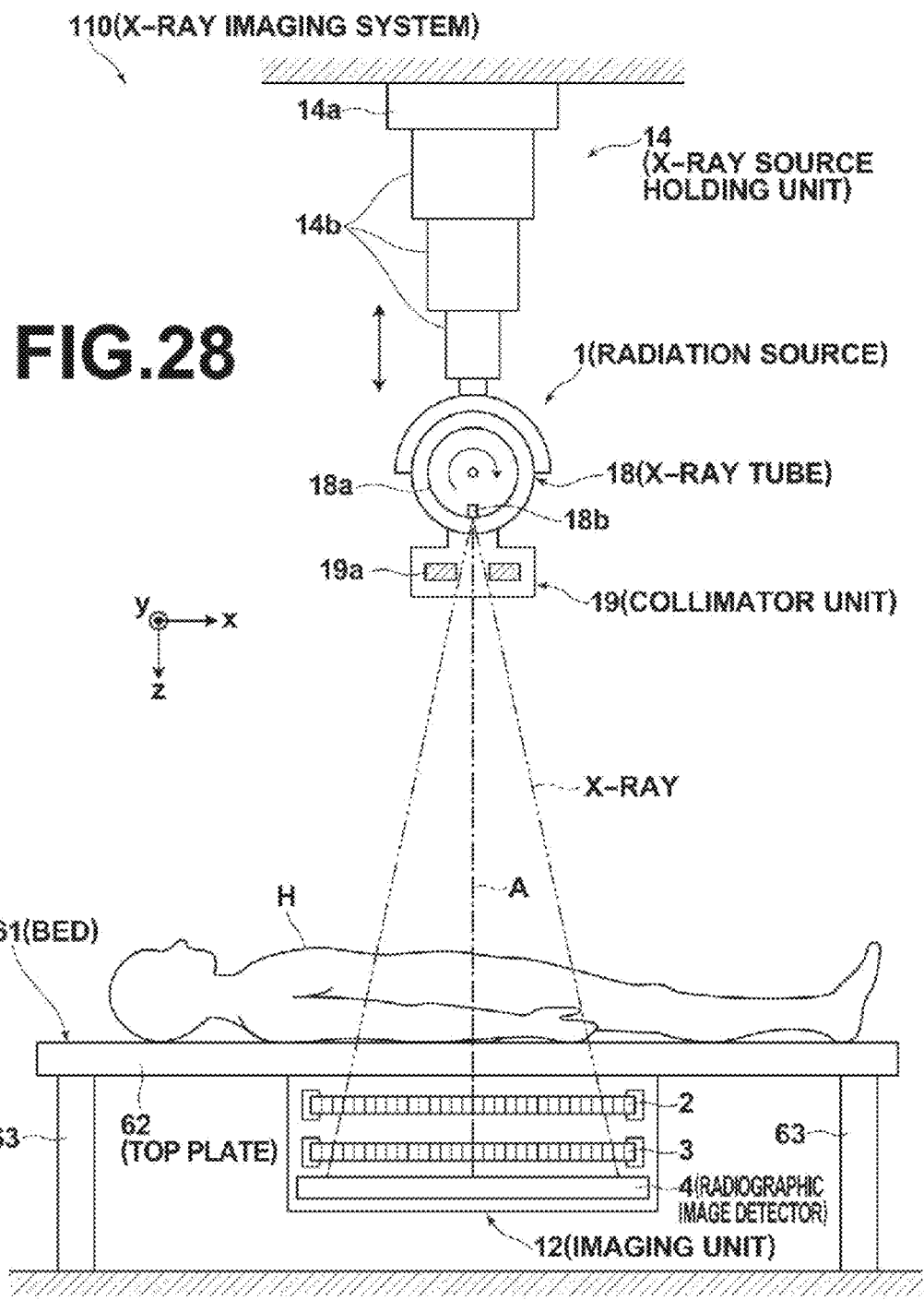
FIG. 28 is a diagram illustrating the schematic structure of an X-ray imaging system capable of imaging in the supine position employing one embodiment of the invention.

Next, an X-ray imaging system 110 shown in FIG. 28 is formed by applying the radiographic phase-contrast imaging apparatus of the above-described embodiments to an X-ray diagnostic apparatus for imaging a subject H in the supine position.

The X-ray system 110 includes, besides the radiation source 1 and the imaging unit 12 of the above-described X-ray imaging system 100, a bed 61, on which the subject H lies down. The radiation source 1 and the imaging unit 12 have the same configurations as those of the above-described X-ray imaging system 100, and therefore the components thereof are designated by the same symbols as those of the X-ray imaging system 100. In the following description, only the differences from the above-described X-ray imaging system 100 are described. The other components and operations are the same as those of the above-described X-ray imaging system 100, and the explanations thereof are omitted.

In the X-ray imaging system 110, the imaging unit 12 is attached on the bottom surface of a top plate 62 so as to face the radiation source 1 via the subject H. The radiation source 1 is held by the X-ray source holding unit 14, and an angle changing mechanism (not shown) of the radiation source 1 orients the radiation source 1 such that the X-ray is emitted downward. In this state, the radiation source 1 applies the X-ray to the subject H lying down on the top plate 62 of the bed 16. The X-ray source holding unit 14 allows vertical movement of the radiation source 1 by extending or retracting the supporting post 14b, and the distance from the X-ray focal spot 18b to the detection surface of the radiographic image detector 3 can be adjusted by this vertical movement.

It should be noted that, if the configuration of the radiographic phase-contrast imaging apparatus of the second embodiment, for example, is employed as the configuration of the imaging unit 12, the distance between the grating 2 and the radiographic image detector 3 can be set shorter and the imaging unit 12 can be made thinner. This allows providing short legs 63 to support the top plate 62 of the bed 61, thereby making the position of the top plate 62 lower. For example, it is preferable to provide a thin imaging unit 12 and make the position of the top plate 62 be a height that facilitates the subject H to sit down on the top plate 62 (for example, around 40 cm above the floor). Making the position of the top plate 62 lower is also preferable in view of ensuring a sufficient distance from the radiation source 1 to the imaging unit 12.

It should be noted that the imaging of the subject H in the supine position can also be achieved by attaching the radiation source 1 to the bed 61 and placing the imaging unit 12 on the ceiling, which is the opposite positional relationship between the radiation source 1 and the imaging unit 12 from that described above.

By enabling the supine position imaging of the phase-contrast image, as described with respect to the X-ray imaging system 110, imaging of the lumbar vertebrae, the hip joint, etc., which are difficult positions to be imaged, of the subject H can be performed. Further, an appropriate fastening means for fastening the subject H on the bed 61 may be used to reduce degradation of the phase-contrast image due to body motion.

Figure 29:
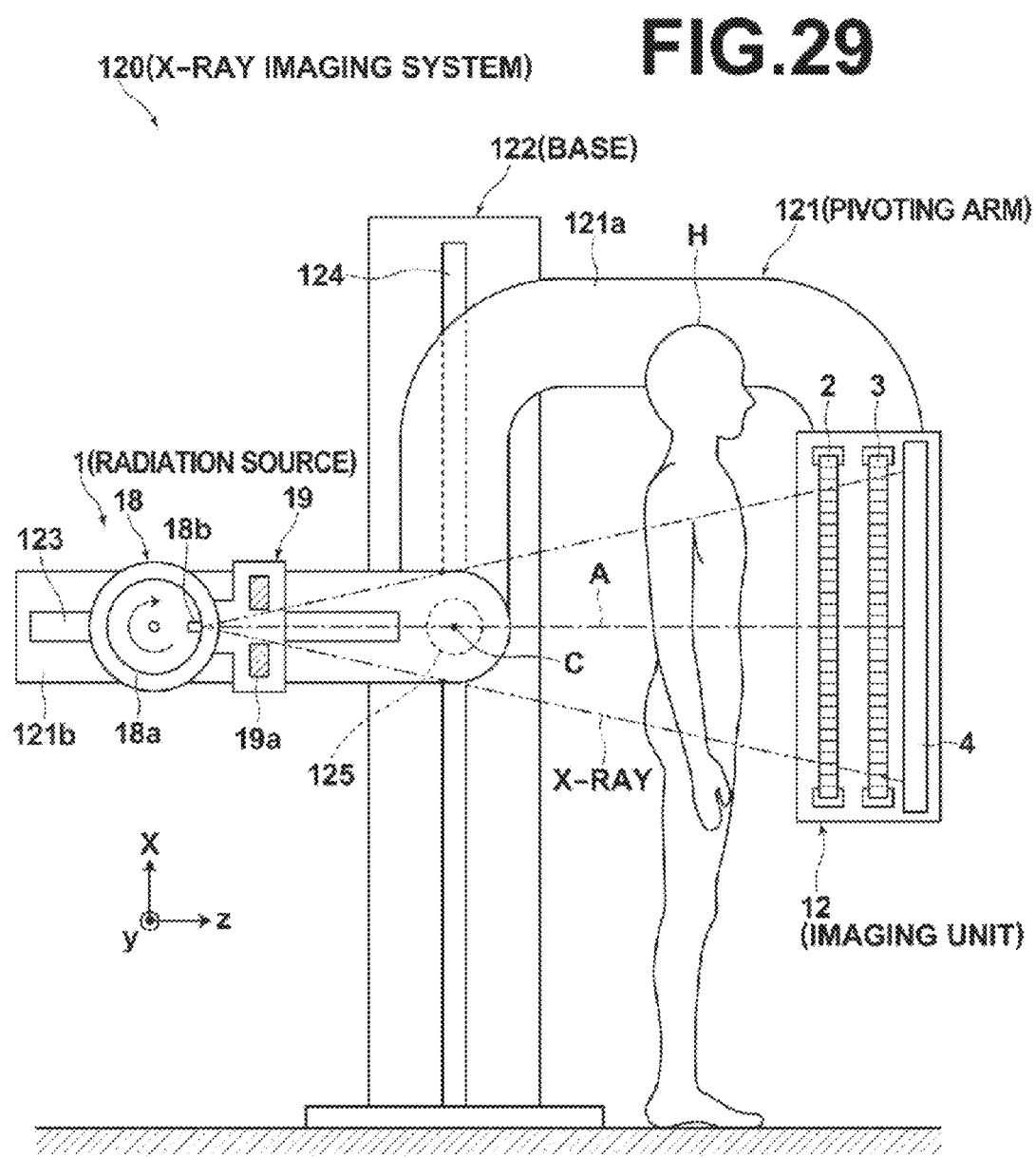
FIG. 29 is a diagram illustrating the schematic structure of an X-ray imaging system capable of imaging in the upright position and in the supine position employing one embodiment of the invention.
Figure 30:
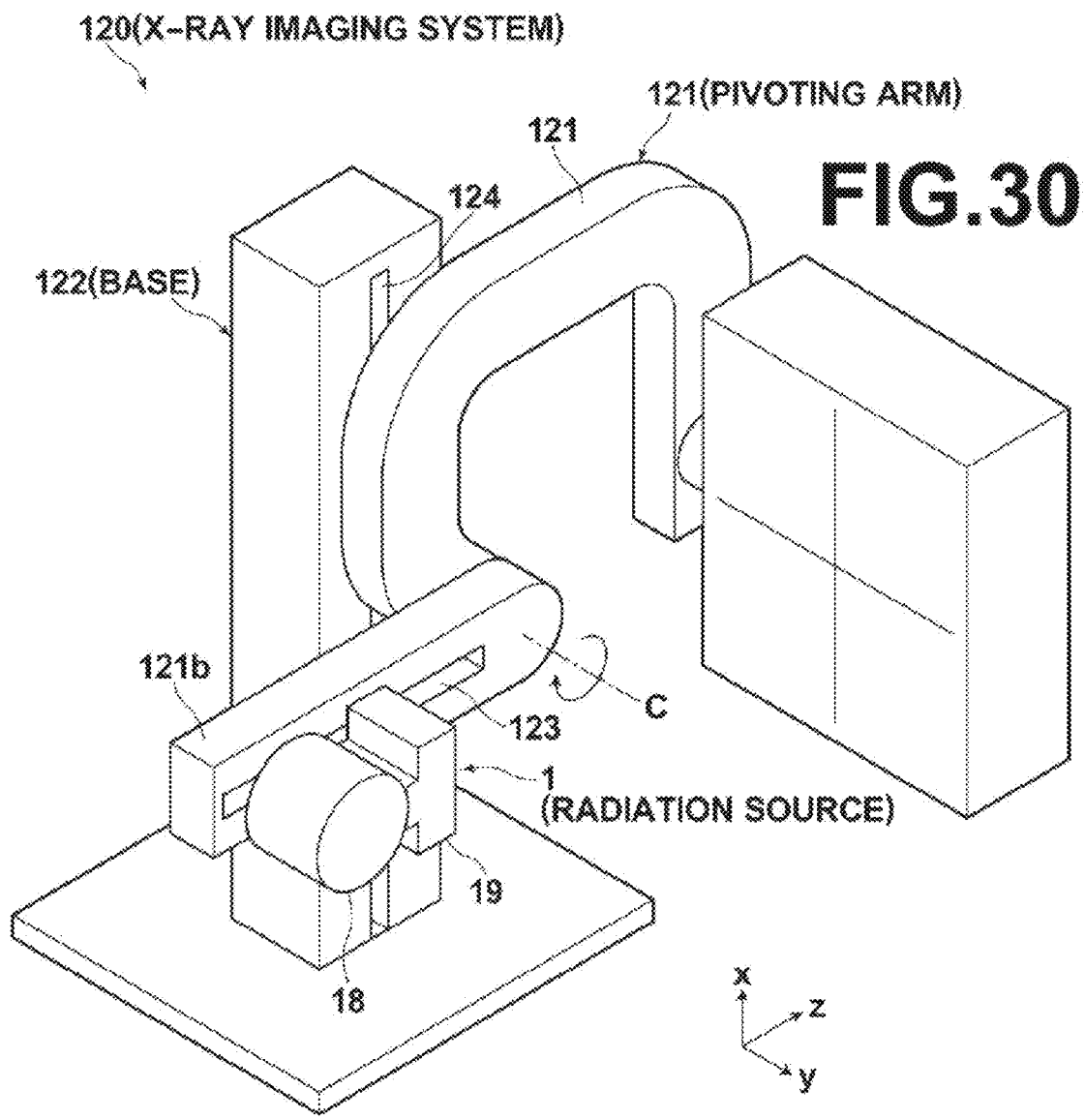
FIG. 30 is a diagram illustrating the schematic structure of the X-ray imaging system capable of imaging in the upright position and in the supine position employing one embodiment of the invention.

Next, an X-ray imaging system 120 shown in FIGS. 29 and 30 is formed by applying the radiographic phase-contrast imaging apparatus of the above-described embodiments to an X-ray diagnostic apparatus for imaging the subject H in the upright position and in the supine position.

In the X-ray system 120, the radiation source 1 and the imaging unit 12 are held by a pivoting arm 121. The pivoting arm 121 is pivotably coupled to a base 122. The radiation source 1 and the imaging unit 12 have the same configurations as those of the above-described X-ray imaging system 100, and therefore the components thereof are designated by the same symbols as those of the X-ray imaging system 100. In the following description, only the differences from the above-described X-ray imaging system 100 are described. The other components and operations are the same as those of the above-described X-ray imaging system 100, and the explanations thereof are omitted.

The pivoting arm 121 is formed by a U-shaped member 121a which is substantially U-shaped, and a linear member 121b connected to one end of the U-shaped member 121a. The imaging unit 12 is attached to the other end of the U-shaped member 121a. The linear member 121b includes a first groove 123, which is formed along the direction in which the linear member 121b extends, and the radiation source 1 is slidably attached to the first groove 123. The radiation source 1 and the imaging unit 12 face each other. The distance from the X-ray focal spot 18b to the detection surface of the radiographic image detector 3 can be adjusted by moving the radiation source 1 along the first groove 123.

The base 122 includes a second groove 124, which extends in the vertical direction. The pivoting arm 121 is movable in the vertical direction along the second groove 124 by a coupling mechanism 125, which is disposed at the connecting area between the U-shaped member 121a and the linear member 121b. The pivoting arm 121 is pivotable about an axis of rotation C, which extends along the y-direction, by the coupling mechanism 125. The supine position imaging can be performed by pivoting the pivoting arm 121 clockwise about the axis of rotation C by an angle of 90° from the upright position shown in FIG. 29, and placing the imaging unit 12 below a bed (not shown), on which the subject H lies down. The angle of pivot of the pivoting arm 121 is not limited to 90°, and the pivoting arm 121 may be pivoted by any angle. Therefore, imaging in a direction other than the upright position imaging (the horizontal direction) and the supine position imaging (the vertical direction) can also be performed.

In the X-ray imaging system 120, the imaging unit 12 is disposed at the U-shaped member 121a and the radiation source 1 is disposed at the linear member 121b. However, as with an X-ray diagnostic apparatus using a so-called C arm, the imaging unit 12 may be disposed at one end of a C arm and radiation source 1 may be disposed at the other end of the C arm.

Figure 31:
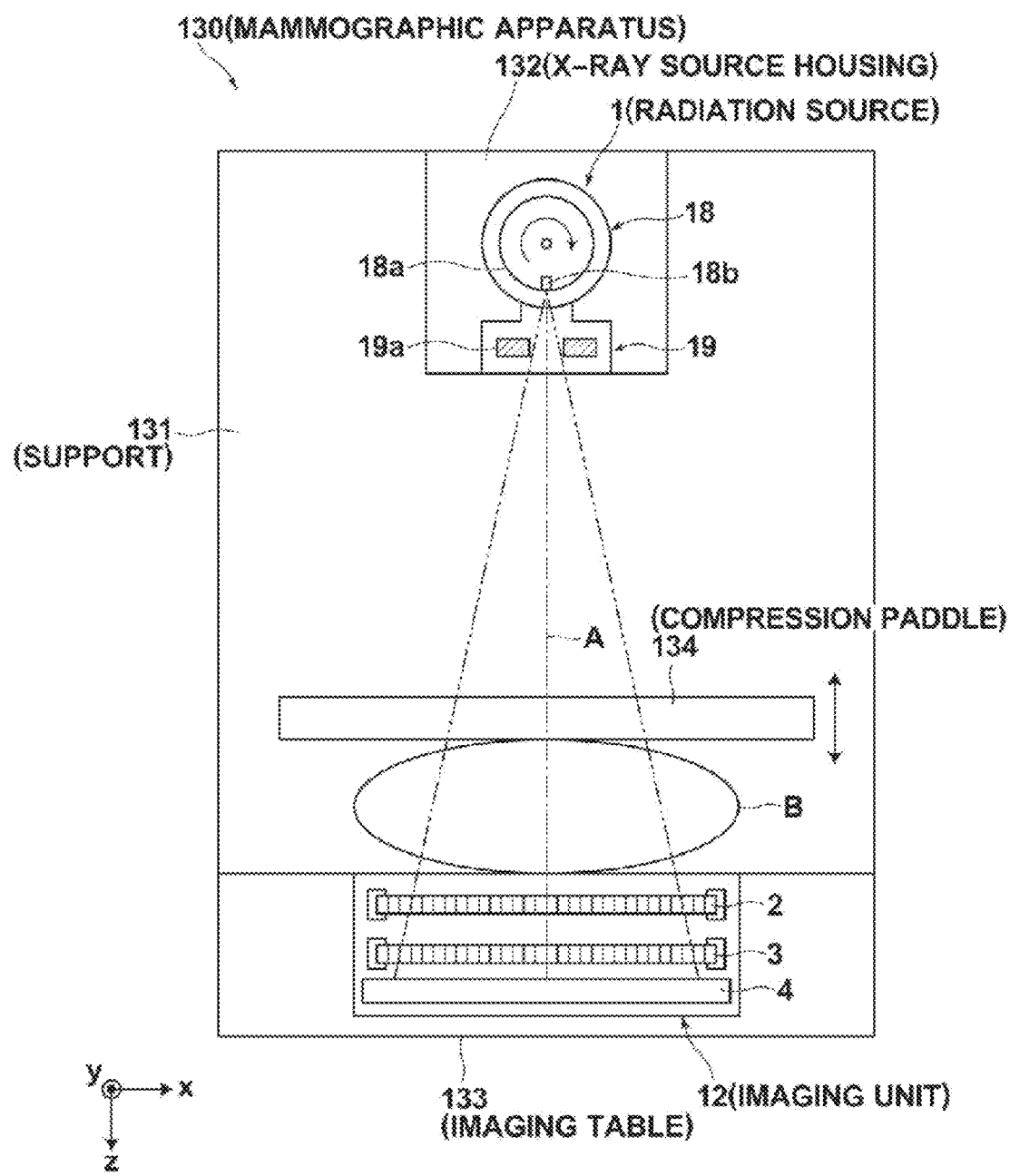
FIG. 31 is a diagram illustrating the schematic structure of a mammographic apparatus employing one embodiment of the invention.
Figure 32:
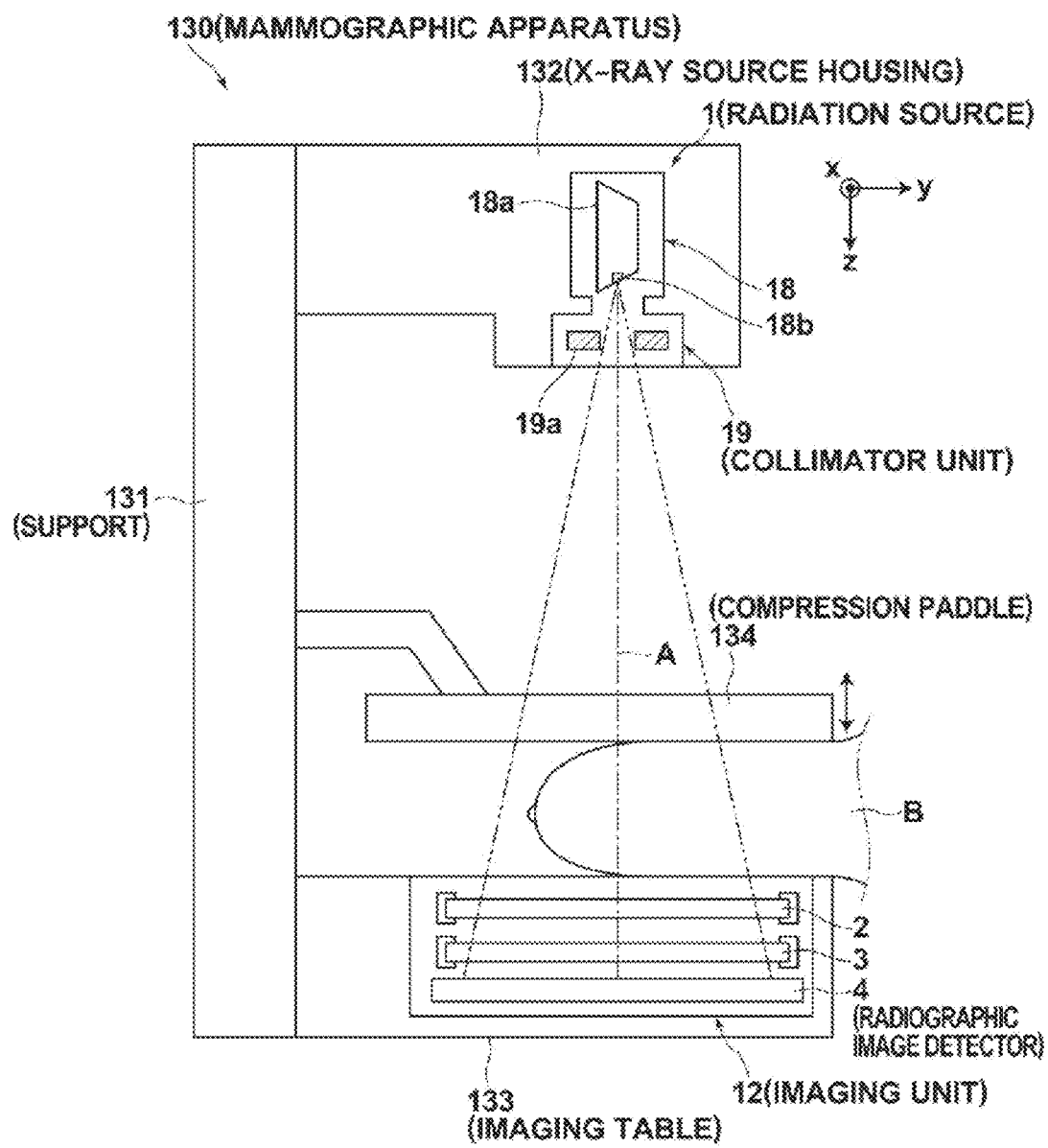
FIG. 32 is a diagram illustrating the schematic structure of the mammographic apparatus employing one embodiment of the invention.

Next, a mammographic apparatus 130 shown in FIGS. 31 and 32 is formed by applying the radiographic phase-contrast imaging apparatus of the above-described embodiments to mammography (X-ray breast imaging).

The mammographic apparatus 130 takes a phase-contrast image of a breast B, which is the subject. The mammographic apparatus 130 includes: an X-ray source housing 132 disposed at one end of a support 131, which is pivotably coupled to a base (not shown); an imaging table 133 disposed at the other end of the support 131; and a compression paddle 134, which is movable in the vertical direction relative to the imaging table 133.

The radiation source 1 is housed in the X-ray source housing 132, and the imaging unit 12 is housed in the imaging table 133. The radiation source 1 and the imaging unit 12 are disposed to face each other. The compression paddle 134 is moved by a compression paddle moving mechanism (not shown) to press the breast B, which is sandwiched between the compression paddle 134 and the imaging table 183. In this pressed state of the breast B, the above-described X-ray imaging is performed.

The radiation source 1 and the imaging unit 12 have the same configurations as those of the above-described X-ray imaging system 100, and therefore the components thereof are designated by the same symbols as those of the X-ray imaging system 100. The other components and operations are the same as those of the above-described X-ray imaging system 100, and the explanations thereof are omitted.

Figure 33:
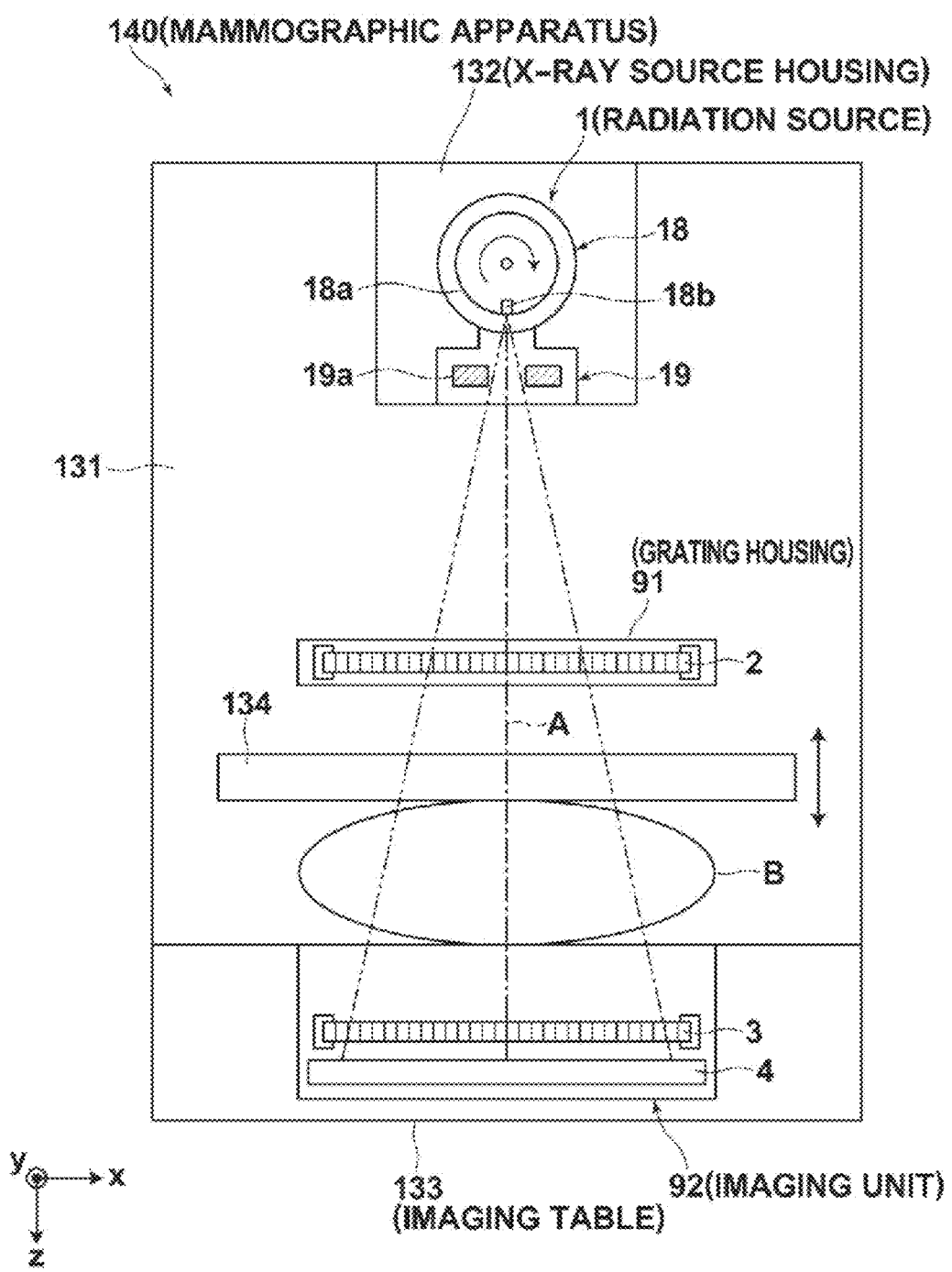
FIG. 33 is a diagram illustrating the schematic structure of a mammographic apparatus employing one embodiment of the invention with a grating placed between a radiation source and a subject.

Next, a modification of the mammographic apparatus is shown. The only difference of a mammographic apparatus 140 shown in FIG. 33 from the mammographic apparatus 130 is that the first grating 2 is placed between the radiation source 1 and the compression paddle 134. The first grating 2 is housed in a grating housing 91 connected to a support 131. The imaging unit 92 does not include the first grating 2, and is formed by the second grating 3 and the radiographic image detector 4.

Even in this case where the subject (breast) B is placed between the first grating 2 and the radiographic image detector 4, the self image G1 of the first grating 2 is deformed by the subject B. Therefore, also in this case, fringe images which reflect the distortion of the wave front of the radiation by the subject B can be detected by the radiographic image detector 4. That is, a phase-contrast image of the subject B can be obtained based on the above-described principle with the configuration of this mammographic apparatus 140.

It should be noted that the configuration where the subject is placed between the first grating 2 and the second grating 3 is not limited to mammographic apparatuses, and is applicable to other X-ray imaging systems.

Figure 34:
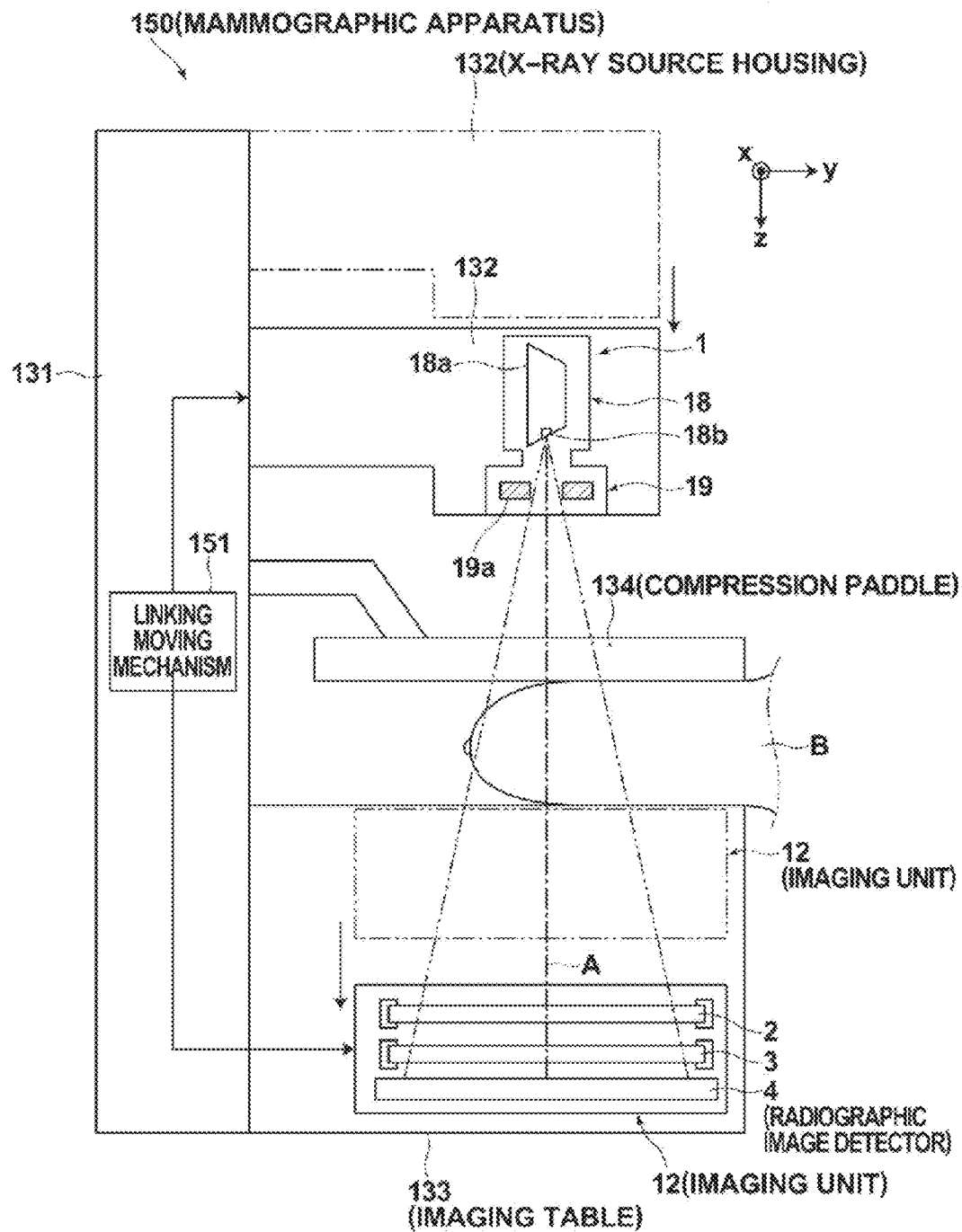
FIG. 34 is a diagram illustrating the schematic structure of a mammographic apparatus capable of magnified imaging employing one embodiment of the invention.

Next, FIG. 34 shows a mammographic apparatus 150 that is capable of magnified imaging of a subject B. The mammographic apparatus 150 includes a linking mechanism 151 for moving the X-ray source housing 132 and the imaging unit 12 in a linked manner. The linking mechanism 151 is controlled by the above-described controller 200, and moves the X-ray source housing 132 and the imaging unit 12 in the Z-direction while maintaining the relative positions of the radiation source 1, the grating 2 and the radiographic image detector 3.

The position of the subject B is fixed by the imaging table 133 and the compression paddle 134. By moving the X-ray source housing 132 and the imaging table 12 downward, the subject B approaches the radiation source 11, thereby achieving the magnified imaging of the subject B. The magnification factor may be inputted via the input device 201. As the magnification factor is inputted via the input device 201, the controller 200 controls the linking moving mechanism 151 to move the X-ray source housing 132 and the imaging unit 12 so that the distance from the subject B to the imaging table 133 becomes a distance according to the magnification factor.

For example, in diagnosis of breast cancer, positional relationship between a calcification or tumor and the mammary gland structure is important. When a more detailed diagnosis of a suspicious lesion is desired, it is necessary to increase the image resolution. Therefore, magnified imaging using this mammographic apparatus 150 is effective. The other components and operations are the same those of the above-described mammographic apparatus 130, and the explanations thereof are omitted.

Figure 35:
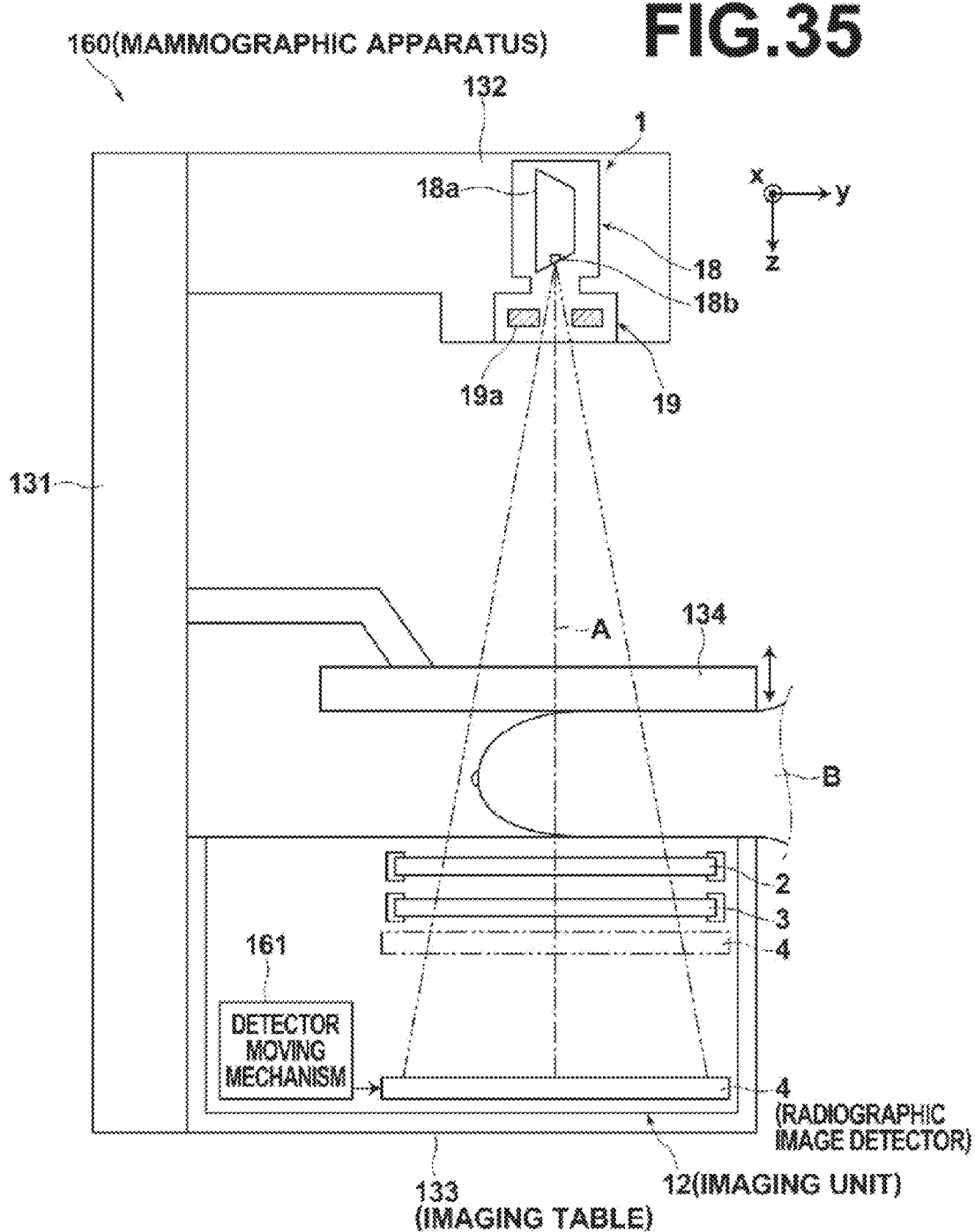
FIG. 35 is a diagram illustrating the schematic structure of another mammographic apparatus capable of magnified imaging employing one embodiment of the invention.

Next, FIG. 35 shows a mammographic apparatus 160 that is capable of magnified imaging of a subject B according to another embodiment. The mammographic apparatus 160 includes a detector moving mechanism 161 for moving the radiographic image detector 4 in the Z-direction. As the distance between the radiographic image detector 4 and the radiation source 1 is increased, an image entering the radiographic image detector 4 spreads, thereby achieving the magnified imaging of the subject B. The detector moving mechanism 161 is controlled by the controller 200 to move the radiographic image detector 4 to a position according to the magnification factor inputted via the input device 201. The other components and operations are the same as those of the above-described mammographic apparatus 130, and the explanations thereof are omitted.

Figure 36:
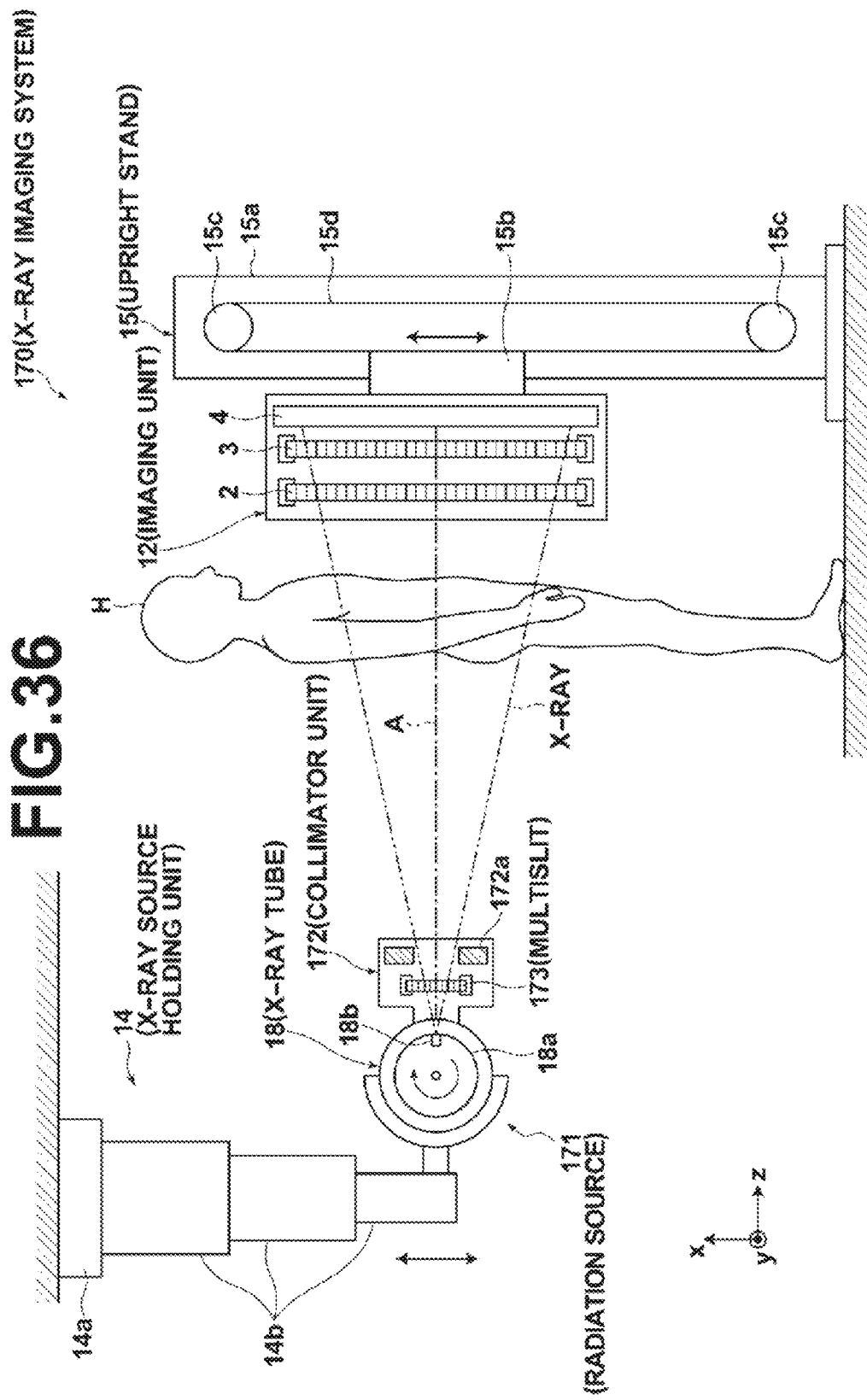
FIG. 36 is a diagram illustrating the schematic structure of an X-ray imaging system capable of imaging in the upright position having a radiation source provided with a multislit employing one embodiment of the invention.

Next, an X-ray imaging system 170 shown in FIG. 36 is different from the above-described X-ray imaging system 100 in that the X-ray imaging system 170 includes a multislit 173, which is disposed in a collimator unit 172 of the radiation source 171. The other components are the same those of the above-described X-ray imaging system 100, and the explanations thereof are omitted. The effect, structural conditions, etc., of the multislit 173 are as described above.

With the above-described systems, one phase-contrast image is obtained by performing an imaging operation with fixing the positions of the radiation source and the imaging unit. However, a plurality of imaging operations may be performed with translating the radiation source and the imaging unit in a direction orthogonal to the optical axis A of X-ray to obtain a plurality of phase-contrast images which contain partially overlapping images. In this case, a long-length image, which is larger than the size of the detection surface of the radiographic image detector, can be generated by joining the obtained phase-contrast images.

Figure 37:
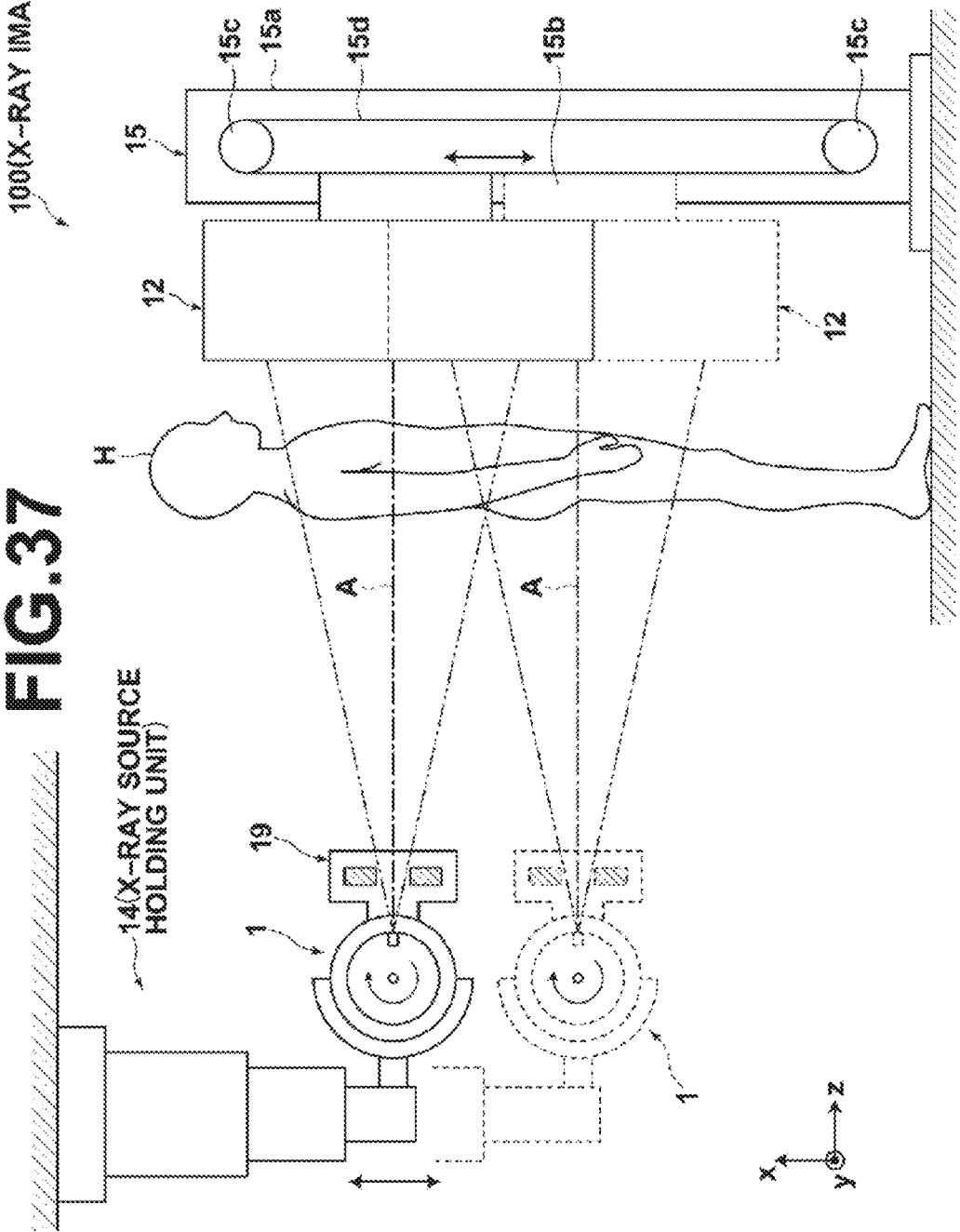
FIG. 37 is a diagram illustrating the schematic structure of an X-ray imaging system capable of long-length imaging employing one embodiment of the invention.

For example, with the above-described X-ray imaging system 100 capable of upright position imaging, the translation of the radiation source 1 and the imaging unit 12 in the X-direction orthogonal to the optical axis A of the X-ray can be achieved by controlling the X-ray source holding unit 14 and the upright stand 15 to move the radiation source 1 and the imaging unit 12 in the vertical direction in a linked manner, as shown in FIG. 37.

With the above-described X-ray imaging system 120 capable of upright position imaging and supine position imaging, the translation can be achieved by moving the pivoting arm 121 in the vertical direction along the groove 124 of the base 122. In the case of the X-ray imaging system 110, since it does not include a mechanism for translating the radiation source 1 and the imaging unit 12, a mechanism for translating the radiation source 1 and the imaging unit 12 in a direction orthogonal to the optical axis A, as described above, may be provided.

It is also preferable to generate a long-length image by performing imaging operations with moving the radiation source and the imaging unit two-dimensionally in two directions, i.e., in the X-direction and in the Y-direction, and joining the obtained phase-contrast images in the two-dimensional directions.

The above-described embodiments show examples where a two-dimensional phase-contrast image is obtained. While the phase-contrast image allows depicting soft tissues, such as tendon, blood vessels, etc., which are difficult to be depicted by conventional X-ray imaging, the depicted soft tissues may introduce obstructive shadows in the two-dimensional image.

Figure 38:
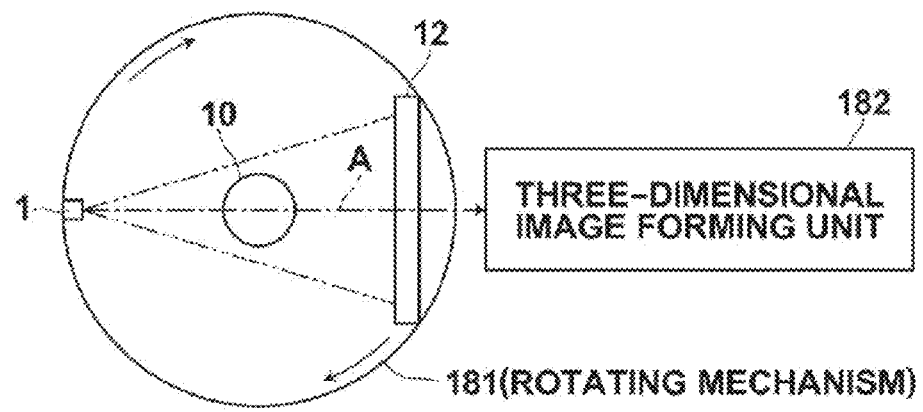
FIG. 38 is a diagram illustrating the schematic structure of a CT imaging apparatus employing one embodiment of the invention.

In order to separate such obstructive shadows to allow accurate diagnosis and image interpretation, the invention may be applied to a radiographic phase-contrast CT apparatus that obtains a three-dimensional image. Specifically, as shown in FIG. 38, a rotating and moving mechanism 181 may be provided for rotating the radiation source 1 and the imaging unit 12 in the direction indicated by the arrow about a subject 10 placed between the radiation source 1 and the imaging unit 12, which includes the first and second gratings 2 and 3 and the radiographic image detector 4, and a three-dimensional image of the subject 10 may be formed by a three-dimensional image forming unit 182 based on a plurality of phase-contrast images of the subject 10 obtained by the imaging unit 12 at different angles of rotation provided by the rotating and moving mechanism 181. The method for forming a three-dimensional image based on a plurality of images is the same as that used with conventional X-ray CT apparatuses. Also in the case where the invention is applied to the radiographic phase-contrast CT apparatus, the subject 10 may be placed between the first grating 2 and the second grating 3. Further, the above-described radiation source including the multislit may be used in place of the radiation source 1.

Figure 39:
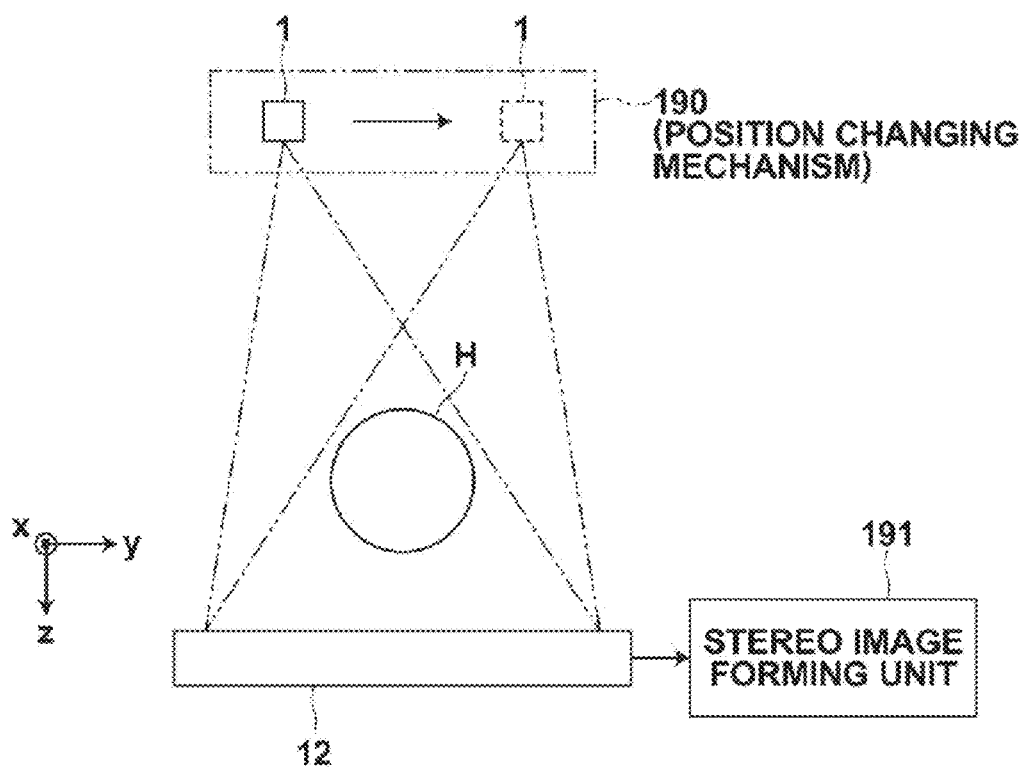
FIG. 39 is a diagram illustrating the schematic structure of a stereo imaging apparatus employing one embodiment of the invention.

In order to separate the above-described obstructive shadows to allow accurate diagnosis and image interpretation, it is also preferable to apply the invention to stereo imaging for obtaining a stereo image, which allows stereoscopic viewing. Specifically, as shown in FIG. 39, a position changing mechanism 190 for changing the position of the radiation source 1 relative to a subject H and the imaging unit 12 in the direction indicated by the arrow (Y-direction) is provided, and a stereo image of the subject H is formed by a stereo image forming unit 191 based on two phase-contrast images of the subject H obtained by the imaging unit 12 at the first and second positions provided by the position changing mechanism 190.

It is preferable to adjust the collimator 19a such that the X-ray radiation range of the radiation source 1 is aligned with the image reception area of the imaging unit 12 both at the first and second positions. It is also preferable to change the angle of the radiation source 1 between the first position and the second position (to achieve so-called swiveling) to align the X-ray radiation range with the image reception area.

The method for forming a stereo image based on two images is the same as that used with conventional stereo imaging apparatuses. Also in this configuration, the subject H may be placed between the first grating 2 and the second grating 3.

According to this configuration, the position of the radiation source 1 is changed along the Y-direction (the direction in which the members 22 and 32 of the first and second gratings 2 and 3 extend), and this is advantageous in that no vignetting of radiation due to the change of the position of the radiation source 1 occurs.

According to the embodiments of the systems as described above, one phase-contrast image can be generated by a single imaging operation, in contrast to a conventional method where one phase-contrast image is generated by performing a plurality of imaging operations with translating the gratings. Therefore, degradation of image quality of the phase-contrast image due to body motion or vibration of the apparatus can be prevented. Further, since a high precision mechanism for moving the gratings is not necessary, the apparatus can be simplified and cost reduction can be achieved.

The above-described embodiments provide an image which has conventionally been difficult to be depicted by obtaining a phase contrast image. Since conventional X-ray radiodiagnostics are based on absorption images, referencing an absorption image together with a corresponding phase contrast image can help image interpretation. For example, it is effective that a part of a body site which cannot be depicted in the absorption image is supplemented with image information of the phase contrast image by superimposing the absorption image and the phase contrast image one another through suitable processing, such as weighting, tone processing or frequency processing.

However, if the absorption image is taken separately from the phase contrast image, it is difficult to successfully superimpose the absorption image and the phase contrast image one another due to positional change of the subject body part between an imaging operation to take the phase contrast image and an imaging operation to take the absorption image. In addition, this may lead to increase of the number of imaging operations, and thus may increase the burden on the subject. In recent years, small-angle scattering images are drawing attention, besides the phase contrast images and the absorption images. The small-angle scattering image can depict tissue characteristics attributed to minute structures in a subject tissue, and is expected to be a depiction method for new imaging diagnosis in the fields of cancers and cardiovascular diseases, for example.

To this end, the calculation processor 202 may further include an absorption image generation unit for generating an absorption image from the fringe images, which are obtained for generating the phase contrast image, or a small-angle scattering image generation unit for generating a small-angle scattering image from the fringe images. It should be noted that the calculation processor 202 may generate at least one of a phase-contrast image, a small-angle scattering image and an absorption image.

Figure 40:
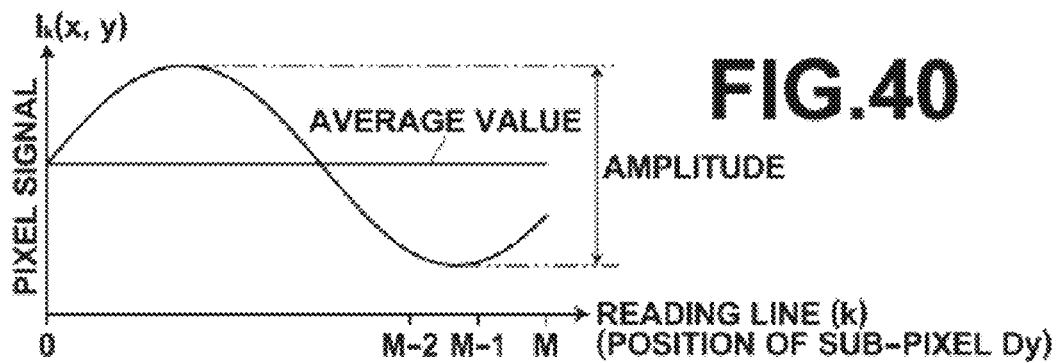
FIG. 40 is a diagram for explaining methods for generating an absorption image and a small-angle scattering image.

The absorption image generation unit generates the absorption image by averaging pixel signals Ik(x,y), which are obtained for each pixel, with respect to k, as shown in FIG. 40, to calculate an average value for each pixel to form an image. The calculation of the average value may be achieved by simply averaging the pixel signals Ik(x,y) with respect to k. However, since a large error occurs when M is small, the pixel signals Ik(x,y) may be fitted by a sinusoidal wave, and then an average value of the fitted sinusoidal wave may be calculated. Besides a sinusoidal wave, a square wave form or a triangular wave form may be used.

The method used to generate the absorption image is not limited to one using the average value, and any other value corresponding to the average value, such as an addition value calculated by adding up the pixel signals Ik(x,y) with respect to k, may be used.

The small-angle scattering image generation unit generates the small-angle scattering image by calculating an amplitude value of the pixel signals Ik(x,y) obtained for each pixel to form an image. The calculation of the amplitude value may be achieved by calculating a difference between the maximum value and the minimum value of the pixel signals Ik(x,y). However, since a large error occurs when M is small, the pixel signals Ik(x,y) may be fitted by a sinusoidal wave, and then an amplitude value of the fitted sinusoidal wave may be calculated. The method used to generate the small-angle scattering image is not limited to one using the amplitude value, and any other value corresponding to a variation relative to the average, such as a variance value or a standard deviation, may be used.

The phase contrast image is based on refracted components of the X-ray in the direction (the X-direction) in which the members 22 and 32 of the first and second gratings 2 and 3 are periodically arranged, and does not reflect refracted components in the direction (the Y-direction) in which the members 22 and 32 extend. That is, a contour of a body site along a direction intersecting with the X-direction (or the Y-direction if the direction is orthogonal to the X-direction) is depicted via the plane of the grating, which is the XY-plane, in a phase contrast image based on the refracted components in the X-direction, and a contour of the body site in the X-direction, which does not intersect with the X-direction, is not depicted in the phase contrast image in the X-direction. That is, there is a body site which cannot be depicted depending on the shape and orientation of the body site, which is a subject H. For example, it is believed that, when the direction of a plane of loading of an articular cartilage of the knee, or the like, is aligned with the Y-direction among the X- and Y-directions in the plane of the grating, a contour of the body site in the vicinity of the plane of loading (the YZ-plane) almost along the Y-direction is sufficiently depicted, but tissues (such as tendon and ligament) around the cartilage extending almost in the X-direction and intersecting with the plane of loading are depicted insufficiently. Although it is possible to retake the image of the insufficiently depicted body site with moving the subject H, this increases the burden on the subject H and the operator, and it is difficult to ensure positional repeatability between the image taken first and the image retaken next.

Figure 41:
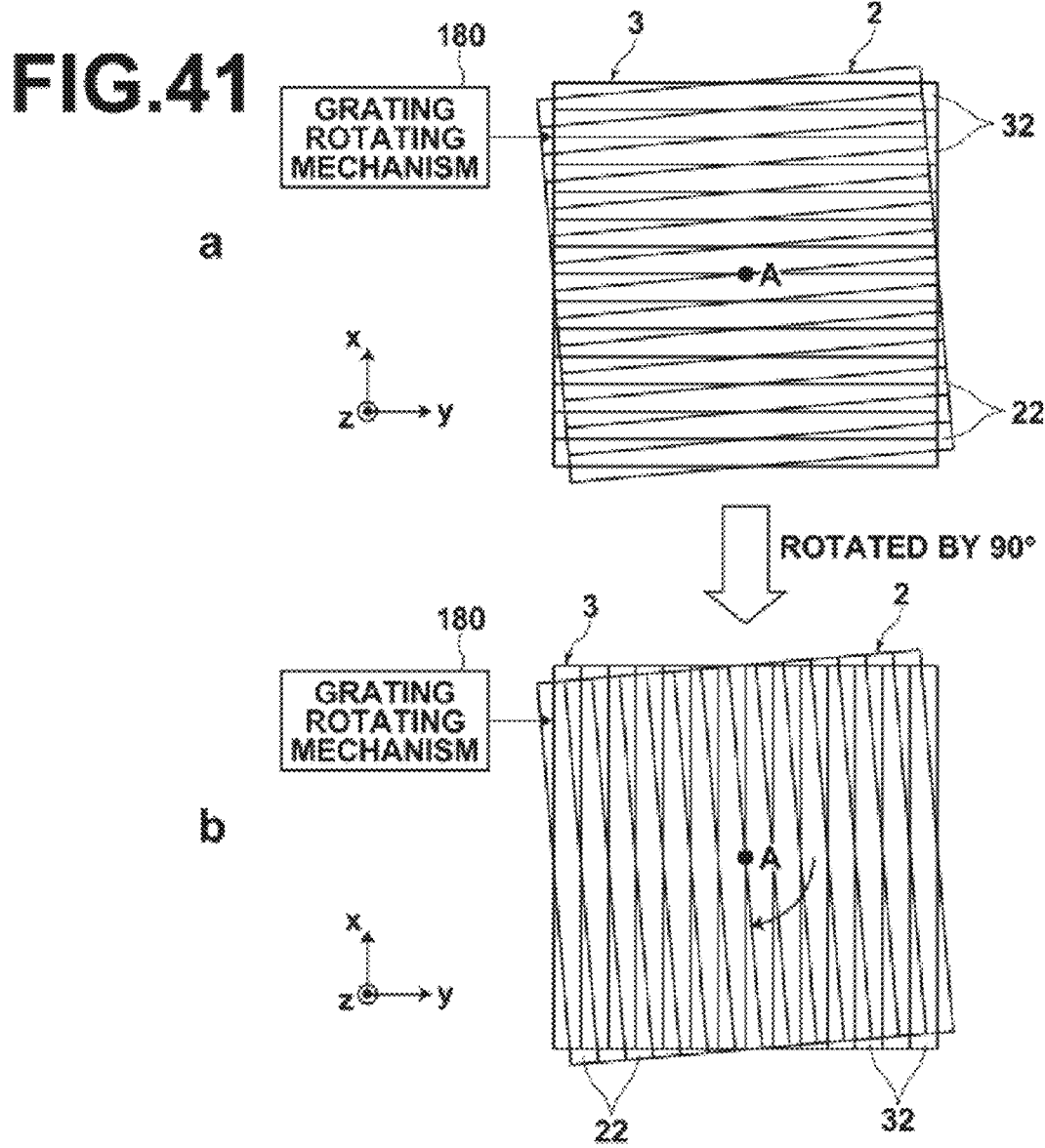
FIG. 41 is a diagram for explaining a structure for rotating the first and second gratings by an angle of 90°.

In order to address this problem, another preferred example is shown in FIG. 41, where a rotating mechanism 180 for rotating the first and second gratings 2 and 3 is provided. The rotating mechanism 180 rotates the first and second gratings 2 and 3 by an arbitrary angle from a first orientation, as shown at "a" in FIG. 41, around an imaginary line (the optical axis A of the X-ray) orthogonal to the center of the plane of the first and second gratings 2 and 3 into a second orientation as shown at "b" in FIG. 41, so that phase contrast images with respect to the first orientation and with respect to the second orientation are generated.

In this manner, the above-described problem of positional repeatability can be solved. It should be noted that, although the orientation shown at "a" in FIG. 41 is the first orientation of the first and second gratings 2 and 3 where the members 32 of the second grating 3 extends along the Y-direction, and the orientation shown at "b" in FIG. 41 is the second orientation of the first and second gratings 2 and 3 where the first and second gratings 2 and 3 are rotated by 90° from the state shown at "a" in FIG. 41 such that the members 32 of the second grating 3 extends in the X-direction, the rotational angle of the first and second gratings 2 and 3 may be any angle as long as the relative inclination between the first grating 2 and the second grating 3 is maintained. Further, the rotating operation may be performed twice or more to generate phase contrast images with respect to a third orientation, a fourth orientation, and the like, in addition to the phase contrast images with respect to the first orientation and the second orientation.

It should be noted that the rotating mechanism 180 may rotate only the first and second gratings 2 and 3 in an integrated manner independently from the radiographic image detector 4, or may rotate the first and second gratings 2 and 3 with the radiographic image detector 4 in an integrated manner. Further, the generation of the phase-contrast images in the first and second orientations using the rotating mechanism 180 is applicable to either of the above-described examples. In the case where the above-described multislit is included, the multislit is also rotated into the same orientation as that of the first grating 2.

While FIG. 41 shows an example where the first grating 2 and the second grating 3 are inclined relative to each other, this is not intended to limit the invention. The above-described aspect where the second grating 3 has a pitch different from the pitch of the self image G1 of the first grating 2 at the position of the second grating 3 is also applicable. Further, the first grating 2 and the second grating 3 having such a relationship may be rotated by 90°, similarly to the above description.

Figure 42:
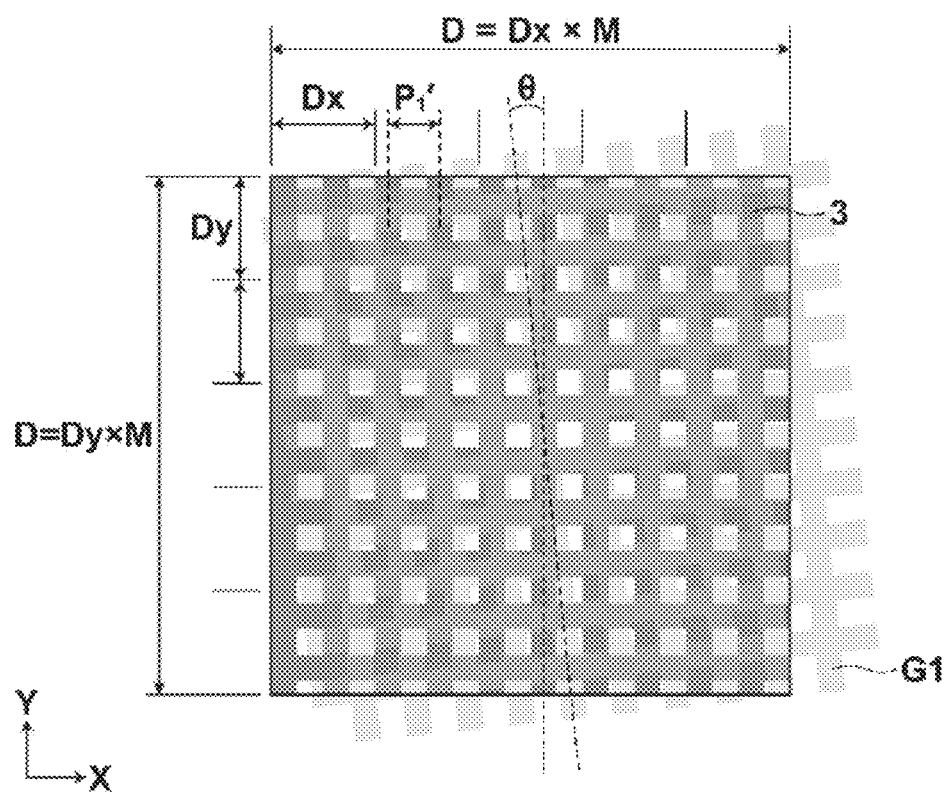
FIG. 42 is a diagram for explaining an example where the first and second gratings are two-dimensional gratings.

Still further, rather than rotating the first and second gratings 2 and 3 which are one-dimensional gratings, as described above, the first and second gratings 2 and 3 may be formed as two-dimensional gratings, where the members 22 and 32 extend in two-dimensional directions, respectively. FIG. 42 shows the self image G1 of the first grating 2 that is configured as a two-dimensional grating, and the second grating 3 that is configured as a two-dimensional grating. The angle of rotation θ of the first grating 2 relative to the second grating 3 is set based on Expression (13), (21) or (32) above, similarly to the above-described embodiments.

In this case, while Expressions (13), (21) and (32) above are with respect to the sub-pixel size, θ is set to satisfy Expression (13), (21) or (32) above not only with respect to the sub-pixel size but also with respect to the pixel size in the direction orthogonal to the direction of the sub-pixel size. For example, assuming that the number of fringe images used to obtain a phase-contrast image is M, the first grating 2 is inclined relative to the second grating 3 such that M pixel sizes Dx correspond to one image resolution D in the main scanning direction of the phase-contrast image with respect to the X-direction, similarly to the Y-direction, and different fringe images are obtained also for each pixel Dx with respect to the X-direction.

Comparing this configuration with the configuration where the one-dimensional gratings are rotated, this configuration provides the phase contrast images corresponding to the first and second directions by a single imaging operation, and thus the phase contrast images are not influenced by body motion of the subject and vibration of the apparatus between imaging operations, thereby ensuring good positional repeatability between the phase contrast images corresponding to the first and second directions. Further, by eliminating the rotating mechanism, simplification of the apparatus and cost reduction can be achieved.

While FIG. 42 shows an example where the first grating 2 and the second grating 3 formed by two-dimensional gratings are inclined relative to each other, this is not intended to limit the invention. The above-described aspect where the second grating 3 has a pitch different from the pitch of the self image G1 of the first grating 2 at the position of the second grating 3 is also applicable. In this case, for example, the pitch of the self image G1 of the first grating 2 in the X-direction at the position of the second grating 3 is different from the pitch of the second grating 3 in the X-direction, and the pitch of the self image G1 in the Y-direction is different from the pitch of the second grating 3 in the Y-direction.

What is claimed is:

1. A radiographic phase-contrast imaging apparatus comprising:
   a radiation source;
   a first grating having a periodically arranged grating structure and allowing radiation emitted from the radiation source to pass therethrough to form a periodic pattern image;
   a second grating having a periodically arranged grating structure including areas transmitting the periodic pattern image formed by the first grating and areas shielding the periodic pattern image;
   a radiographic image detector including two-dimensionally arranged pixels for detecting the radiation transmitted through the second grating, wherein the first grating and the second grating are adapted to form a moire pattern when the periodic pattern image formed by the first grating and the second grating are superimposed one another; and
   a phase-contrast image generating unit for obtaining image signals of a plurality of fringe images based on an image signal of the moire pattern detected by the radiographic image detector, and generating a phase-contrast image based on the obtained image signals of the fringe images, wherein the fringe images correspond to different pixel groups located at different positions from one another with respect to a predetermined direction, each pixels group includes pixels arranged at intervals of a predetermined number of pixels in the predetermined direction, image signals read out from the pixels of each pixel group are obtained as the image signal of each fringe image, and the predetermined direction is a direction parallel to or a direction intersecting a period direction of the moire pattern other than a direction orthogonal to the period direction of the moire pattern.

2. The radiographic phase-contrast imaging apparatus as claimed in claim 1, wherein the first grating and the second grating are positioned such that a direction in which the periodic pattern image formed by the first grating extends and a direction in which the second grating extends are inclined relative to each other.

3. The radiographic phase-contrast imaging apparatus as claimed in claim 2, wherein the first grating and the second grating are configured such that a period T of the moire pattern has a value that satisfies the Expression below:

$$T = \frac{L}{Z_1 + Z_2} \times \frac{P_1'}{\tan\theta} \geqq 3Dsub$$

where $Z_1$ is a distance between a focal spot of the radiation source and the first grating, $Z_2$ is a distance between the first grating and the second grating, L is a distance between the focal spot of the radiation source and the radiographic image detector, $P_1'$ is a pitch of the periodic pattern image at a position of the second grating, Dsub is a size of the pixel in the predetermined direction, and θ is an angle formed between the direction in which the periodic pattern image formed by the first grating extends and the direction in which the second grating extends.

4. The radiographic phase-contrast imaging apparatus as claimed in claim 2, further comprising:
a multislit disposed between the radiation source and the first grating, the multislit being formed by an absorption type grating including a plurality of radiation shielding members arranged at a predetermined pitch for shielding the radiation applied from the radiation source in an area-selective manner,
wherein the first grating and the second grating are configured such that a period T of the moire pattern has a value that satisfies the Expression below:

$$T = \frac{L}{Z_1 + Z_2} \times \frac{P_1'}{\tan\theta} \geqq 3Dsub$$

where $Z_1$ is a distance between a focal spot of the radiation source and the first grating, $Z_2$ is a distance between the first grating and the second grating, L is a distance between the focal spot of the radiation source and the radiographic image detector, $P_1'$ is a pitch of the periodic pattern image at a position of the second grating, Dsub is a size of the pixel in the predetermined direction, and θ is an angle formed between the direction in which the periodic pattern image formed by the first grating extends and the direction in which the second grating extends.

5. The radiographic phase-contrast imaging apparatus as claimed in claim 4, wherein a pitch $P_3$ of the multislit has a value that satisfies the Expression below:

$$P_3 = \frac{Z_3}{Z_2} P_1'$$

where $Z_3$ is a distance between the multislit and the first grating, $Z_2$ is a distance from the first grating to the second grating, and $P_1'$ is a pitch of the periodic pattern image at a position of the second grating.

6. The radiographic phase-contrast imaging apparatus as claimed in claim 2, wherein a relative inclination angle θ between the periodic pattern image formed by the first grating and the second grating is set to be a value that satisfies the Expression below:

$$\theta = \arctan\left\{n \times \frac{P_1'}{D}\right\}$$

where $P_1'$ is a pitch of the periodic pattern image at a position of the second grating, D is a value of the size of the pixel in the predetermined direction multiplied by the number of fringe images M, and n is an integer other than 0 or a multiple of M.

7. The radiographic phase-contrast imaging apparatus as claimed in claim 2, wherein
the first grating is a phase modulation grating that applies phase modulation of 90° or an amplitude modulation grating, and
a pitch $P_1'$ of the periodic pattern image at a position of the second grating and a pitch $P_2$ of the second grating have values that satisfy the Expression below:

$$P_2 = P_1' = \frac{Z_1 + Z_2}{Z_1} P_1$$

where $P_1$ is a grating pitch of the first grating, $Z_1$ is a distance from a focal spot of the radiation source to the first grating, and $Z_2$ is a distance from the first grating to the second grating.

8. The radiographic phase-contrast imaging apparatus as claimed in claim 2, wherein
the first grating is a phase modulation grating that applies phase modulation of 180°, and
a pitch $P_1'$ of the
periodic pattern image at a position of the second grating and a pitch $P_2$ of the second grating have values that satisfy the Expression below:

$$P_2 = P_1' = \frac{Z_1 + Z_2}{Z_1} \frac{P_1}{2}$$

where $P_1$ is a grating pitch of the first grating, $Z_1$ is a distance from a focal spot of the radiation source to the first grating, and $Z_2$ is a distance from the first grating to the second grating.

9. The radiographic phase-contrast imaging apparatus as claimed in claim 2, wherein
the radiographic image detector includes the pixels two-dimensionally arranged in first and second directions that are orthogonal to each other, and
the direction in which the periodic pattern image formed by the first grating extends or the direction in which the second grating extends is parallel to the first direction.

10. The radiographic phase-contrast imaging apparatus as claimed in claim 9, wherein the phase-contrast image generating unit obtains the image signals of the fringe images based on image signals readout from a predetermined number of pixels in the first direction depending on the relative inclination between the direction in which the periodic pattern image formed by the first grating extends and the direction in which the second grating extends.

11. The radiographic phase-contrast imaging apparatus as claimed in claim 1, wherein the first grating and the second grating are configured such that a pitch of the periodic pattern image at a position of the second grating is different from a pitch of the second grating.

12. The radiographic phase-contrast imaging apparatus as claimed in claim 11, wherein the direction in which the periodic pattern image formed by the first grating extends is parallel to the direction in which the second grating extends.

13. The radiographic phase-contrast imaging apparatus as claimed in claim 11, wherein the first grating and the second grating are configured such that a period T of the moire pattern has a value that satisfies the Expression below:

$$T = \frac{L}{Z_1 + Z_2} \times \left| \frac{P_1' P_2}{P_1' - P_2} \right| \geq 3 Dsub$$

where $Z_1$ is a distance between a focal spot of the radiation source and the first grating, $Z_2$ is a distance between the first grating and the second grating, L is a distance between the focal spot of the radiation source and the radiographic image detector, $P_2$ is a pitch of the second grating, $P_1'$ is a pitch of the periodic pattern image at a position of the second grating, and Dsub is a size of the pixel in the predetermined direction.

14. The radiographic phase-contrast imaging apparatus as claimed in claim 11, further comprising:
a multislit disposed between the radiation source and the first grating, the multislit being formed by an absorption type grating including a plurality of radiation shielding members arranged at a predetermined pitch for shielding the radiation applied from the radiation source in an area-selective manner,
wherein the first grating and the second grating are configured such that a period T of the moire pattern has a value that satisfies the Expression below:

$$T = \frac{L}{Z_1 + Z_2} \times \left| \frac{P_1' P_2}{P_1' - P_2} \right| \geq 3 Dsub$$

where $Z_1$ is a distance between a focal spot of the radiation source and the first grating, $Z_2$ is a distance between the first grating and the second grating, L is a distance between the focal spot of the radiation source and the radiographic image detector, $P_2$ is a pitch of the second grating, $P_1'$ is a pitch of the periodic pattern image at a position of the second grating, and Dsub is a size of the pixel in the predetermined direction.

15. The radiographic phase-contrast imaging apparatus as claimed in claim 14, wherein a pitch $P_3$ of the multislit has a value that satisfies the Expression below:

$$P_3 = \frac{Z_3}{Z_2} P_1'$$

where $Z_3$ is a distance between the multislit and the first grating, $Z_2$ is a distance from the first grating to the second grating, and $P_1'$ is a pitch of the periodic pattern image at a position of the second grating.

16. The radiographic phase-contrast imaging apparatus as claimed in claim 11, wherein the first grating is a phase modulation grating that applies phase modulation of 90° or an amplitude modulation grating, and
the pitch $P_1'$ of the periodic pattern image at the position of the second grating has a value that satisfies the Expression below:

$$P_1' = \frac{Z_1 + Z_2}{Z_1} P_1$$

where $P_1$ is a grating pitch of the first grating, $Z_1$ is a distance from a focal spot of the radiation source to the first grating, and $Z_2$ is a distance from the first grating to the second grating.

17. The radiographic phase-contrast imaging apparatus as claimed in claim 11, wherein the first grating is a phase modulation grating that applies phase modulation of 180°, and
the pitch $P_1'$ of the periodic pattern image at the position of the second grating has a value that satisfies the Expression below:

$$P_1' = \frac{Z_1 + Z_2}{Z_1} \frac{P_1}{2}$$

where $P_1$ is a grating pitch of the grating, $Z_1$ is a distance from a focal spot of the radiation source to the first grating, and $Z_2$ is a distance from the first grating to the second grating.

18. The radiographic phase-contrast imaging apparatus as claimed in claim 1, wherein the radiographic image detector includes the pixels being two-dimensionally arranged and provided with switching elements for reading out the image signals.

19. The radiographic phase-contrast imaging apparatus as claimed in claim 1, further comprising a linear reading light source for emitting linear reading light,
wherein reading of the image signals from the radiographic image detector is achieved by scanning of the linear reading light source.

20. The radiographic phase-contrast imaging apparatus as claimed in claim 1, wherein the phase-contrast image generating unit obtains image signals read out from pixels adjacent to each other in the predetermined direction as the image signals of different fringe images.

21. The radiographic phase-contrast imaging apparatus as claimed in claim 1, wherein the phase-contrast image generating unit obtains image signals read out from pixels arranged at intervals of at least two pixels in the predetermined direction of each pixel group as the image signal of each fringe image, and obtains the image signals read out from the different pixel groups as the image signals of different fringe images.

22. The radiographic phase-contrast imaging apparatus as claimed in claim 1, wherein the second grating is positioned at a Talbot interference distance from the first grating, and applies intensity modulation to the periodic pattern image formed by a Talbot interference effect of the first grating.

23. The radiographic phase-contrast imaging apparatus as claimed in claim 1, wherein the first grating is an absorption type grating that allows the radiation to pass therethrough as a projection image to form the periodic pattern image, and
the second grating applies intensity modulation to the periodic pattern image that is the projection image transmitted through the first grating.

24. The radiographic phase-contrast imaging apparatus as claimed in claim 23, wherein the second grating is positioned at a distance shorter than a minimum Talbot interference distance from the first grating.

25. The radiographic phase-contrast imaging apparatus as claimed in claim 1, wherein a size of the pixel in the predetermined direction is smaller than a size of the pixel in a direction orthogonal to the predetermined direction.

26. The radiographic phase-contrast imaging apparatus as claimed in claim 1, wherein the radiation source and the radiographic image detector are positioned to face each other in the horizontal direction, and the radiographic phase-contrast imaging apparatus is adapted to be capable of imaging a subject in the upright position.

27. The radiographic phase-contrast imaging apparatus as claimed in claim 1, wherein the radiation source and the radiographic image detector are positioned to face each other in the vertical direction, and the radiographic phase-contrast imaging apparatus is adapted to be capable of imaging a subject in the supine position.

28. The radiographic phase-contrast imaging apparatus as claimed in claim 1, wherein the radiation source and the radiographic image detector are held by a pivoting arm, and the radiographic phase-contrast imaging apparatus is adapted to be capable of imaging a subject in the upright position and imaging a subject in the supine position.

29. The radiographic phase-contrast imaging apparatus as claimed in claim 1, wherein the radiographic phase-contrast imaging apparatus is a mammographic apparatus adapted to be capable of imaging a breast as a subject.

30. The radiographic phase-contrast imaging apparatus as claimed in claim 1, further comprising:
a moving mechanism for moving the radiation source between a first position, from which the radiation is applied to the radiographic image detector from a first direction, and a second position, from which the radiation is applied to the radiographic image detector from a second direction different from the first direction, wherein the phase-contrast image generating unit generates a phase-contrast image based on the image signals detected by the radiographic image detector at each of the first position and the second position; and
a stereo image forming unit for forming a stereo image based on the phase-contrast image corresponding to the first position and the phase-contrast image corresponding to the second position.

31. The radiographic phase-contrast imaging apparatus as claimed in claim 1, further comprising:
an orbiting mechanism for making the radiation source and the radiographic image detector orbit about a subject, wherein the phase-contrast image generating unit generates a phase-contrast image at each angle of rotation provided by the orbiting mechanism based on the image signals detected by the radiographic image detector at the angle of rotation; and
a three-dimensional image forming unit for forming a three-dimensional image based on the phase-contrast images at the angles of rotation.

32. The radiographic phase-contrast imaging apparatus as claimed in claim 1, further comprising a rotating mechanism for rotating the first and second gratings by an angle of 90° from directions along which the gratings extend about an axis of rotation extending orthogonally to grating surfaces of the first and second gratings.

33. The radiographic phase-contrast imaging apparatus as claimed in claim 1, wherein the first and second gratings are configured as two-dimensional gratings.

34. A radiographic phase-contrast imaging apparatus comprising:
a radiation source;
a first grating having a periodically arranged grating structure and allowing radiation emitted from the radiation source to pass therethrough to form a periodic pattern image;
a second grating having a periodically arranged grating structure including areas transmitting the periodic pattern image formed by the first grating and areas shielding the periodic pattern image;
a radiographic image detector including two-dimensionally arranged pixels for detecting the radiation transmitted through the second grating, wherein the first grating and the second grating are adapted to form a moire pattern when the periodic pattern image formed by the first grating and the second grating are superimposed one another; and
a phase-contrast image generating unit for obtaining image signals of a plurality of fringe images based on an image signal of the moire pattern detected by the radiographic image detector, and generating at least one of a phase-contrast image, a small-angle scattering image and an absorption image based on the obtained image signals of the fringe images, wherein the fringe images correspond to different pixel groups located at different positions from one another with respect to a predetermined direction, each pixels group includes pixels arranged at intervals of a predetermined number of pixels in the predetermined direction, image signals read out from the pixels of each pixel group are obtained as the image signal of each fringe image, and the predetermined direction is a direction parallel to or a direction intersecting a period direction of the moire pattern other than a direction orthogonal to the period direction of the moire pattern.

* * * * *